United States Patent [19]
Higa et al.

[11] Patent Number: 5,936,076
[45] Date of Patent: Aug. 10, 1999

[54] αGALACTOSYLCERAMIDE DERIVATIVES

[75] Inventors: Tatsuo Higa, Naha; Koji Akimoto, Takasaki; Yasuhiko Koezuka, Takasaki; Teruyuki Sakai, Takasaki; Masahiro Morita, Takasaki; Takenori Natori, Takasaki, all of Japan

[73] Assignee: Kirin Beer Kabushiki Kaisha, Tokyo, Japan

[21] Appl. No.: 08/450,109

[22] Filed: May 25, 1995

Related U.S. Application Data

[63] Continuation of application No. 08/148,004, Nov. 5, 1993, abandoned, which is a continuation-in-part of application No. 07/876,564, Apr. 30, 1992, abandoned.

[30] Foreign Application Priority Data

Aug. 29, 1991 [JP] Japan ................................. 3-244384

[51] Int. Cl.⁶ ........................... C07H 15/00; A61K 31/70
[52] U.S. Cl. ........................ 536/17.9; 536/4.1; 536/18.7; 536/53; 536/127; 536/128; 514/25; 424/520
[58] Field of Search ..................... 536/4.1, 18.7, 536/53, 17.9, 127, 128; 514/25; 424/520

[56] References Cited

U.S. PATENT DOCUMENTS

| | | | |
|---|---|---|---|
| 4,598,051 | 7/1986 | Papahadjopoulos et al. | 436/512 |
| 4,728,641 | 3/1988 | Tubaro et al. | 514/54 |
| 4,806,466 | 2/1989 | Paphadjopoulos et al. | 436/519 |
| 4,816,450 | 3/1989 | Bell et al. | 514/28 |
| 4,831,021 | 5/1989 | Tubaro et al. | 536/53 |
| 4,859,769 | 8/1989 | Karlsson et al. | 536/53 |
| 4,937,232 | 6/1990 | Bell et al. | 574/28 |
| 4,952,683 | 8/1990 | Tschannen | 536/186 |
| 5,026,557 | 6/1991 | Estis et al. | 424/450 |
| 5,028,715 | 7/1991 | Lyle | 548/193 |
| 5,041,441 | 8/1991 | Rodin et al. | 514/237.8 |
| 5,073,543 | 12/1991 | Marshall | 514/21 |
| 5,210,073 | 5/1993 | Yodoi | 514/12 |
| 5,567,684 | 10/1996 | Ladish | 514/25 |

FOREIGN PATENT DOCUMENTS

| | | |
|---|---|---|
| 0254105 | 1/1988 | European Pat. Off. . |
| 371414 | 11/1989 | European Pat. Off. . |
| 0609437 | 8/1994 | European Pat. Off. . |
| 650732 | 5/1995 | European Pat. Off. . |
| 61-57594 | 3/1986 | Japan . |
| 62-39597 | 2/1987 | Japan . |
| 63-45293 | 2/1988 | Japan . |
| 64-95 | 1/1989 | Japan . |
| 193562 | 4/1989 | Japan . |
| 9356289 | 4/1989 | Japan . |
| 5-9193 | 8/1991 | Japan . |
| 5-59081 | 3/1993 | Japan . |
| 2588729 | 12/1996 | Japan . |
| 9212986 | 8/1992 | WIPO . |
| 93/05055 | 3/1993 | WIPO . |

OTHER PUBLICATIONS

English translation of JP Application 93562/1989.
English translation of claims of Japanese Patent 2588729, 1996.

Zubay "Biochemistry", Benjamin/Cummings Publishing Co., Inc., 1983, p.527.

Sweeley, C. C. "Sphingolipids" p. 327–361, New Comprehensive Biochemistry—Biochemistry of Lipids, Lipoproteins and Membranes vol. 20, Elsevier 1991.

Sweeley, C. C. "Chemistry of Mammalian Glycolipids" p. 459–541 in The Glycoconjugates–vol. 1—Mammalian Glycoproteins edited Martin Horowitz 1977.

Mecher, B. A. et al. Glycosphingolipids . . . p. 236–250, Methods of Enzymology vol. L. Complex Carbohydrates Part C edited by Victor Ginsburg 1978 Academic Press.

Stults, C. L. M. et al. Glycosphingolipi pp. 167–214 in Methods of Enzymology vol. 179 Complex Carbohydrates Part F edited by Victor Ginsburg 1989, Academic Press.

Hakomori, Sen–itiroh "Chemistry of Glycosphingolipids" p. 1–165 in Handbook of Lipid Research vol. B. Sphingolipid Biochemistry ed. Donald J. Hanahan 1983.

Makita, A. Glycosphingolipids p. 1–99 in New Comprehensive Biochemistry vol. 10 ed. H. Wiegandt 1985.

(List continued on next page.)

*Primary Examiner*—Kathleen K. Fonda
*Attorney, Agent, or Firm*—Ladas & Parry

[57] ABSTRACT

The present invention relates to the novel α-galactosylceramide represented by the formula (A):

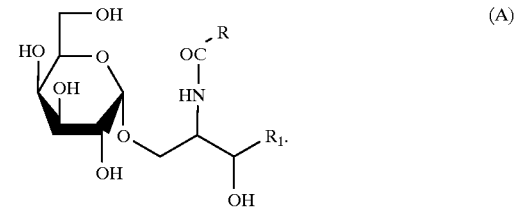

(A)

wherein R represents

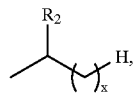

where $R_2$ represents H or OH and X denotes an integer of 0–26, or R represents —$(CH_2)_7CH=CH(CH_2)_7CH_3$ and $R_1$ represents any one of the substituents defined by the following (a)–(e):

(a) —$CH_2(CH_2)_YCH_3$,
(b) —$CH(OH)(CH_2)_YCH_3$,
(c) —$CH(OH)(CH_2)_YCH(CH_3)_2$,
(d) —$CH=CH(CH_2)_YCH_3$, and
(e) —$CH(OH)(CH_2)_YCH(CH_3)CH_2CH_3$, wherein Y denotes an integer of 5–17.

The present invention also relates to an anti-tumor agent and an immunostimulator comprising one or more of the aforementioned compounds as effective ingredients.

60 Claims, 22 Drawing Sheets

OTHER PUBLICATIONS

Yu, R. K. et al. "Structure and Localization of Gangliosides" p. 1–42 in Neurobiology of Glycoconjugates ed. Richard U. Margolis (1989).

Nishizuka Y. Science 233, 305–312 (1986).

Kaibuchi K. et al. J. Biol. Chem. 260, 1366–1369 (1985).

Crabtree, G. R. Science, 243, 355–361 (1989).

Wepsic, T. H. et al. Immunopharmacol. Immunotoxicol. 11, 81–99 (1989).

R. J. Robb, The Journal of Immunology vol. 136, 971–976 (1986).

E. G. Bremer, The Journal of Biological Chemistry 261, 2434–2440 (1986).

Higuchi, R., et al. "Structure and Biological Activity of Ganglioside Molecular Species." Liebigs Annalen der Chemie, vol. 1993, No. 4, Apr. 1993, pp. 359–366.

Sugiyama, S., et al. "Biologically Active Glycosides . . ." Leibigs Annalen der Chemie; 1991, No. 4,pp. 349–356; (Apr. 4, 1991).

Schmidt, R.R., et al. Synthesis of D–ribo–and L–lyxo–Phytosphingosi Carbohydrate Research; vol. 174, (1988) pp. 169–179.

Koike, et al. Carbohydrate Research, vol. 162, No. 2, pp. 237–246, May 1, 1987.

Costello, et al. ACS Symposium Series: Gel Surface Glycolycide, vol. 128, pp. 35–54, 1980.

Higuchi, R. et al. "Structures of three New Cerebrosides . . ." Liebigs Ann Chem., 1990, 659–663.

Higuchi, R., et al "Isolation and Characterization . . ." Liebigs. Ann. Chem. 1990, 51–55.

Shiio, T. Jpn J. Cancer Chemother. 15(3) Mar. 1988, pp. 481–485.

Taguchi, T. Jpn. J. Cancer Chemother. 12(2) Feb. 1985, pp. 366–378.

Tanikawa, S. et al. Blood vol. 76, No. 3, Aug. 1, 1990, pp. 445–449.

Okano, A. et al. Transplantation, vol. 47, No. 4, p. 738–740 Apr. 1989.

Komori, T. et al. Mass Spectrometry Rev. 1985, 4, 255–293.

Kalechman, Y., et al. The Journal of Immunology. vol. 145, 1512–1517, Sep. 1, 1990.

Isobe, R., et al. "Biomedical and Environmental Mass Spectrometry" vol. 13, 585–594 (1986).

Tsunematsu, H. et al. Biochemical and Biophysical Research Communications, vol. 146, No. 2, 907–911 (1987).

Kodo, H. et. al. The Lancet. Jul. 2, 1988, pp. 38–39.

Blazar, B., et. al. Blood, vol. 74, No. 6, Nov. 1, 1989, pp. 2264–2269.

Tamura, M. et al. Transplantation vol. 51, No. 6, p. 1166–1170 Jun. 1991.

Atkinson, K. et al. Blood, vol. 77, No. 6, Mar. 15, 1991, pp. 1376–1382.

Teshima, H. Exp. Hematol. vol. 17, 1989, pp. 853–858.

Souza, L. M., et al, Science, vol. 232, pp. 61–65 Apr. 4, 1986.

Sheridan, W.P., et al. The Lancet, Oct. 14, 1989, pp. 891–895.

Brandt, S.J. The New England Journal of Medicine, vol. 318, Apr. 7, 1988, pp. 869–876.

Nienhuis, A. W. The Journal of Clinical Investigation. vol. 8, Aug. 1987, pp. 573–577.

Monroy, R.L. Blood. vol. 70, No. 5, Nov. 1987, pp. 1696–1699.

Ende, N. "Life Sciences" vol. 51, pp. 1249–1253, 1992.

Motoki, K. "Radioprotective Effects . . ." Bioorganic and Medicinal Chemistry Letters, vol. 5, No. 22, pp. 2413–2416, 1995.

Hall, Eric. J. "Radiobiology for the Radiologist" Second Ed., Ch. 1, 9 and 11, 1978, Harper and Row—Philadelphia.

Carroll, F.I., et al. J. Med. Chem., 1990, 33: 2501–2508.

Sato, K. et al. High–Performance Tandem Anal. Chem. 1987, 59, 1652–1659.

Y. Kawano et al. "Isolation and Structure of six . . ." Liebigs Annalen Der Chemie, vol. 1.

R. Higuchi et al. Structures of Three New. . . and Pharmaceutical Bulletin, vol. 39. No. 6, Jun. 1991.

K. Munesada, et al. Chem. Soc. Perkin Trans. 1991 p. 189–194.

M. Honda, Chem. Pharm. Bull 39(6) 1385–1391, 1991.

S. Hirsch et al. "New Glycosphingolipids . . ." Tetrahedron, vol. 45. No. 12, Dec. 1989, p. 3898.

Uchida, et al; J. Biochem. 87:1843–1849 (1980).

Yates, et al; Chemical Abstracts 93:112178r (1980).

Dyatlovitskaya, et al; Biokhimiya 49(3):432–436 (1984).

Singh, et al; Molecular & Biochemical Parasitology 26:99–112 (1987).

Inokuchi, et al; Cancer Letters 38:23–30 (1987).

Radin, et al; Biochemical Pharmacology 37(15):2879–2886 (1988).

Hannun, et al; Science 243:500–507 (Jan. 1989).

Kalisiak, et al; Int. J. Cancer 49:837–845 (1991).

Wiegand, et al; Chemical Abstracts 114:122965m (1991).

Dillman, et al; Molecular Biotherapy 4:117–121 (Sep. 1992).

SYNTHESIS OF COMPOUND 9

COMPOUND 9

SYNTHESIS OF COMPOUND 5

COMPOUND 5

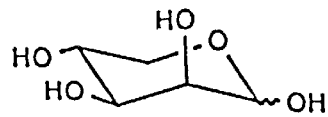
↓ ACETONIDATION
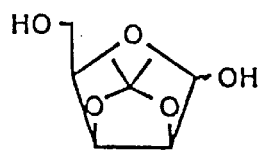
↓ TRITYLATION
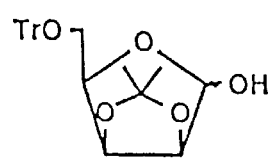
FIG. IIA
↓ WITTIG REACTION
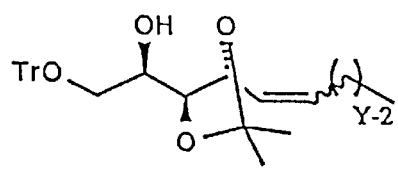
↓ MESYLATION
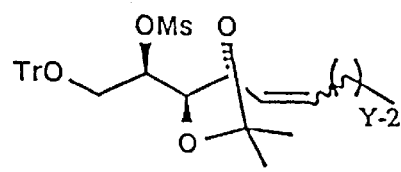
↓ SELECTIVE
 DEPROTECTION

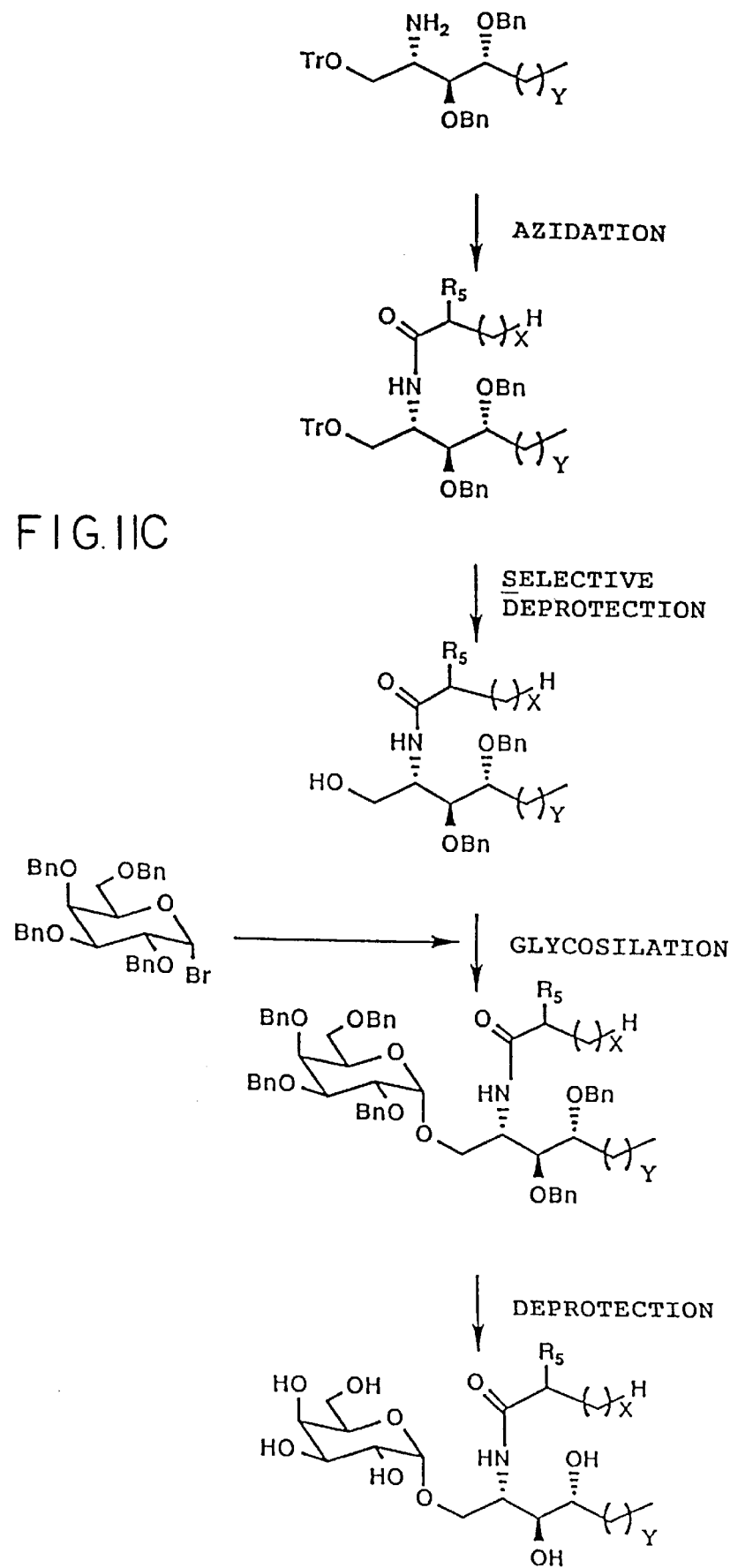
FIG. IIC

αGALACTOSYLCERAMIDE DERIVATIVES

This is a continuation of application Ser. No. 08/148,004 filed on Nov. 5, 1993, abandoned, which is a CIP of Ser. No. 07/876,564 filed Apr. 30, 1992, abandoned.

BACKGROUND OF THE INVENTION

1. Field of the Art

The present invention relates to novel α-galactosylceramides having effective antitumor activity and immuno-stimulating activity, to a process for producing these α-galactosylceramides and to the use thereof.

2. Related Art

In respect to α-galactosylceramide, a study on a mass analysis has been reported in Analytical Chemistry, 59, 1652 (1987), in which the structure of α-galactosylceramide is described. The compound corresponding to the α-galactosylceramide has been isolated from a cestode by B. N. Singh and reported in Molecular and Biochemical Parasitology, 26, 99 (1987). However, the stereo chemical configuration of the sugar is not described in the study, and thus the α-galactosyl structure is not confirmed. In other reports, only two α-galactosylceramides has been extracted and isolated from the marine sponge *Agelas mauritianus* by the present inventors (Japanese Patent Application Nos. 303314/1990 and 244385/1991).

On the other hand, it is only those described in Japanese Patent Laid-Open Publication No. 93562/1989 other than the invention according to the present inventors as far as we know that antitumor activity is found for galactosylceramides. Moreover, all of the galactosylceramides in which antitumor activity is shown in Examples of the above cited specification are β-galactosylceramides, and the dosages are as high as 0.5–2 mg per mouse. Furthermore, there is no example in which a galactosylceramide has been used in practice as an antitumor agent or an immunostimulator.

The galactosylceramides derived from marine sponges are described in Japanese Patent Laid-Open Publication No. 57594/1986 and Pure & Applied Chemistry, 58(3), 387–394 (1980). All of these galactosylceramides are, however, β-galactosylceramides, the antitumor activity of which have not been reported.

In general, the physiological activities of chemical substances depend largely on their chemical structures, and it is always desired to obtain novel compounds having antitumor activity and immuno-stimulating activity.

OUTLINE OF THE INVENTION

The present inventors have extracted specific α-galactosylceramides from a marine sponge *Agelas mauritianus* and found that the compounds exhibit antitumor activity and immuno-stimulating activity. The present inventors have further created the method for synthesizing the related compounds and found that these related compounds also have the similar activities. The present invention have been achieved on the basis of these informations.

That is, the novel α-galactosylceramides according to the present invention are represented by the following formula (A):

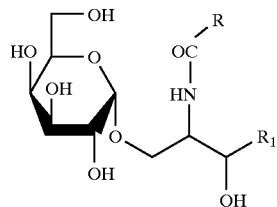

(A)

wherein
R represents

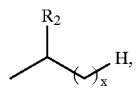

where $R_2$ represents H or OH and X denotes an integer of 0–26, or R represents $-(CH_2)_7CH=CH(CH_2)_7CH_3$ and $R_1$ represents any one of the substituents defined by the following (a)–(e):

(a) $-CH_2(CH_2)_YCH_3$,
(b) $-CH(OH)(CH_2)_YCH_3$,
(c) $-CH(OH)(CH_2)_YCH(CH_3)_2$,
(d) $-CH=CH(CH_2)_YCH_3$, and
(e) $-CH(OH)(CH_2)_YCH(CH_3)CH_2CH_3$, where Y denotes an integer of 5–17.

In the aforementioned formula (A),
(1) the compound in which R represents

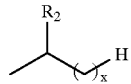

is represented by the formula (I):

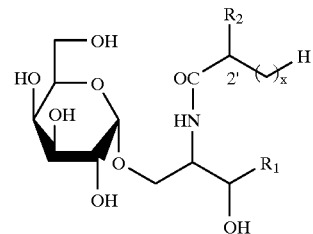

(I)

and (2) the compound in which R represents $-(CH_2)_7CH=CH(CH_2)_7CH_3$ is represented by the formula (XXI):

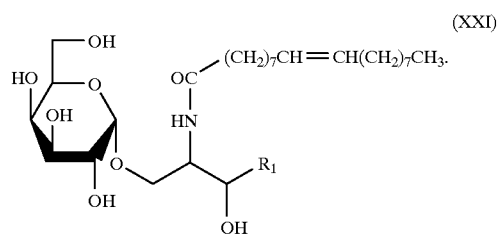

(XXI)

The present invention also relates to a process for preparing the compounds represented by the formula (I) and specified below. That is, the process for preparing the α-galactosylceramide represented by the formula (I) according to the present invention comprises collecting the marine sponge *Agelas mauritianus*, subjecting it to an extraction operation with an organic solvent and isolating from the extract the α-galactosylceramides represented by the formula (I) and specified below:

(1) (2S,3S,4R)-1-(α-D-galactopyranosyloxy)-2-[(R)-2-hydroxytetracosanoylamino]-3,4-heptadecanediol,
(2) (2S,3S,4R)-1-(α-D-galactopyranosyloxy)-2-[(R)-2-hydroxytetracosanoylamino]-3,4-hexadecanediol,
(3) (2S,3S,4R)-1-(α-D-galactopyranosyloxy)-2-[(R)-2-hydroxytricosanoylamino]-16-methyl-3,4-heptadecanediol, and
(4) (2S,3S,4R)-1-(α-D-galactopyranosyloxy)-2-[(R)-2-hydroxypentacosanoylamino]-16-methyl-3,4-octadecanediol.

The compound of the present invention represented by the formula (A) (i.e. formulae (I) and (XXI)) can be also synthesized chemically according to the process schemes or reaction route schemes described below.

The present invention further relates to the use of the compounds represented by the formula (A) (formulae (I) and (XXI)). That is, the antitumor agent and the immunostimulator according to the present invention each contains one or more α-galactosylceramides represented by the formula (A) (formulae (I) and (XXI)) as effective ingredients or contain the effective amount thereof and a pharmaceutically acceptable carrier or diluent.

Furthermore, the present invention relates to the therapeutic method comprising administering the effective amounts of one or more of the aforementioned compounds to patients who need inhibiting the proliferation of tumor or activating immunity.

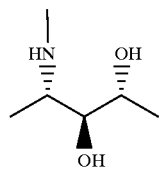

Figure 11B:
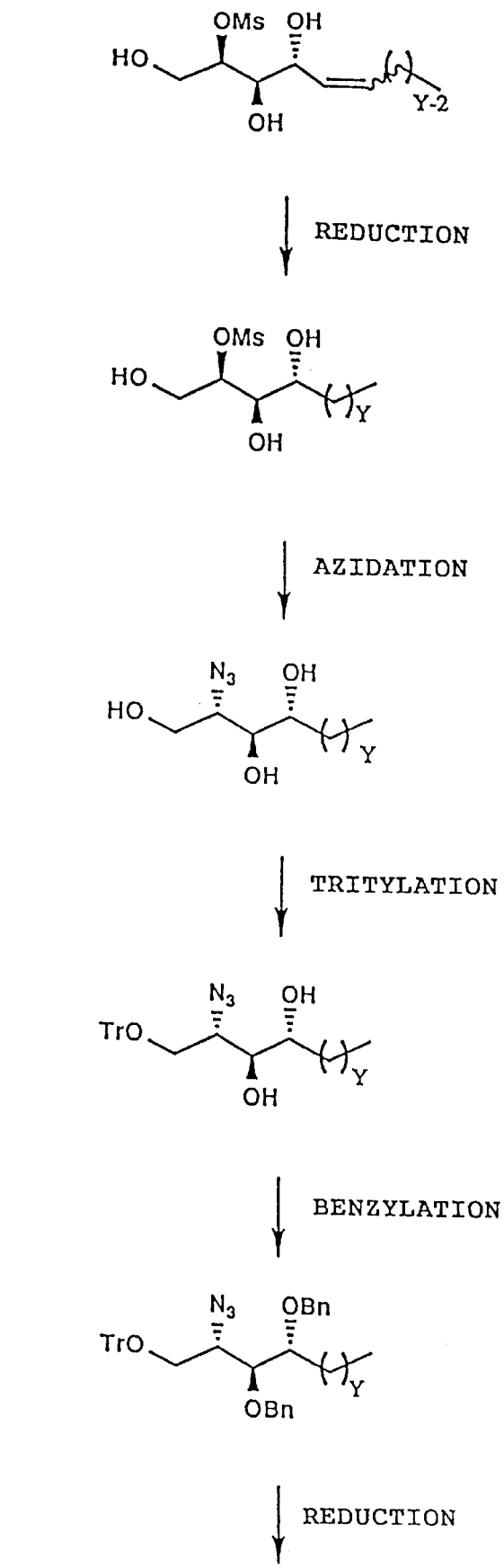
FIG. 11(*a–c*) shows another scheme (synthetic route E) for synthesizing the compounds which can be obtained by synthetic route D and has stereostructure represented by the formula
Figure 12A:
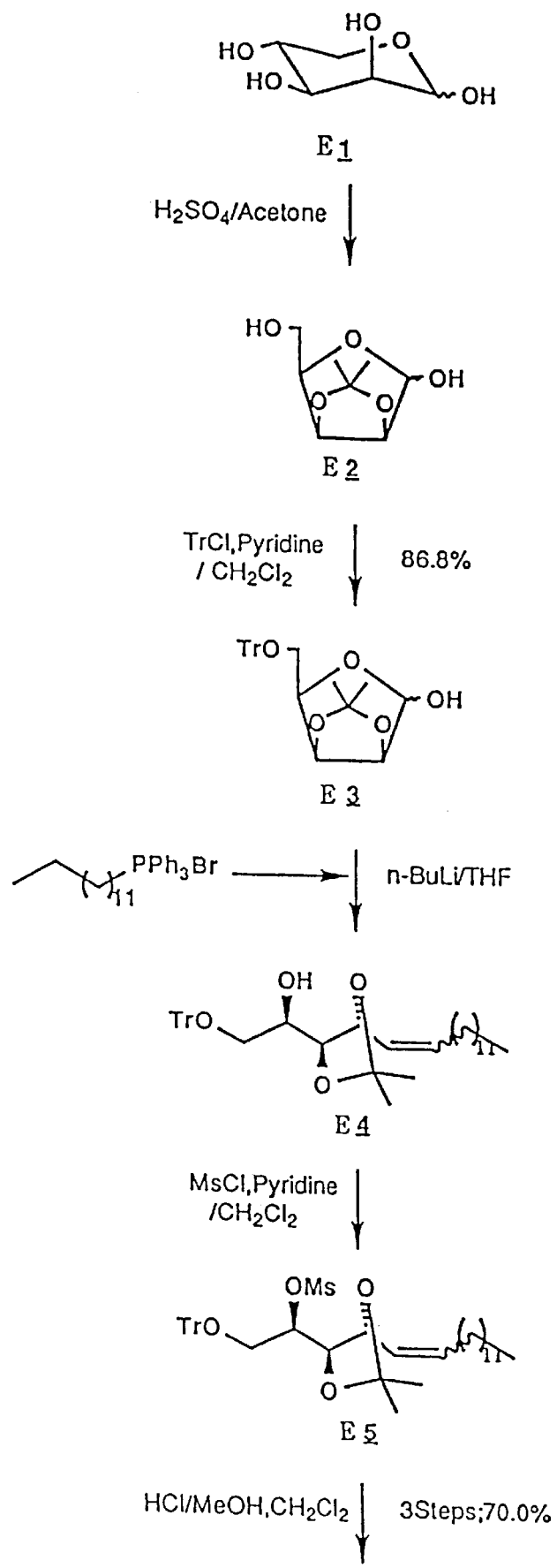
Figure 12B:
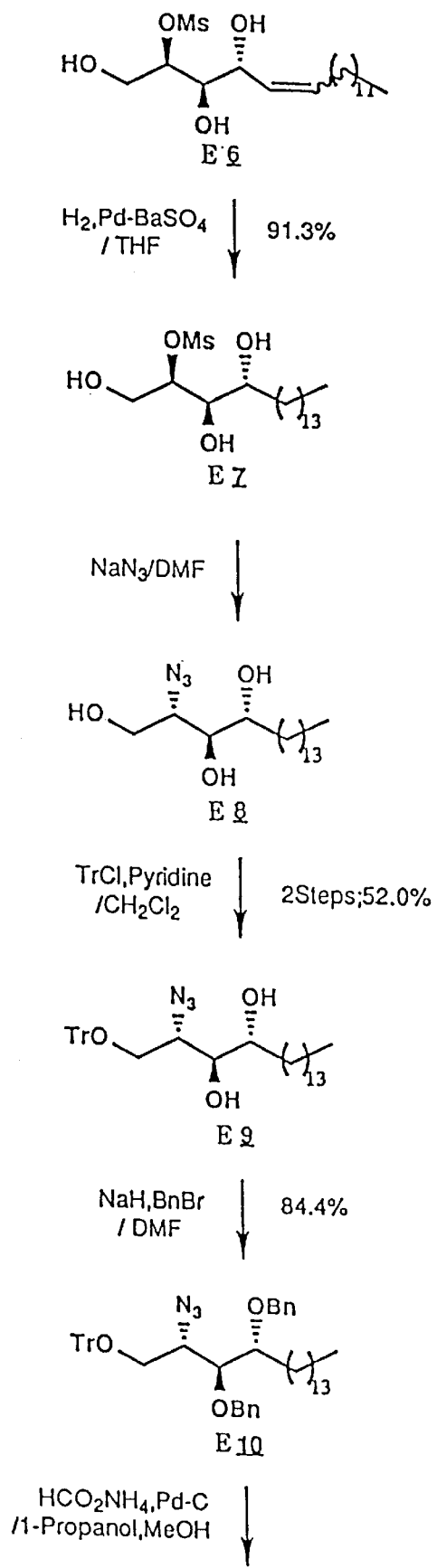
Figure 12C:
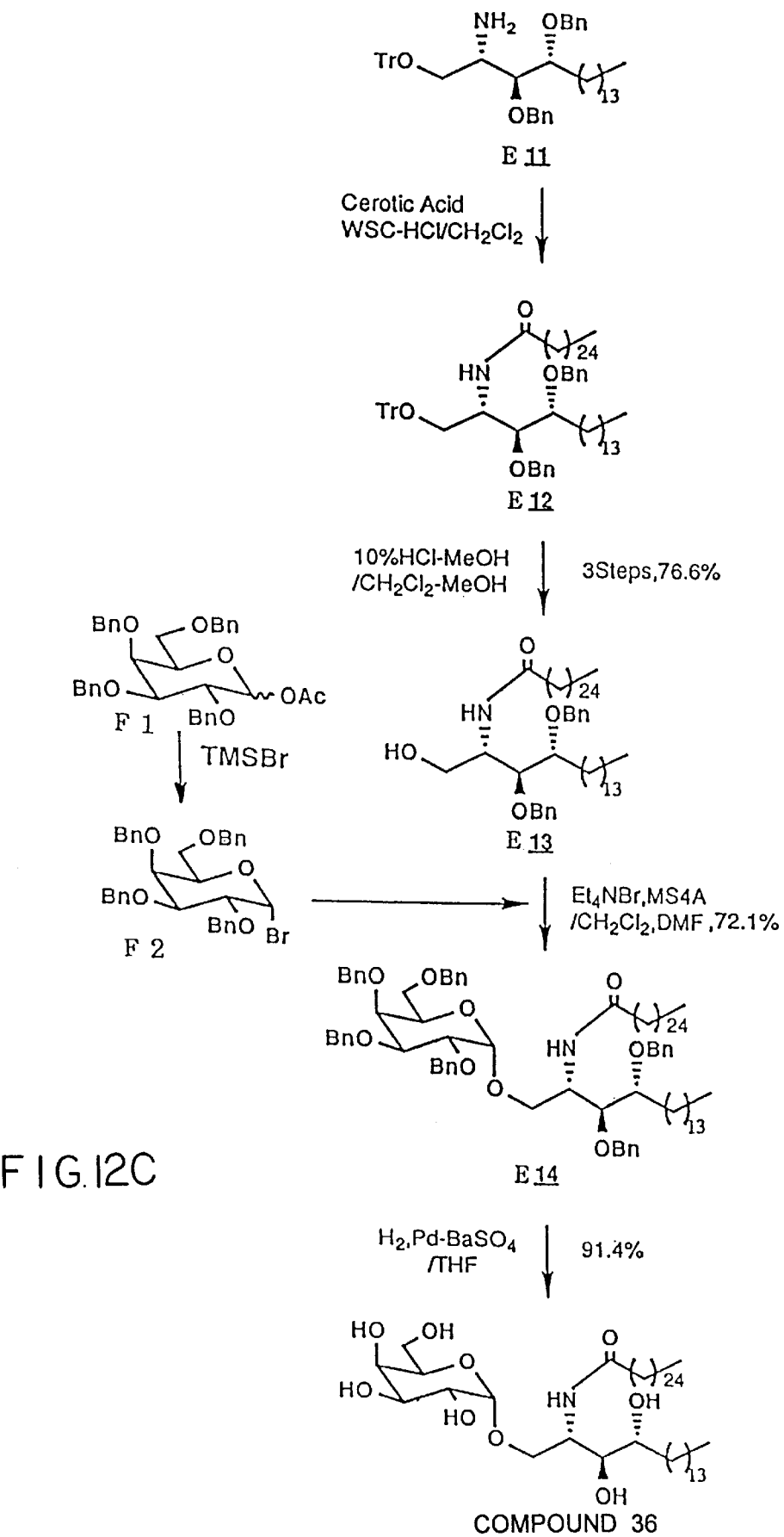

in the long chain base portion as shown, for example, in the last formula in FIG. 11*c*; and FIG. 12(*a–c*) shows the scheme for synthesizing Compound 36, (2S,3S,4R)-1-(α-D-galactopyranosyloxy)-2-hexacosanoylamino-3,4-octadecanediol.

DETAILED DESCRIPTION OF THE INVENTION

α-Galactosylceramides

The α-galactosylceramides according to the present invention, as described above, are represented by the formula (A) (i.e. formulae (I) and (XXI)), and $R_1$ in the formula (I) is preferably represented by the following (a)–(e):

(a) —$CH_2(CH_2)_YCH_3$, wherein, when $R_2$ represents H, it is preferable that X denote an integer of 0–24 and Y denote an integer of 7–15; when $R_2$ represents OH, it is preferable that X denote an integer of 20–24 and Y denote an integer of 11–15; when $R_2$ represents H, it is particularly preferable that X denote an integer of 8–22 and Y denote an integer of 9–13; and when $R_2$ represents OH, it is particularly preferable that X denote an integer of 21–23 and Y denote an integer of 12–14;

(b) —$CH(OH)(CH_2)_YCH_3$, wherein, when $R_2$ represents H, it is preferable that X denote an integer of 18–26 and Y denote an integer of 5–15; when $R_2$ represents OH, it is preferable that X denote an integer of 18–26 and Y denote an integer of 5–17; further when $R_2$ represents H, it is particularly preferable that X denote an integer of 21–25 and Y denote an integer of 6–14; and when $R_2$ represents OH, it is particularly preferable that X denote an integer of 21–25 and Y denote an integer of 6–16;

(c) —$CH(OH)(CH_2)_YCH(CH_3)_2$, wherein when $R_2$ represents H, it is preferable that X denote an integer of 20–24 and Y denote an integer of 9–13; when $R_2$ represents OH, it is preferable that X denote an integer of 18–24 and Y denote an integer of 9–13; further when $R_2$ represents H, it is particularly preferable that X denote an integer of 21–23 and Y denote an integer of 10–12; and when $R_2$ represents OH, it is particularly preferable that X denote an integer of 20–23 and Y denote an integer of 10–12;

(d) —$CH=CH(CH_2)_YCH_3$, wherein $R_2$ represents H and it is preferable that X denote an integer of 10–18 and Y denote an integer of 10–14; and it is particularly preferable that X denote an integer of 11–17 and Y denote an integer of 11–13; and (e) —$CH(OH)(CH_2)_YCH(CH_3)CH_2CH_3$, wherein $R_2$ represents OH and it is preferable that X denote an integer of 21–25 and Y denote an integer of 9–13; and it is particularly preferable that X denote an integer of 22–24 and Y denote an integer of 10–12.

On the other hand, $R_1$ in the formula (XXI) preferably represents —$CH_2(CH_2)_YCH_3$, wherein Y denote preferably an integer of 11–15, particularly 12–14.

A compound of the present invention which has the configurations at 2- and 3-positions as shown in the following formula (II) is particularly preferred.

Furthermore, when the synthetic route described below is used, the α-galactosylceramide represented by the formula (IV) hereinafter wherein X denote an integer of 8–22 and Y denote an integer of 9–13 is the most preferred from the standpoint of easy availability of the raw material.

The more concrete form and the preferred form of the compound of the present invention represented by the formula (A) (formulae (I) and (XXI)) can be defined by the following definitions (1)–(4):

(1) the α-galactosylceramides of the formula (I) represented by the formula (II):

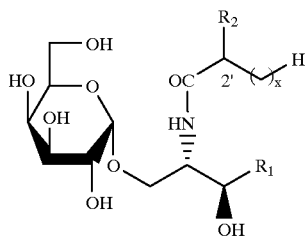

wherein $R_1$ represents any one of the substituents defined by the following (a)–(e), $R_2$ represents H or OH and X is defined in the following (a)–(e);

(a) —$CH_2(CH_2)_YCH_3$,
wherein, when $R_2$ represents H, X denotes an integer of 0–24 and Y denotes an integer of 7–15; and when $R_2$ represents OH, X denotes an integer of 20–24 and Y denotes an integer of 11–15;

(b) —$CH(OH)(CH_2)_YCH_3$,
wherein when $R_2$ represents H, X denotes an integer of 18–26 and Y denotes an integer of 5–15; and when $R_2$ represents OH, X denotes an integer of 18–26 and Y denotes an integer of 5–17;

(c) —$CH(OH)(CH_2)_YCH(CH_3)_2$,
wherein when $R_2$ represents H, X denotes an integer of 20–24 and Y denotes an integer of 9–13; and when $R_2$ represents OH, X denotes an integer of 18–24 and Y denotes an integer of 9–13;

(d) —$CH=CH(CH_2)_YCH_3$,
wherein $R_2$ represents H, X denotes an integer of 10–18 and Y denotes an integer of 10–14; and (e) —$CH(OH)(CH_2)_YCH(CH_3)CH_2CH_3$,
wherein $R_2$ represents OH, X denotes an integer of 21–25 and Y denotes an integer of 9–13;

(2) the α-galactosylceramides of the formula (I) represented by the formula (III):

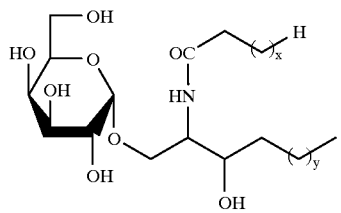

wherein X denotes an integer of 0–24 and Y denotes an integer of 7–15;

(3) the α-galactosylceramides described in the above (2), wherein more preferably X denotes an integer of 8–22 and Y denotes an integer of 9–13;

(4) the α-galactosylceramides described in the above (2) which is more preferably represented by the formula (IV):

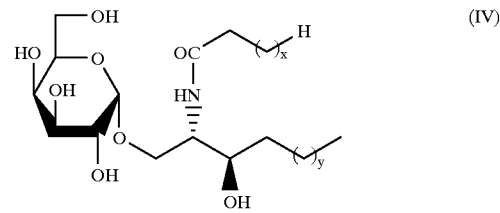

wherein X denotes an integer of 0–24 and Y denotes an integer of 7–15;

(5) the α-galactosylceramides described in the above (4), wherein most preferably X denotes an integer of 8–22 and Y denotes an integer of 9–13;

(6) the α-galactosylceramides of the formula (I) represented by the formula (V):

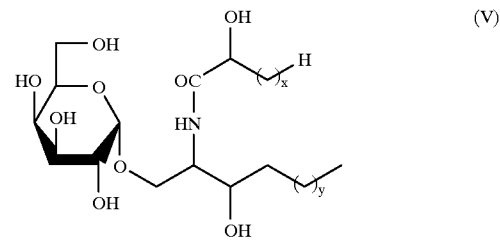

wherein X denotes an integer of 20–24 and Y denotes an integer of 11–15;

(7) the α-galactosylceramides described in the above (6), wherein more preferably X denotes an integer of 21–23 and Y denotes an integer of 12–14;

(8) the α-galactosylceramides described in the above (6), represented more preferably by the formula (VI):

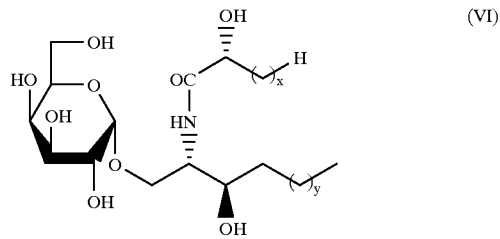

wherein X denotes an integer of 20–24 and Y denotes an integer of 11–15;

(9) the α-galactosylceramides described in the above (8), wherein most preferably X denotes an integer of 21–23 and Y denotes an integer of 12–14;

(10) the α-galactosylceramides of the formula (I) represented by the formula (VII):

(VII)

[structure VII]

wherein X denotes an integer of 18–26 and Y denotes an integer of 5–15;

(11) the α-galactosylceramides described in the above (10), wherein more preferably X denotes an integer of 21–25 and Y denotes an integer of 6–14;

(12) the α-galactosylceramides described in the above (10) which is represented more preferably by the formula (VIII):

[structure VIII]

wherein X denotes an integer of 18–26 and Y denotes an integer of 5–15;

(13) the α-galactosylceramides described in the above (12), wherein most preferably X denotes an integer of 21–25 and Y denotes an integer of 6–14;

(14) the α-galactosylceramides of the formula (I) represented by the formula (IX):

[structure IX]

wherein X denotes an integer of 18–26 and Y denotes an integer of 5–17;

(15) the α-galactosylceramides described in the above (14), wherein more preferably X denotes an integer of 21–25 and Y denotes an integer of 6–16;

(16) the α-galactosylceramides described in the above (14) represented more preferably by the formula (X):

[structure X]

wherein X denotes an integer of 18–26 and Y denotes an integer of 5–17;

(17) the α-galactosylceramides described in the above (14) represented more preferably by the formula (X'):

[structure X']

wherein X denotes an integer of 20–24 and Y denotes an integer of 10–14;

(18) the α-galactosylceramides described in the above (16), wherein more preferably X denotes an integer of 21–25 and Y denotes an integer of 6–16;

(19) the α-galactosylceramides described in the above (17), wherein most preferably X denotes an integer of 21–23 and Y denotes an integer of 11–13;

(20) the α-galactosylceramides of the formula (I) represented by the formula (XI):

[structure XI]

wherein X denotes an integer of 20–24 and Y denotes an integer of 9–13;

(21) the α-galactosylceramides described in the above (20), wherein more preferably X denotes an integer of 21–23 and Y denotes an integer of 10–12;

(22) the α-galactosylceramides described in the above (20) more preferably represented by the formula (XII):

[structure XII]

wherein X denotes an integer of 20–24 and Y denotes an integer of 9–13;

(23) the α-galactosylceramides described in the above (22), wherein more preferably X denotes an integer of 21–23 and Y denotes an integer of 10–12;

(24) the α-galactosylceramides of the formula (I) represented by the formula (XIII):

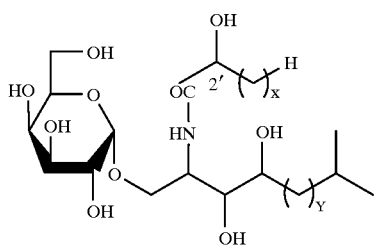

(XIII)

wherein X denotes an integer of 18–24 and Y denotes an integer of 9–13;

(25) the α-galactosylceramides described in the above (24), wherein more preferably X denotes an integer of 20–23 and Y denotes an integer of 10–12;

(26) the α-galactosylceramides described in the above (24), more preferably represented by the formula (XIV):

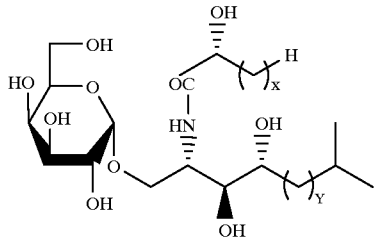

(XIV)

wherein X denotes an integer of 19–23 and Y denotes an integer of 9–13;

(27) the α-galactosylceramides described in the above (24), more preferably represented by the formula (XIV'):

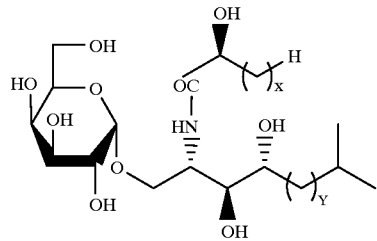

(XIV')

wherein X denotes an integer of 20–24 and Y denotes an integer of 9–14;

(28) the α-galactosylceramides described in the above (26), wherein most preferably X denotes an integer of 20–22 and Y denotes an integer of 10–12;

(29) the α-galactosylceramides described in the above (27), wherein most preferably X denotes an integer of 21–23 and Y denotes an integer of 10–12;

(30) the α-galactosylceramides of the formula (I) represented by the formula (XV):

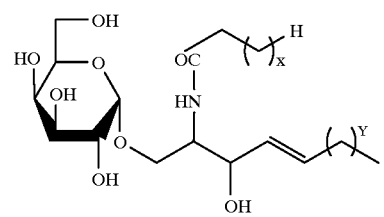

(XV)

wherein X denotes an integer of 10–18 and Y denotes an integer of 10–14;

(31) the α-galactosylceramides described in the above (30), wherein more preferably X denotes an integer of 11–17 and Y denotes an integer of 11–13;

(32) the α-galactosylceramides described in the above (30) more preferably represented by the formula (XVI):

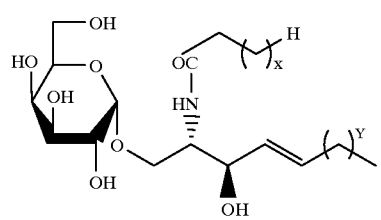

(XVI)

wherein X denotes an integer of 10–18 and Y denotes an integer of 10–14;

(33) the α-galactosylceramides described in the above (32), wherein most preferably X denotes an integer of 11–17 and Y denotes an integer of 11–13;

(34) the α-galactosylceramides of the formula (I) represented by the formula (XVII):

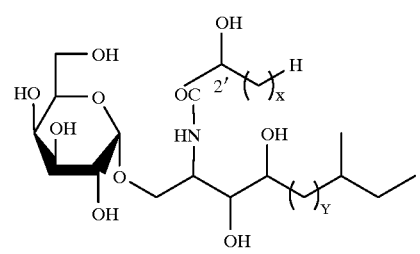

(XVII)

wherein X denotes an integer of 21–25 and Y denotes an integer of 9–13;

(34) the α-galactosylceramides described in the above (34), wherein more preferably X denotes an integer of 22–24 and Y denotes an integer of 10–12;

(36) the α-galactosylceramides described in the above (34) more preferably represented by the formula (XVIII):

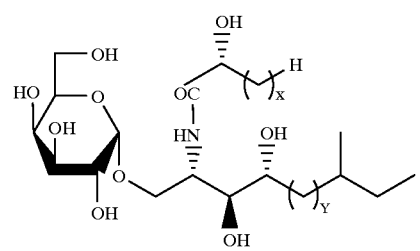

(XVIII)

wherein X denotes an integer of 21–25 and Y denotes an integer of 9–13;

(37) the α-galactosylceramides described in the above (36), wherein most preferably X denotes an integer of 22–24 and Y denotes an integer of 10–12;

(38) the α-galactosylceramides of the formula (XXI) represented by the formula (XIX):

$$\text{(XIX)}$$

wherein Y denotes an integer of 11–15;

(39) the α-galactosylceramides described in the above (38), wherein more preferably Y denotes an integer of 12–14;

(40) the α-galactosylceramide described in the above (38) more preferably represented by the formula (XX):

$$\text{(XX)}$$

wherein Y denotes an integer of 11–15; and

(41) the α-galactosylceramides described in the above (40), wherein most preferably Y denotes an integer of 12–14.

Concrete preferred examples of compounds included in the present invention represented by the formula (A) (formula (I) and (XXI)) are shown below. In respective formulae, X and Y are defined as above.

(1) The compounds represented by the following formulae (III) and (VI)

$$\text{(III)}$$

$$\text{(VI)}$$

Compound 1:
  (2S,3R)-1-(α-D-galactopyranosyloxy)-2-tetracosanoylamino-3-octadecanol, Compound 2:
  (2S,3R)-2-docosanoylamino-1-(α-D-galactopyranosyloxy)-3-octadecanol, Compound 3:
  (2S,3R)-1-(α-D-galactopyranosyloxy)-2-eicosanoylamino(icosanoylamino)-3-octadecanol, Compound 4:
  (2S,3R)-1-(α-D-galactopyranosyloxy)-2-octadecanoylamino-3-octadecanol, Compound 5:
  (2S,3R)-1-(α-D-galactopyranosyloxy)-2-tetradecanoylamino-3-octadecanol, Compound 6:
  (2S,3R)-2-decanoylamino-1-(α-D-galactopyranosyloxy)-3-octadecanol, Compound 7:
  (2S,3R)-1-(α-D-galactopyranosyloxy)-2-octanoylamino-3-octadecanol, Compound 8:
  (2S,3R)-2-acetamino-1-(α-D-galactopyranosyloxy)-3-octadecanol, Compound 9:
  (2S,3R)-1-(α-D-galactopyranosyloxy)-2-tetracosanoylamino-3-tetradecanol, Compound 10:
  (2S,3R)-1-(α-D-galactopyranosyloxy)-2-tetradecanoylamino-3-hexadecanol, Compound 11:
  (2R,3S)-1-(α-D-galactopyranosyloxy)-2-tetradecanoylamino-3-hexadecanol, Compound 12:
  (2S,3S)-1-(α-D-galactopyranosyloxy)-2-tetradecanoylamino-3-hexadecanol, Compound 13:
  (2R,3R)-1-(α-D-galactopyranosyloxy)-2-tetradecanoylamino-3-hexadecanol, Compound 14:
  (2S,3R)-1-(α-D-galactopyranosyloxy)-2-[(R)-2-hydroxytetracosanoylamino]-3-octadecanol.

Among these compounds, the compounds 1–10 and 14 are preferred in consideration of the configuration at 2- and 3-positions.

(2) The compounds represented by the following formula (XVI)

$$\text{(XVI)}$$

Compound 15:
  (2S,3R,4E)-1-(α-D-galactopyranosyloxy)-2-octadecanoylamino-4-octadecen-3-ol, Compound 35:
  (2S,3R,4E)-1-(α-D-galactopyranosyloxy)-2-tetradecanoylamino-4-octadecen-3-ol.

(3) The compounds represented by the following formula (VIII)

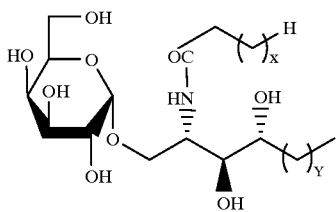
(VIII)

Compound 16:
  (2S,3S,4R)-1-(α-D-galactopyranosyloxy)-2-tetracosanoylamino-3,4-octadecanediol,
Compound 17:
  (2S,3S,4R)-1-(α-D-galactopyranosyloxy)-2-tetracosanoylamino-3,4-heptadecanediol,
Compound 18:
  (2S,3S,4R)-1-(α-D-galactopyranosyloxy)-2-tetracosanoylamino-3,4-pentadecanediol,
Compound 19:
  (2S,3S,4R)-1-(α-D-galactopyranosyloxy)-2-tetracosanoylamino-3,4-undecanediol,
Compound 20:
  (2S,3S,4R)-1-(α-D-galactopyranosyloxy)-2-hexacosanoylamino-3,4-heptadecanediol,
Compound 36:
  (2S,3S,4R)-1-(α-D-galactopyranosyloxy)-2-hexacosanoylamino-3,4-octadecanediol, and
Compound 37:
  (2S,3S,4R)-1-(α-D-galactopyranosyloxy)-2-octacosanoylamino-3,4-heptadecanediol.

(4) The compounds represented by the following formulae (X) and (X')

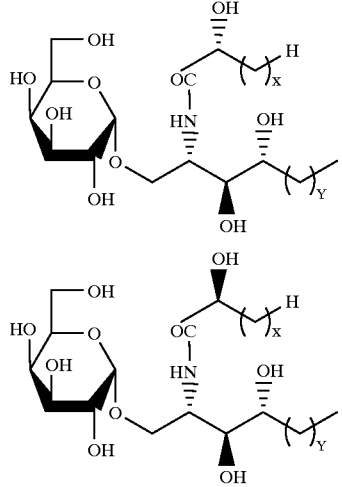

Compound 21:
  (2S,3S,4R)-1-(α-D-galactopyranosyloxy)-2-[(R)-2-hydroxytetracosanoylamino]-3,4-octadecanediol,
Compound 22:
  (2S,3S,4R)-1-(α-D-galactopyranosyloxy)-2-[(R)-2-hydroxytetracosanoylamino]-3,4-heptadecanediol,
Compound 23:
  (2S,3S,4R)-1-(α-D-galactopyranosyloxy)-2-[(R)-2-hydroxytetracosanoylamino]-3,4-pentadecanediol,
Compound 24:
  (2S,3S,4R)-1-(α-D-galactopyranosyloxy)-2-[(R)-2-hydroxytetracosanoylamino]-3,4-undecanediol,
Compound 25:
  (2S,3S,4R)-1-(α-D-galactopyranosyloxy)-2-[(R)-2-hydroxyhexacosanoylamino]-3,4-octadecanediol,
Compound 26:
  (2S,3S,4R)-1-(α-D-galactopyranosyloxy)-2-[(R)-2-hydroxyhexacosanoylamino]-3,4-nonadecanediol,
Compound 27:
  (2S,3S,4R)-1-(α-D-galactopyranosyloxy)-2-[(R)-2-hydroxyhexacosanoylamino]-3,4-eicosanediol (icosanediol),
Compound 28:
  (2S,3S,4R)-1-(α-D-galactopyranosyloxy)-2-[(S)-2-hydroxytetracosanoylamino]-3,4-heptadecanediol,
Compound 32:
  (2S,3S,4R)-1-(α-D-galactopyranosyloxy)-2-[(R)-2-hydroxytetracosanoylamino]-3,4-hexadecanediol.

(5) The compounds represented by the following formulae (XII), (XIV) and (XIV')

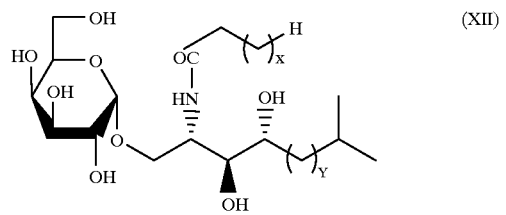
(XII)

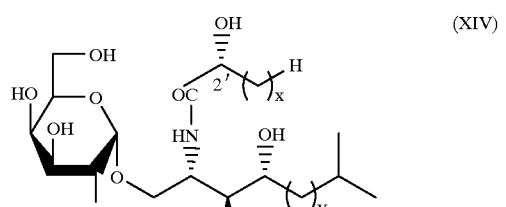
(XIV)

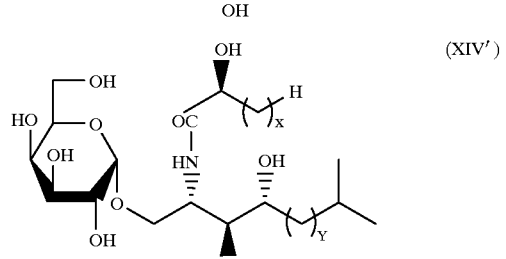
(XIV')

Compound 30:
  (2S,3S,4R)-1-(α-D-galactopyranosyloxy)-2-[(S)-2-hydroxytetracosanoylamino]-16-methyl-3,4-heptadecanediol,
Compound 31:
  (2S,3S,4R)-1-(α-D-galactopyranosyloxy)-16-methyl-2-tetracosanoylamino-3,4-heptadecanediol,
Compound 33:
  (2S,3S,4R)-1-(α-D-galactopyranosyloxy)-2-[(R)-2-hydroxytricosanoylamino]-16-methyl-3,4-heptadecanediol.

(6) The compound represented by the following formula (XVIII)

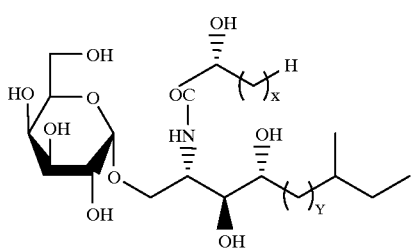

Compound 34:
(2S,3S,4R)-1-(α-D-galactopyranosyloxy)-2-[(R)-2-hydroxypentacosanoylamino]-16-methyl-3,4-octadecanediol.

(7) The compound represented by the following formula (XIX)

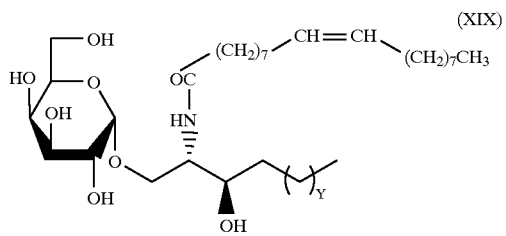

Compound 29:
(2S,3R)-1-(α-D-galactopyranosyloxy)-2-oleoylamino-3-octadecanol.

Process for preparing the compounds of the present invention (i) Process for obtaining the compounds from a marine sponge Among the compounds represented by the formula (I), the α-galactosylceramides such as the compounds 22, 32, 33 and 34 can be obtained by extraction from some sponges with an organic solvent.

Fundamentally the process for obtaining the compounds from marine sponges comprises A: a step for collecting the sponges, B: an extraction step for contacting the sponges with at least one appropriate organic solvent in order to obtain a crude extract containing the compound of the present invention, and C: a step for isolating the compound of the present invention from the crude extract obtained in the step B.

(Step A)
This step is one for collecting marine sponges.
A preferred example of a species of marine sponges is *Agelas mauritianus*, which can be collected from the sea of Kumeshima in Okinawa Prefecture of Japan.

(Step B)
This step is one for extracting the compound of the present invention as a crude extract from the sponge with at least one appropriate organic solvent or water.

An organic solvent is preferable as the extracting solvent. It is sufficient that an appropriate organic solvent for extraction is a solvent which can extract the compound of the present invention from the sponge. Preferred examples of the solvent are esters such as ethyl acetate and butyl acetate and so on; alcohols such as methanol, ethanol and isopropyl alcohol and so on; aliphatic hydrocarbons such as heptane, hexane and isooctane and so on; ketones such as acetone and methyl ethyl ketone and so on; aromatic compounds such as benzene and toluene and so on; ethers such as diethyl ether and t-butyl methyl ether and so on; and substituted lower aliphatic hydrocarbon compounds such as methylene chloride, chloroform and 1,2-dichloroethane and so on. In the present invention, these solvents can be used respectively alone or in combination of the two or more thereof.

Among the organic solvents mentioned above, more preferable examples are ethanol, acetone, ethyl acetate and the like, and the preferred examples of combination of a plurality of the solvents are methanol and chloroform, methanol and methylene chloride, acetone and toluene and the like.

As the method for extraction, well-known methods in relation to the extraction of physiologically active substances, particularly a glycosphingolipid, from a living material such as an animal or a plant or a microorganism, for example, the methods described in Liebigs Annalen der Chemie, 51, (1990); Tetrahedron, 45 (12), 3897, (1989); or Zeitschrift fuer Naturforschung Teil B, 42 (11), 1476 (1987) can be applied. These extraction methods can be used respectively alone or in combination of the two or more thereof.

Specifically, for example, a marine sponge is applied as it is or after the preliminary treatments such as homogenization and lyophilization, and the extraction operation is carried out preferably with stirring at a temperature of 0°–80° C., preferably around room temperature for an extraction period of 1–72 hours, preferably 12–36 hours. If necessary, the aforementioned extraction operation can be repeated at desired times.

(Step C)
This step is one for isolating the compound of the present invention from the crude extract which is obtained in the step B and contains the compound of the present invention.

As the isolating method, well-known methods in relation to the fractionation and isolation of a physiologically active substances, particularly a glycosphingolipids, from a variety of living materials as described above can be used. The general descriptions concerning such a method are given for example in Liebigs Annalen der Chemie 51, (1990).

More specifically, as the fractionation method, the examples include fractionating method with use of the difference of solubilities (for example, by the combination of water and methanol), distributing method (involving the countercurrent distribution method; for example, by the combination of ethylacetate and water) with use of the difference of distribution rates, and the like. The aforementioned crude extract can be treated by these fractionation methods to recover the objective fraction, and thus the aforementioned four compounds of the present invention can be obtained as the crude products.

In order to further purify the resulting crude products of the compounds of the present invention, the combination of the aforementioned fractionation methods with the isolating methods as described below may be carried out at desired times. If necessary, the purified product of the compound of the present invention can also be obtained by subjecting the crude extract obtained in the step B to an appropriate operation of an isolating method at necessary times.

The examples of such isolating methods are the methods for eluting the objective product by chromatography such as adsorption chromatography, distribution chromatography, thin layer chromatography, high performance liquid chromatography or gel filtration and the like. A concrete example of chromatography is the column chromatography in which a stationary phase such as silica gel, ODS, TOYOPEARL HW-40 (TOSO, Japan) or Sephadex LH-20 (Pharmacia, Fine Chemicals) is employed, and as a mobile phase an organic solvent as described above in the paragraph of the step B or water is used alone or in combination of the two or more thereof. As the preferable concrete examples of the eluent, mentioned are methanol, chloroform and the like as the single eluent, and methanol and chloroform, methanol and water and the like as the mixture.

(ii) Process by chemical synthesis

While the compounds according to the present invention, that is, the α-galactosylceramides represented by the formula (A) (formulae (I) and (XXI)) can be derived from a variety of the chemical modifications of sphingosine, they can be also prepared by the overall synthesis with the chemical synthetic means which is a combination of a variety of general chemical reactions required for the synthesis of the glycosphingolipids. The route of the overall synthesis is not the only one, and the α-galactosylceramide can be prepared via an alternative route from a different starting material. It can be also synthesized, for example, by applying the method described in Agricultural and Biological Chemistry, 54 (3), 663, 1900 which is an example of the chemical synthetic means. It can be also synthesized, for example, for applying the method described in Liebigs Annalen der Chemie, 663, 1988 which is an example of using a variety of sugars as the starting materials. Although a protective group is removed after a sugar is bonded to a ceramide in these synthetic methods, it is also possible to use the method for synthesizing a cerebroside in which a sugar is first bonded to a long chain base and an amino group is then introduced to form an amide, as described in Liebigs Annalen der Chemie, 663, 1988.

(Synthetic route A)

Figure 1A:
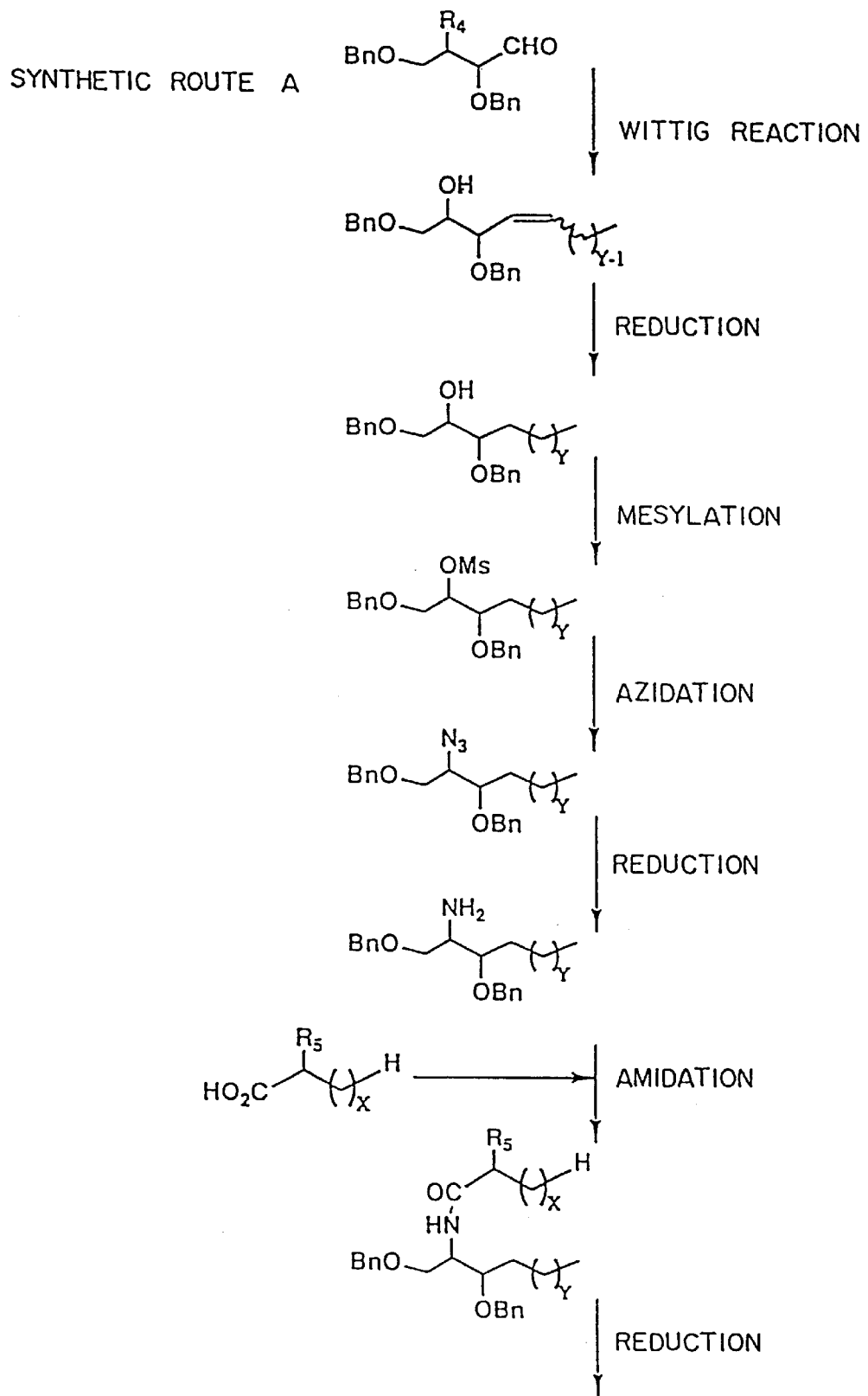
FIG. 1 (*a* and *b*) shows the scheme (synthetic route A) for synthesizing the compounds represented by the formula (A) from an aldehyde compound as a starting material.
Figure 1B:
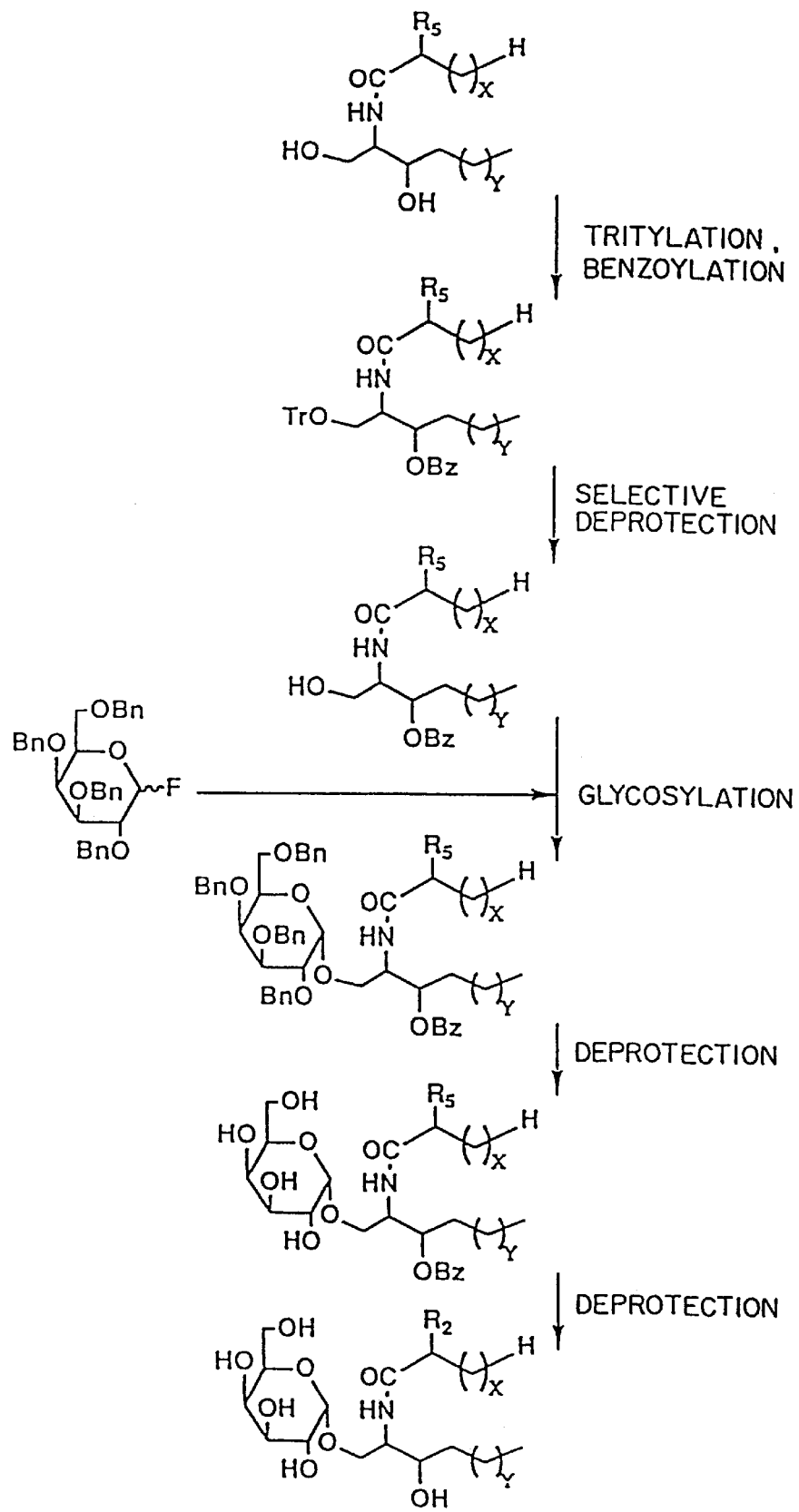

As an example of the synthesis as described above, the compounds represented by the formulae (III), (V) and (XIX) can be synthesized also via the following steps (cf. FIGS. 1$a$ and 1$b$).

In FIG. 1, the following abbreviations are used:
Bn: benzyl,
$R_4$: a hydroxyl group or a formyloxy group,
Ms: methanesulfonyl,
$R_5$: a hydrogen atom or an acyloxy group,
Tr: triphenylmethyl, and
Bz: benzoyl.

An aldehyde as a raw material has one or two asymmetric centers. An amino acid or a sugar can also be employed as the asymmetric sources. While a benzyl group is employed as the protective group of a hydroxyl group in this example, any appropriate groups such as an isopropylidene group may be also employed.

In this route scheme, particularly many reaction methods are known for the amidation. An acid chloride or an acid anhydride can also be employed in place of a carboxylic acid.

The reaction with a carboxylic acid is a condensation reaction in the presence of an appropriate condensation agent. Suitable condensation agent used herein are dicyclohexylcarbodiimide (DCC), 2-ethoxy-1-ethoxycarbonyl-1,2-dihydroquinoline (EEDQ), 1-ethyl-3-(3-dimethylaminopropyl)-carbodiimide (WSC), chlorocarbonates, onium salts and the like. In order to progress the reaction rapidly, an organic base such as triethylamine, pyridine, N-methylmorpholine, dimethylaniline, 4-dimethylaminopyridine, N-methylpiperidine or N-methylpyrrolidine is added. Any inert solvents which do not participate in the reaction may be used as the solvent.

The reaction with an acid chloride satisfactorily proceeds generally in the presence of a solvent. Although the reaction is generally conducted with use of an appropriate solvent, the reaction which proceeds slowly can be progressed rapidly in the absence of the solvent. Any inert solvents which do not participate in the reaction may be used as the solvent. If the reaction proceeds slowly, it may be progressed rapidly by the addition of an organic solvent such as triethylamine, pyridine, N-methylmorpholine, dimethylaniline or 4-dimethylaminopyridine.

The reaction with an acid anhydride is preferably conducted in the presence of an appropriate base. As the base herein used, triethylamine, pyridine or the like is usually used as the solvent concurrently.

Many methods of reaction for glycosylation are also known as described in the following references: (1) YUKI GOSEI KAGAKU, 38 (5), 473, 1980; (2) YUKI GOSEI KAGAKU, 41 (8), 701, 1983; (3) Pure and Applied Chemistry, 61 (7), 1257, 1989; (4) Pharmacia, 27 (1), 50, 1991.

Any of the reactions described above may be used, but a method for obtaining preferentially an α-galactoside such as the one described in Chemistry Letters, 431–432, 1981 is preferred. If the α-isomer is not obtained alone, its separation from the β-isomer is carried out. When such a separation is difficult, the α-isomer and the β-isomer can be separated by introducing the hydroxyl group into an acyl derivative (e.g. an acetyl derivative).

(Synthetic route B)

Figure 2:
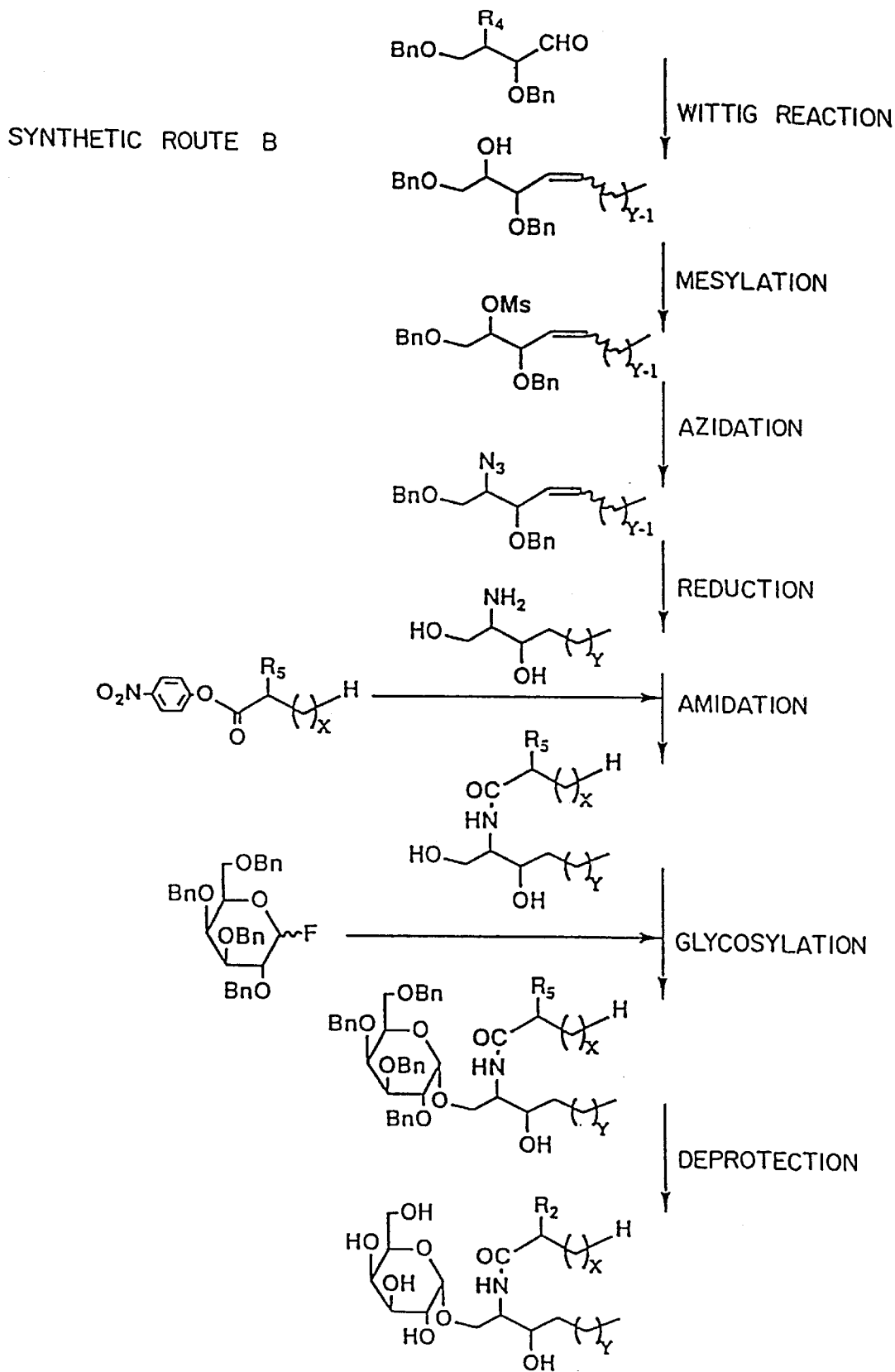
FIG. 2 also shows the scheme (synthetic route B) which is a route for synthesizing the compounds represented by the formula (A) from an aldehyde compound as a starting material as well as FIG. 1 and has less steps than the reaction route A.

It is also possible to show the following scheme as a shorter process starting from the same raw material as in the synthetic route A. The compounds represented by the formulae (III), (V) and (XIX) can be synthesized also by this method (see FIG. 2). In FIG. 2, the same abbreviations as described above are used. This route is characterized in that the steps are successively reduced by performing simultaneously the reduction of the azide group, the removal of the benzyl group and the reduction of the double bond. The four isomers of the 2-amino-1,3-alkanediol which are intermediates obtained by the reduction can be obtained alone, respectively, by selecting the asymmetric sources of the aldehyde as the starting material depending on the purposes. The isomers are individually subjected to the subsequent amidation. A variety of the methods as described in the route A can be employed in this step. Subsequently, glycosylation and deprotection can be conducted in the similar way to the route A to obtain the objective product.

(Synthetic route C)

Figure 3:
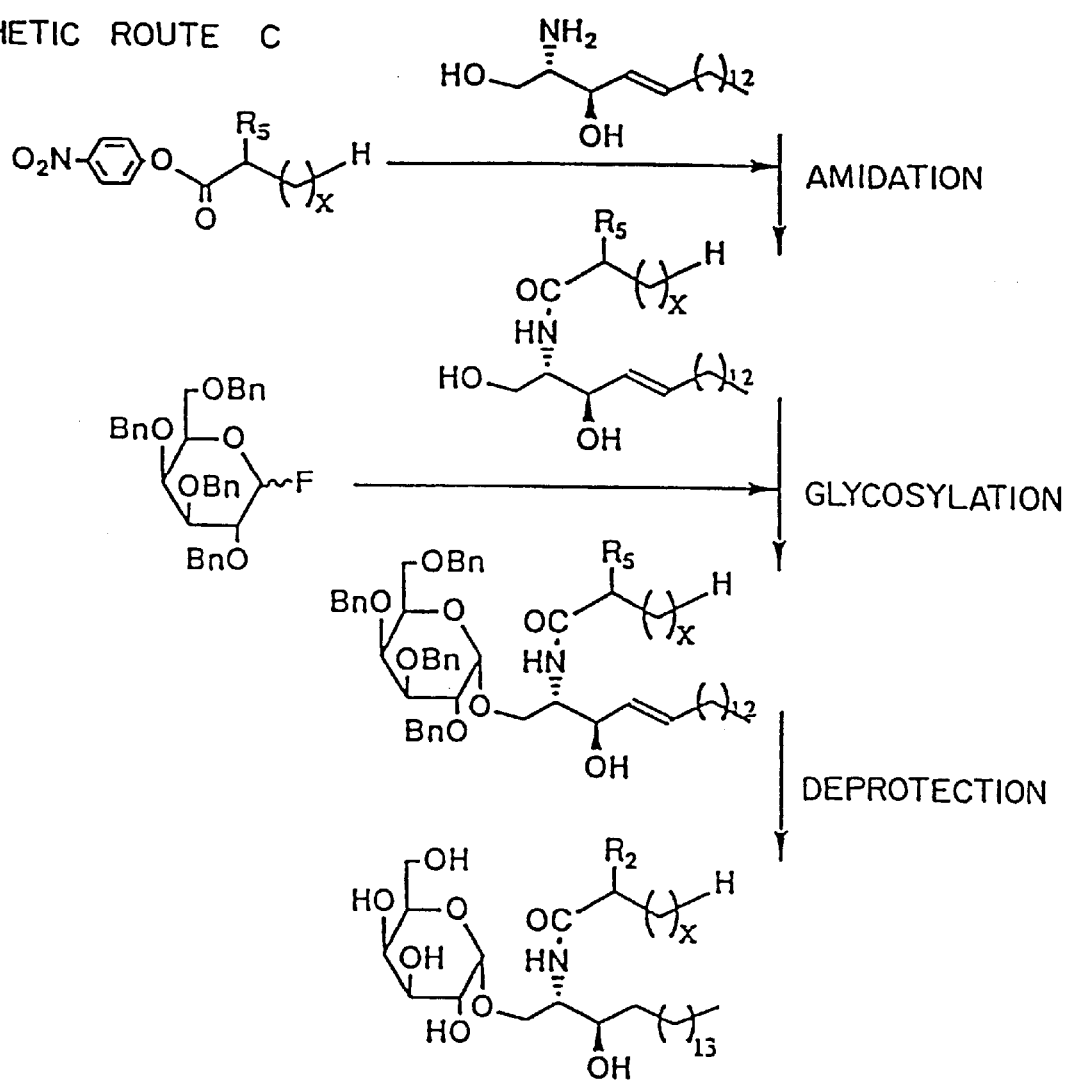
FIG. 3 shows the scheme (synthetic route C) for deriving the compounds represented by the formula (A) by applying a variety of chemical modifications to the sphingosine.

As an example of the synthesis introduced by a variety of chemical modifications of sphingosine, the compounds represented by the formulae (IV), (VI), (XVI) and (XX) in which the long chain base portion has 18 carbon atoms can be also synthesized via the following process (see FIG. 3). In FIG. 3, the same abbreviations as described above are used. While sphingosine can be obtained by the extraction from natural materials, it is commercially available from Sigma Chemical Company or Funakoshi Corporation, Japan. It can be also synthesized by a variety of synthetic methods as described in Pharmacia, 27, 1164, 1991 or Journal of the Chemical Society Perkin Transaction 1, 2279, 1991. The isomers having steric configurations different from those of the natural materials can be also synthesized by applying the method described in Helvetica Chimica Acta, 40, 1145, 1957 or Journal of the Chemical Society, Chemical Communications, 820, 1991. In the latter reference, many examples of the synthesis are reported. In this route, the double bond can be left also after the glycosylation. That is, if catalytic reduction is employed, a compound having no double bond is obtained, and if metallic sodium is reacted in liquid ammonia, a compound retaining a double bond is produced. Thus, it is possible to prepare the products suitable for the purpose.

(Synthetic route D)

Figure 4A:
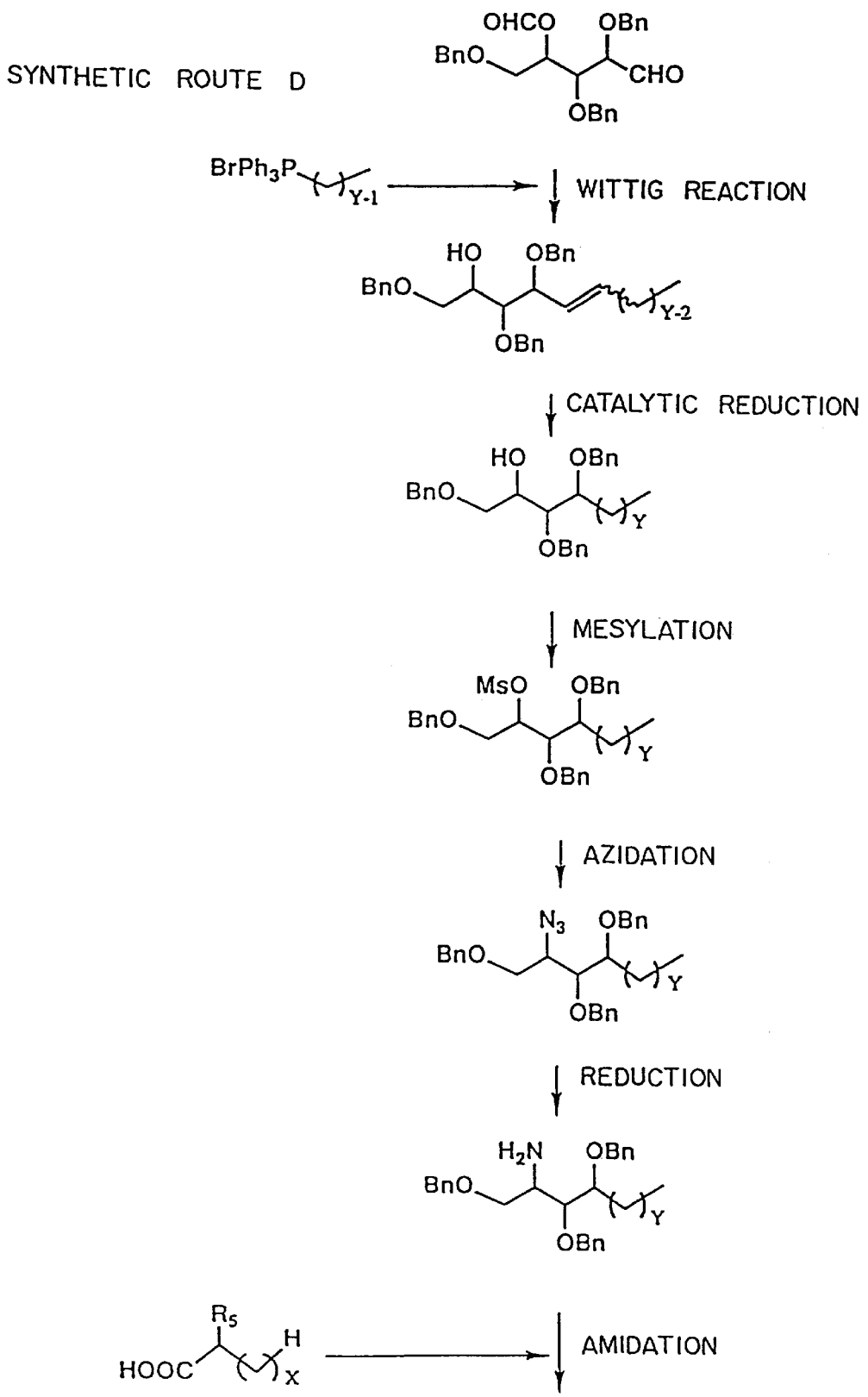
FIG. 4(*a–c*) shows the scheme (synthetic route D) for synthesizing a derivative of the compound represented by the formula (A) from an aldehyde compound as a starting material, which has a hydroxyl group at the C-4 of the long chain base.
Figure 4B:
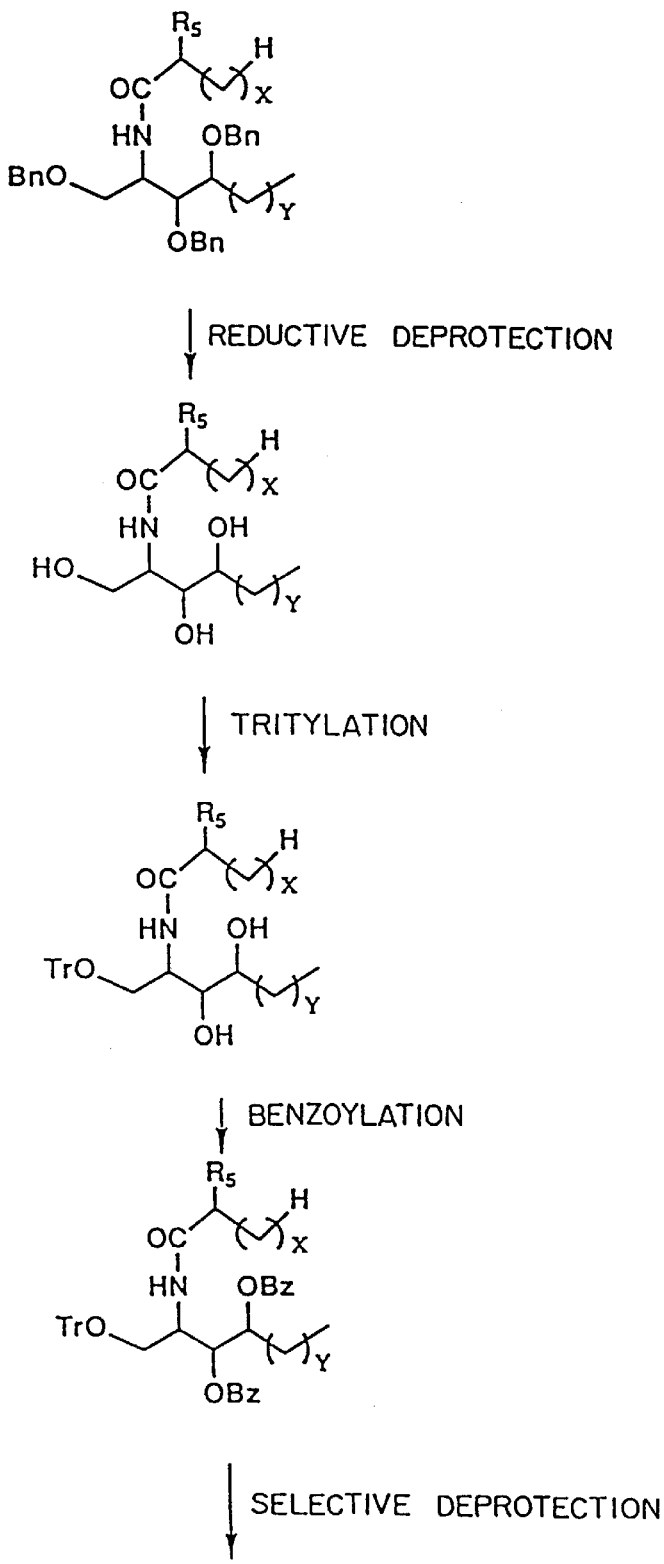
Figure 4C:
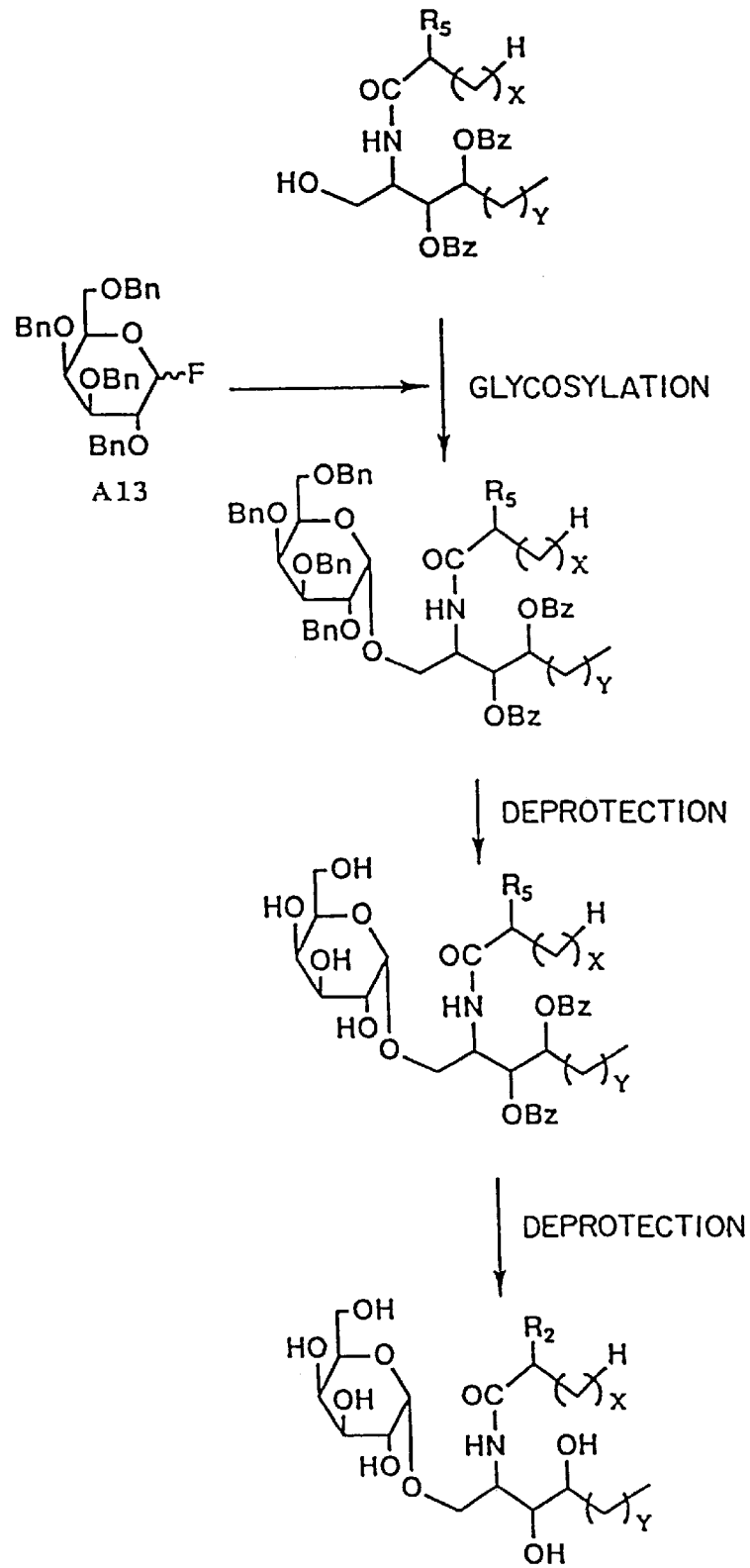

Furthermore, the compounds represented by the formulae (VII), (IX), (XI), (XIII) and (XVII) among the compounds represented by the formula (A) in which the long chain base has a hydroxyl group at C-4 can also be synthesized via the following process (see FIGS. 4a–4c). In FIG. 4, the same abbreviations as described above are used.

The starting aldehyde can be obtained alone as any isomers by selecting appropriately the asymmetric source of a raw material. The isomers are separately subjected to the subsequent Wittig reaction. The terminal of the Wittig's salts can be easily formed into the iso type, the anteiso type or the straight chain type. Generally, the Wittig reaction with such unstable ylid give a compound having a cis-double bond as main product, which is however contaminated by the trans-isomer. The double bonds in the mixture are however reduced to a single bond during the step of the catalytic reduction, and thus the mixture will cause no problem as it is. By subsequent mesylation and azide inversion, the product is reduced to an amino derivative, which is amidated in the subsequent step to give a ceramide. The intermediate ceramide having protective groups is also obtained by protecting a commercially available Cerebrine E (Alfred Bader Chemicals or K&K Laboratories Inc.) as the raw material with any appropriate protective group. Furthermore, in order to discriminate the hydroxyl group to which the sugar is bonded, protection and selective deprotection followed by glycosylation and deprotection can be conducted to obtain the objective product (see FIGS. 4a–4c).

(Synthetic Route E)

The compounds which are long-chain bases having a hydroxyl group at the 4-position thereof and are represented by the formulae (VIII), (X), (X'), (XII), (XIV), (XIV') or (XVIII) can also be synthesized via the following stages. (See FIGS. 11a to 11c). The abbreviations used in the figures have the same meanings as in the above-described route. This route is characterized in that commercially available D-lyxose is used as a starting compound.

Lyxose in which the 2- and 3-positions are protected by acetonide and the 5-position by a trityl group is subjected to the Wittig reaction as in the route D, and mesylation, deprotection, catalytic reduction and azide inversion are conducted. After protecting groups are introduced, they are reduced to amino groups, and azidation is conducted to obtain a ceramide. A desired compound can be obtained by subjecting the ceramide to selective deprotection, followed by glycosylation and deprotection.

The use of the compounds of the present invention

The compounds of the present invention represented by the formula (A) (formula (I) and (XXI)) have the following physiological activities, that is, an antitumor activity and an immuno-stimulating activity and can be used as an antitumor agent and an immunostimulator.

(1) Antitumor activity

The compounds of the present invention exhibited antitumor activities against the B16 mouse melanoma cells inoculated s.c. in mouse as shown in Experimental Example 2 below.

(2) Immuno-stimulating activity

The compounds of the present invention exhibited the stimulating effect on mixed lymphocyte culture reaction (MLR) in the test of mouse MLR as described in Experimental Example 3 below.

(3) Antitumor agent and immuno-stimulatory agent

As described above, the compound of the present invention has the antitumor activity and the immuno-stimulating activity and can be employed as an antitumor agent and an immunostimulator.

While the compounds of the present invention may be employed alone, these compounds may be used also in combination with the chemotherapy or the radiotherapy. Their uses have been reviewed in Pharmaceutical Society of Japan, Pharmacia Review, No. 23, Chemistry for Controlling Cancer, Second Series, 105–113, 1097; Medicalview Co., Ltd., Illustrative Clinic, "Cancer" series No. 19, GAN TO MENEKI, 159–169, 1987; IGAKU NO AYUMI, 150 (14), 1018–1021, 1989.

Since the compounds of the present invention exhibit such an immuno-stimulating activity as described above, they are also employed as an immunostimulator against disorders other than cancer such as various infectious diseases, acquired immunodeficiency syndrome (AIDS) or the like. These uses have been described as the general in Medicalview Co., Ltd., Illustrative Clinic, "Cancer" series No. 19, GAN TO MENEKI, 45–50, 1987 and RINSHO KAGAKU, 23 (10), 1299–1305, 1987.

The compounds of the present invention as an antitumor agent and the immunostimulator can be administered via any appropriate dosage route in drug form determined by the dosage route adopted. As the drug, it takes generally a form which is diluted and molded with a pharmaceutically acceptable additive (carrier or diluent). When the compounds of the present invention are used as antitumor agent or immunostimulator, they can be administered orally or parenterally to human or mammal. For example, the compound of the present invention can be administered by dissolving, suspending or emulsifying it in an appropriate solvent for injection (e.g. distilled water for injection) and injecting it intravenously, intramuscularly or subcutaneously. If necessary, polysorbates or polyethylene glycols can be added as solubilizing agents. The compound of the present invention can be administered orally by adding an appropriate additive (e.g. any compounds which are usually used for this purpose such as starch, lactose, crystalline cellulose, hydroxypropylcellulose (HPC), calcium carboxymethylcellulose (CMC-Ca), magnesium stearate and the like) and forming the mixture into powder, tablet, granule, capsule, troche, dry syrup or the like.

The dose of the compound of the present invention is determined to ensure that the dose administered continuously or intermittently will not exceed a certain amount in consideration of the results in test animals and the individual conditions of a patient. A specific dose naturally varies depending on the dosage procedure, the conditions of a patient or a subject animal such as age, body weight, sex, sensitivity, feed, dosage period, drugs used in combination, seriousness of the patient or the disease, and the appropriate dose and dosage times under the certain conditions must be determined by the test for determining the appropriate dose by a medical specialist based on the above-described indices. In this connection, the minimal dose required for developing the activity of the compound of the present invention is generally in the range of ca. 0.0001 mg–100 mg per 1 kg of the body weight of a host.

EXPERIMENTAL EXAMPLES

The present invention will now be described in detail with reference to Experimental Examples, but it should not be construed that the invention be limited to these Experimental Examples.

Experimental Example 1-A

Preparation from a natural material
Preparation of the compounds 22, 32, 33 and 34:

The sponge *Agelas mauritianus* collected from the sea of Kumeshima in Okinawa Prefecture of Japan was subjected to homogenization and lyophilization to give a product (1,077.6 g). It was extracted with methanol-chloroform (1:1) as the first solvent to give an extract, which was then concentrated under reduced pressure to give a residue (178.53 g). The residue was distributed between ethyl acetate as the first distribution solvent and water. The upper ethyl acetate layer was dried over sodium sulfate anhydrous, and the lower aqueous layer was extracted with 1-butanol. The ethyl acetate soluble fractions and the 1-butanol soluble fractions containing the compounds 32, 33, 22 and 34 were combined together and concentrated under reduced pressure to give a residue (125.22 g), which was washed with 30% aqueous methanol and extracted with methanol. The extract was concentrated under reduced pressure to give a brown solid product in the yield of 37.50 g. The solid product was applied to silica gel column chromatography (Wako Gel C-200), and separated by eluting with chloroform initially and then with chloroform-methanol with gradually increasing the ratio of methanol. Eluent with chloroform containing 5%–8% methanol afforded an active fraction (20.05 g), which was further extracted with methanol and concentrated under reduced pressure to give a brown solid product. The solid product was applied to a ODS column (YMC-ODS-A) and washed with 30% aqueous methanol and then eluted with methanol to give an active fraction (1.2127 g), which was applied to reversed phase high performance liquid chromatography (Rp-HPLC) on a YMC-D-ODS-5 (manufactured from K.K. YMC) detected with an RI detector, eluting with 100% methanol at 11 ml/min flow rate to afford the compounds of the present invention 32 (24.0 mg), 33 (29.5 mg), 22 (20.9 mg) and 34 (9.8 mg) at the retention times of 39, 41, 46 and 74 minutes, respectively.

The compounds 32, 33, 22 and 34 have the following spectral data:

Compound 32

$[\alpha]^{28}_D$=+61.6° (1-PrOH, c=1.0)

MS: negative FABMS 816.

IR: (cm$^{-1}$, KBr) 3400, 2950, 2870, 1645, 1535, 1475, 1080.

mp: 193.5°–195.0° C.

NMR: $^1$H (500 MHz, $C_5D_5N$; 27° C.)

δ (ppm) 8.49 (1H, d, J=9.2 Hz), 7.53 (1H, bs), 7.04 (1H, bs), 6.71 (1H, d, J=6.7 Hz), 6.68 (1H, bs), 6.52 (1H, bs), 6.32 (1H, bs), 6.09 (1H, d, J=6.1 Hz), 5.58 (1H, d, J=3.7 Hz), 5.26 (1H, m), 4.62 (2H, m), 4.57 (1H, m), 4.52 (1H, bs), 4.48 (2H, m) 4.37 (1H, m), 4.34 (2H, m), 4.32 (1H, m), 4.26 (1H, m), 2.28 (1H, m), 2.18 (1H, m), 1.98 (1H, m), 1.87 (2H, m), 1.73 (1H, m), 1.66 (2H, m), 1.10–1.46 (56H, m), 0.85 (6H, t, J=7.3 Hz).

$^{13}$C (125 MHz, $C_5D_5N$; 27° C.)

δ (ppm) 175.0 (s), 101.2 (d), 76.5 (d), 73.0 (d), 72.4 (d), 72.3 (d), 71.6 (d), 70.9 (d), 70.1 (d), 68.1 (t), 62.6 (t), 50.4 (d), 35.5 (t), 34.4 (t), 32.1 (t), 30.3 (t), 30.1 (t), 30.0 (t), 29.9 (t), 29.5 (t), 26.4 (t), 25.8 (t), 22.9 (t), 14.2 (q).

Compound 33

$[\alpha]^{28}_D$=+65.4° (1-PrOH, c=1.0)

MS: negative FABMS 830.

IR: (cm$^{-1}$, KBr) 3400, 2950, 2870, 1645, 1535, 1475, 1080.

mp: 203.0°–205.0° C.

NMR: $^1$H (500 MHz, $C_5D_5N$; 27° C.)

δ (ppm) 8.49 (1H, d, J=9.2 Hz), 7.53 (1H, bs), 7.04 (1H, bs), 6.71 (1H, d, J=6.7 Hz), 6.68 (1H, bs), 6.52 (1H, bs), 6.32 (1H, bs), 6.09 (1H, d, J=6.1 Hz), 5.58 (1H, d, J=3.7 Hz), 5.26 (1H, m), 4.62 (2H, m), 4.57 (1H, m), 4.51 (1H, bs), 4.48 (2H, m), 4.36 (1H, m), 4.33 (3H, m), 4.25 (1H, m), 2.29 (1H, m), 2.18 (1H, m), 1.99 (1H, m), 1.88 (2H, m), 1.73 (1H, m), 1.66 (2H, m), 1.46 (2H, m), 1.10–1.42 (53H, m), 0.84 (9H, m).

$^{13}$C (125 MHz, $C_5D_5N$; 27° C.)

δ (ppm) 175.0 (s), 101.2 (d), 76.5 (d), 73.1 (d), 72.4 (d), 72.4 (d), 71.6 (d), 70.9 (d), 70.2 (d), 68.2 (t), 62.6 (t), 50.6 (d), 39.2 (t), 35.5 (t), 34.4 (t), 32.1 (t), 30.3 (t), 30.1 (t), 30.0 (t), 29.8 (t), 29.7 (t), 29.5 (t), 28.2 (d), 27.8 (t), 27.4 (t), 26.4 (t), 25.8 (t), 23.0 (t), 22.8 (q), 14.2 (q).

Compound 22

$[\alpha]^{28}_D$=+69.2° (1-PrOH, c=1.0)

MS: negative FABMS 830.

IR: (cm$^{-1}$, KBr) 3400, 2950, 2870, 1645, 1535, 1475, 1080.

mp: 201.0°–203.5° C.

NMR: $^1$H (500 MHz, $C_5D_5N$; 27° C.)

δ (ppm) 8.48 (1H, d, J=9.2 Hz), 7.53 (1H, bs), 7.03 (1H, bs), 6.71 (1H, d, J=6.7 Hz), 6.67 (1H, bs), 6.53 (1H, bs), 6.32 (1H, bs), 6.09 (1H, bs), 5.59 (1H, d, J=3.7 Hz), 5.27 (1H, m), 4.63 (2H, m), 4.58 (1H, m), 4.52 (1H, bs), 4.47 (2H, m), 4.38 (1H, m), 4.32 (3H, m), 4.26 (1H, m), 2.27 (1H, m), 2.18 (1H, m), 1.98 (1H, m), 1.88 (2H, m), 1.73 (1H, m), 1.65 (2H, m), 1.10–1.46 (58H, m), 0.85 (6H, t, J=7.3 Hz).

$^{13}$C (125 MHz, $C_5D_5N$; 27° C.)

δ (ppm) 175.0 (s), 101.2 (d), 76.5 (d), 73.0 (d), 72.4 (d), 72.3 (d), 71.6 (d), 70.9 (d), 70.2 (d), 68.3 (t), 62.6 (t), 50.4 (d), 35.5 (t), 34.4 (t), 32.1 (t), 30.3 (t), 30.1 (t), 29.9 (t), 29.6 (t), 29.5 (t), 26.4 (t), 25.9 (t), 22.9 (t), 14.2 (q).

Compound 34

$[\alpha]^{28}_D$=+59.4° (1-PrOH, c=1.0)

MS: negative FABMS 872.

IR: (cm$^{-1}$, KBr) 3400, 2950, 2870, 1645, 1535, 1475, 1080.

mp: 215.5°–218.0° C.

NMR: $^1$H (500 MHz, $C_5D_5N$; 27° C.)

δ (ppm) 8.50 (1H, d, J=9.2 Hz), 7.53 (1H, bs), 7.02 (1H, bs), 6.71 (1H, d, J=6.7 Hz), 6.66 (1H, bs), 6.52 (1H, bs), 6.31 (1H, bs), 6.09 (1H, d, J=3.9 Hz), 5.59 (1H, d, J=3.7 Hz), 5.27 (1H, m), 4.62 (2H, m), 4.58 (1H, m), 4.52 (1H, bs), 4.47 (2H, m), 4.38 (1H, m), 4.33 (3H, m), 4.26 (1H, m), 2.28 (1H, m), 2.18 (1H, m), 1.99 (1H, m), 1.87 (2H, m), 1.73 (1H, m), 1.66 (2H, m), 1.10–1.42 (61H, m), 0.85 (9H, m).

$^{13}$C (125 MHz, $C_5D_5N$; 27° C.)

δ (ppm) 175.0 (s), 101.2 (d), 76.5 (d), 73.0 (d), 72.4 (d), 72.3 (d), 71.6 (d), 70.9 (d), 70.1 (d), 68.2 (t), 62.6 (t), 50.5 (d), 36.8 (t), 35.5 (t), 34.5 (d), 34.4 (t), 32.0 (t), 30.3 (t), 30.3 (t), 30.1 (t), 30.0 (t), 29.8 (t), 29.7 (t), 29.5 (t), 27.3 (t), 26.4 (t), 25.8 (t), 22.9 (t), 19.3 (q), 14.2 (q), 11.5 (q).

Experimental Example 1-B

Preparation by the synthetic methods

The methods for synthesizing the compounds of the present invention and the physico-chemical properties thereof are shown below (see reaction route schemes 1–10).

(1) Synthetic route A

Figure 5A:
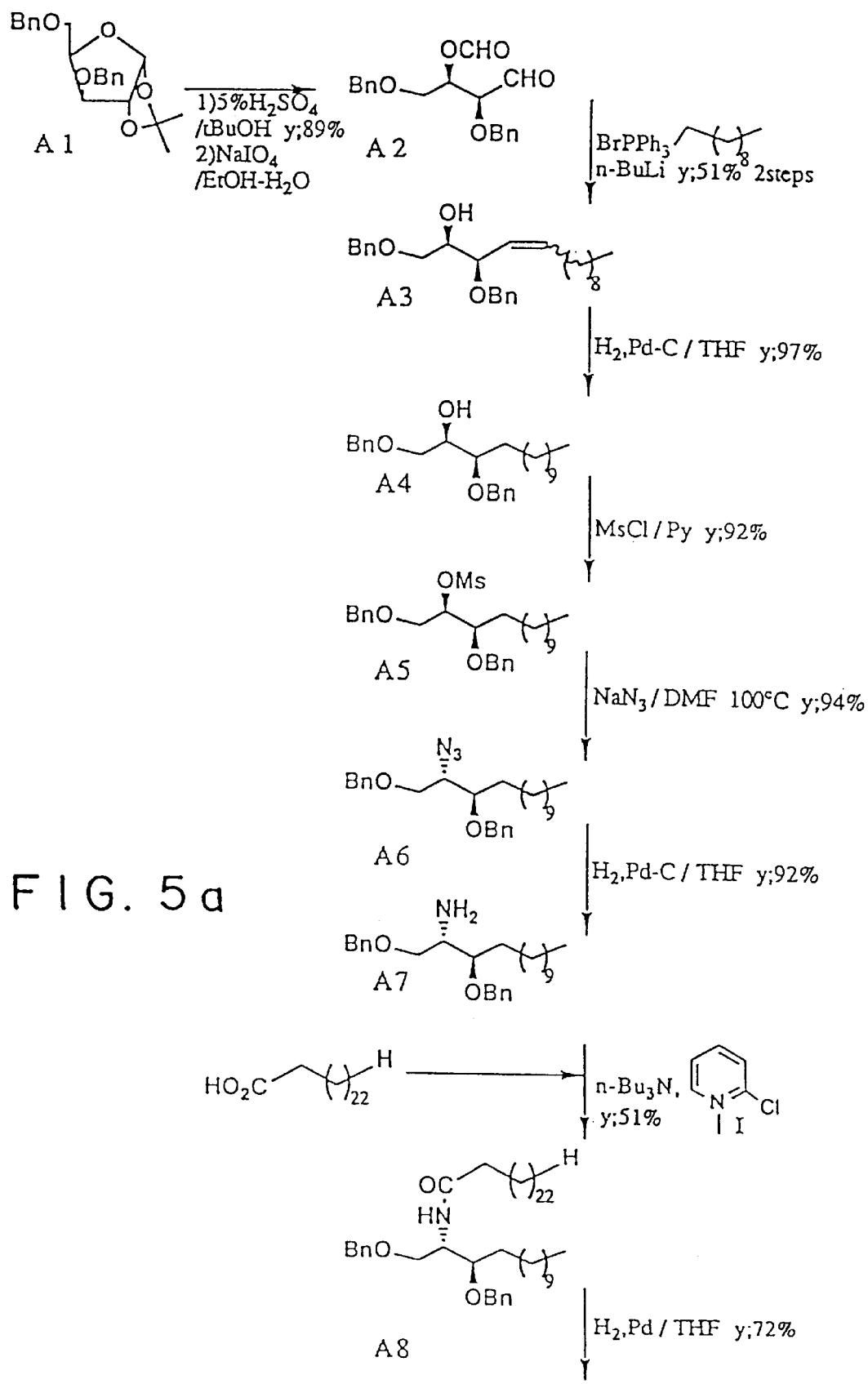
FIG. 5(*a* and *b*) shows the scheme which illustrates a preferred method for synthesizing the compound 9 ((2S,3R)-1-(α-D-galactopyranosyloxy)-2-tetracosanoylamino-3-tetradecanol)
Figure 5B:
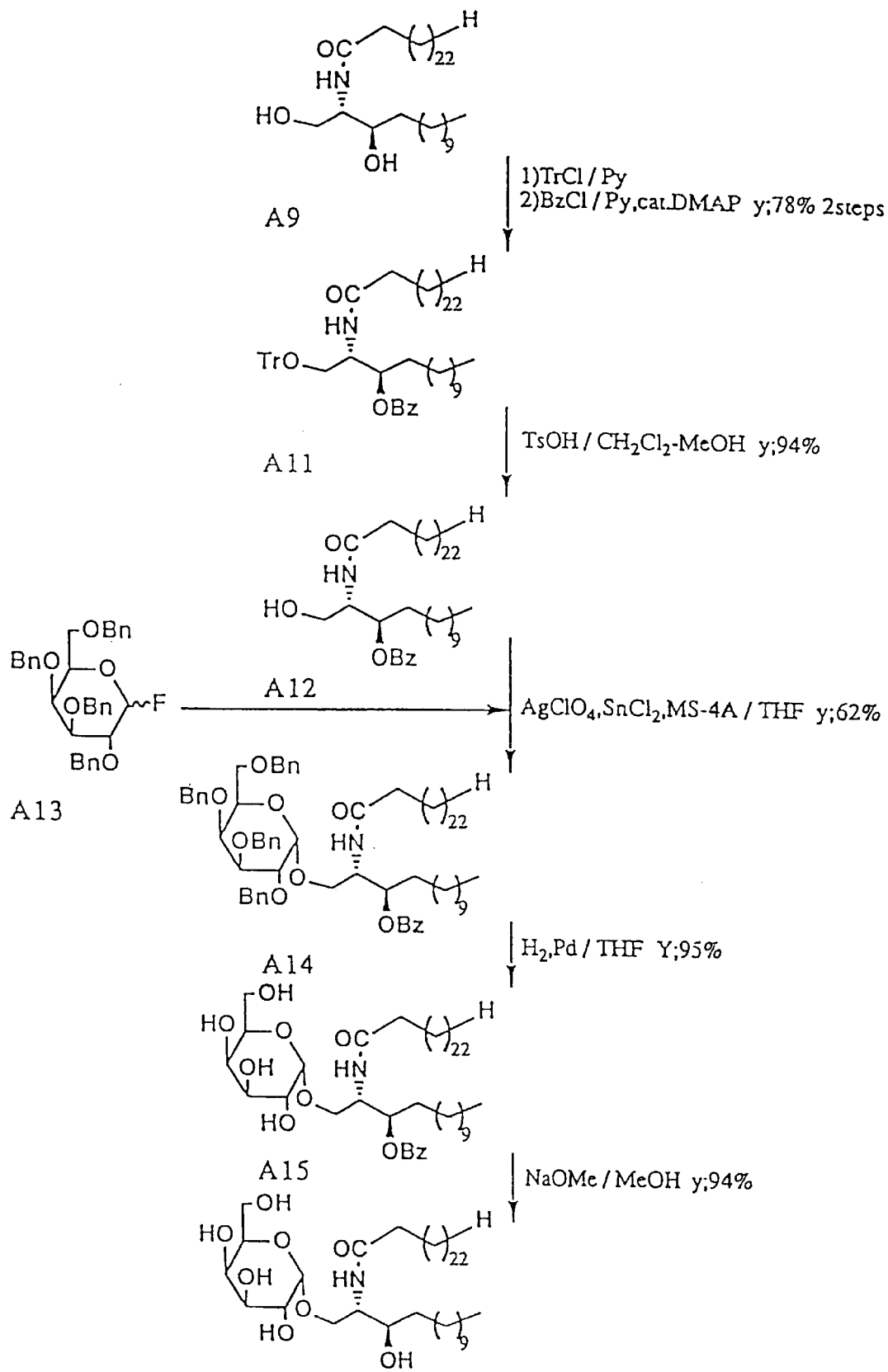

While this reaction route scheme is shown specifically with reference to the aforementioned compound 9, the compounds 1–8 and 10–14 according to the present invention can also e synthesized by applying this method (see FIGS. 5a and 5b).

In the above scheme, the following abbreviations are used.

DMAP: 4-dimethylaminopyridine,

TsOH: p-toluenesulfonic acid,

MS-4A: Molecular Sieves-4A (dehydrating agent).

The other abbreviations have the same meanings as in the previous route schemes.

Furthermore, the compound 29 leaving a double bond unreacted therein can be synthesized by condensation with a fatty acid having a double bond and by the deprotection at the final step with liquid ammonia and metallic sodium.

[Synthesis of the compound 9 (FIGS. 5a and 5b)]

The compound A1 can be synthesized in accordance with the method described in Synthesis, 961–963, 1984.

(i) Synthesis of the compound A2

To a solution of the compound A1 (2.89 g) in 2-methyl-2-propanol (25 ml) was added a 5% aqueous sulfuric acid solution (25 ml), and the mixture was stirred at 45° C. for 15 hours. After being neutralized with powdery sodium hydrogen carbonate under ice-cooling, the reaction mixture was concentrated. The residue, to which water (30 ml) was added, was extracted with ethyl acetate (three times), and the organic layer was concentrated. Purification on a silica gel column (Wako Gel C-200, 100 g) using hexane-acetone (2:1) as an eluent afforded a diol in an amount of 2.28 g (yield: 88.5%).

MS: FDMS 330.

The mixture of the diol (2.25 g) with ethanol (50 ml), water (12 ml) and sodium metaperiodate (2.33 g) was stirred at room temperature for 10 hours. Precipitates were removed by filtration, and the filtrate was concentrated. The residue was diluted with chloroform and washed with brine. The organic layer was concentrated to give an aldehyde (compound A2) in an amount of 1.31 g. The aldehyde was directly used for the next reaction without purification.

(ii) Synthesis of the compound A3

To decanetriphenylphosphonium bromide (8.0 g) was added tetrahydrofuran (20 ml) under an argon atmosphere. After adding a 2.8N solution of n-butyllithium in hexane (6.2 ml) to the mixture at −10° C., stirring was continued for 30 minutes. After the addition of the aldehyde (compound A2, 1.31 g) dissolved in tetrahydrofuran (5 ml), the mixture was allowed to warm to room temperature and stirred for 15 hours and concentrated. The reaction mixture was diluted with brine, and extracted twice with ethyl acetate. The organic layer was washed with brine and concentrated. Purification of the residue on a silica gel column (Wako Gel C-200, 100 g) by eluting with hexane-ethyl acetate (5:1) gave the alcohol (compound A3) in an amount of 1.47 g (yield, 51.0%).

Data of the compound A3

MS: FDMS 426.

NMR: $^1$H (500 MHz, CDCl$_3$; 27° C.)

δ (ppm) 7.25–7.35 (10H, m), 5.69–5.79 [1H, (5.75, dt, J=7.3, 11.0 Hz), (5.72, dt, J=6.7, 15.2 Hz)], 5.31–5.38 [1H, 5.36, bt, J=8.5 Hz), (5.33, bt, J=9.8 Hz)], 4.34–4.62 [2H, (4.61 & 4.35, ABq, J=11.6 Hz), (4.56 & 4.50, ABq, J=12.2 Hz), (4.55 & 4.52, ABq, J=11.6 Hz)], 4.28 (0.7H, dd, J=6.7, 9.7 Hz), 3.85 (0.3H, bt, J=7.9 Hz), 3.74–3.78 (1H, m), 3.56–3.60 [1H (3.59, dd, J=3.1, 9.8 Hz), (3.58, overlapped)], 3.47 (1H, dd, J=5.5, 9.8 Hz), 1.96–2.11 (1H, m), 1.25–1.57 (14H, m), 0.88 (3H, t, J=6.7 Hz).

(iii) Synthesis of the compound A4

The alcohol (compound A3, 0.83 g) was dissolved in tetrahydrofuran (10 ml). 10% Palladium on charcoal (1.0 g) was added, and the reaction vessel was purged with hydrogen. After the mixture was stirred at room temperature for 12 hours, it was filtered through celite and the filtrate was concentrated. Purification on a silica gel column (Wako Gel C-200, 30 g) eluting with hexane-ethyl acetate (5:1) afforded a reduction product (compound A4) in an amount of 0.81 g (yield, 97.1%).

Data of the compound A4

MS: FDMS 428.

NMR: $^1$H (500 MHz, CDCl$_3$; 27° C.)

δ (ppm) 7.25–7.46 (10H, m), 4.50 & 4.62 (2H, ABq, J=11.0 Hz), 4.54 (2H, s), 3.79–3.83 (1H, m), 3.48–3.56 (3H, m), 2.42 (1H, d, J=6.1 Hz), 1.26–2.04 (20H, m), 0.88 (3H, t, J=7.3 Hz).

(iv) Synthesis of the compound A5

After adding methanesulfonyl chloride (0.29 ml) to the reduction product (compound A4, 0.80 g) in pyridine (15 ml), the mixture was stirred at room temperature for 16 hours. The reaction mixture was concentrated and distilled azeotropically with toluene. The residue dissolved in diethyl ether was washed with brine and concentrated. Purification on a silica gel column (Wako Gel C-200, 30 g) eluting with hexane-acetone (6:1) afforded a mesylated product (compound A5) in an amount of 0.87 g (yield, 91.9%).

Data of the compound A5

MS: FDMS 504.

NMR: $^1$H (500 MHz, CDCl$_3$; 27° C.)

δ (ppm) 7.27–7.38 (10H, m), 4.81–4.84 (1H, m), 4.59 (2H, s), 4.55 & 4.50 (2H, ABq, J=11.6 Hz), 3.75 (1H, dd, J=3.1, 11.0 Hz), 3.71 (1H, dd, J=6.7, 11.0 Hz), 3.67 (1H, dt, J=4.3, 8.5 Hz), 2.99 (3H, s), 1.24–1.64 (20H, m), 0.88 (3H, t, J=7.3 Hz).

(v) Synthesis of the compound A6

To the mesylated product (compound A5, 0.86 g) were added dimethylformamide (10 ml) and sodium azide (885 mg), and the mixture was stirred at 120° C. for 15 hours. The reaction mixture was diluted with brine, extracted with ethyl acetate (three times), and then concentrated. Purification on a silica gel column (Wako Gel C-200, 30 g) eluting with hexane-ethyl acetate (40:1) afforded an azide (compound A6) in an amount of 0.73 g (yield, 94.3%).

Data of the compound A6

MS: FDMS 453.

NMR: $^1$H (500 MHz, CDCl$_3$; 27° C.)

δ (ppm) 7.27–7.44 (10H, m), 4.54 & 4.58 (2H, ABq, J=12.2 Hz), 4.52 & 4.57 (2H, ABq, J=11.0 Hz), 3.68–3.70 (2H, m), 3.63 (1H, dd, J=8.5, 11.0 Hz), 3.53 (1H, dt, J=4.3, 8.6 Hz), 1.25–1.64 (20H, m), 0.88 (3H, t, J=6.7 Hz).

(vi) Synthesis of the compound A7

To the azide (compound A6, 0.72 g) were added tetrahydrofuran (7 ml) and 10% palladium on charcoal (70 mg), and the mixture was stirred at room temperature after the reaction vessel was purged with hydrogen. The reaction mixture was filtered through celite, and the filtrate was concentrated. Purification on a silica gel column (Wako Gel C-200, 15 g) eluting with hexane-acetone (6:1) afforded an amine (compound A7) in an amount of 0.62 g (yield, 91.5%).

Data of the compound A7

MS: FDMS 427.

NMR: $^1$H (500 MHz, CDCl$_3$; 27° C.)

δ (ppm) 7.27–7.36 (10H, m), 4.51 & 4.54 (2H, ABq, J=11.6 Hz), 4.52 (2H, s), 3.58 (1H, dd, J=3.7, 9.2 Hz), 3.41–3.45 (2H, m), 3.20 (1H, dt, J=4.3, 7.3 Hz), 1.26–1.63 (20H, m), 0.88 (3H, t, J=6.7 Hz).

(vii) Synthesis of the compound A8

To the amine (compound A7, 0.61 g) were added methylene chloride (20 ml), 2-chloro-1-methylpyridinium iodide (483 mg) and n-tributylamine (0.45 ml). Tetracosanic acid (597 mg) was further added, and the mixture was heated under reflux for 2 hours. The reaction mixture was cooled to room temperature, washed sequentially with 5% aqueous sodium thiosulfate solution, 5% aqueous sodium hydrogen carbonate solution and brine, and then concentrated. Purification on silica gel column (Wako Gel C-200, 20 g) eluting with hexane-acetone (20:1) afforded an amide (compound A8) in an amount of 0.56 g (yield, 51.2%).

Data of the compound A8

MS: FDMS 777.

NMR: $^1$H (500 MHz, CDCl$_3$; 27° C.)

δ (ppm) 7.28–7.35 (10H, m), 5.66 (1H, d, J=9.2 Hz), 4.45 & 4.58 (2H, ABq, J=11.6 Hz), 4.48 (2H, s), 4.25–4.30 (1H, m), 3.73 (1H, dd, J=4.9, 9.8 Hz), 3.57 (1H, dt, J=5.5, 6.7 Hz), 3.52 (1H, dd, J=4.3, 9.8 Hz), 2.08 (2H, dt, J=3.1, 10.4 Hz), 1.26–1.58 (64H, m), 0.88 (6H, t, J=6.7 Hz).

(viii) Synthesis of the compound A9

To the amide (compound A8, 0.55 g) were added tetrahydrofuran (15 ml) and palladium black (55 mg). The reaction vessel was purged with hydrogen, and the mixture was stirred at room temperature for 16 hours. The reaction mixture was filtered through celite, and the filtrate was concentrated. Purification on a silica gel column (Wako Gel C-200, 20 g) eluting with chloroform-methanol (20:1) afforded a diol (compound A9) in an amount of 302 mg (yield, 71.6%).

Data of the compound A9
MS: FDMS 597.
NMR: $^1$H (500 MHz, $C_5D_5N$; 27° C.)
δ (ppm) 8.34 (1H, d, J=7.9 Hz), 4.62–4.67 (1H, m), 4.46 (1H, dd, J=4.9, 11.0 Hz), 4.30 (1H, dd, J=5.8, 11.6 Hz), 4.25–4.32 (1H, m), 2.48 (2H, dt, J=2.4, 7.3 Hz), 1.23–1.97 (62H, m), 0.88 (6H, t, J=6.7 Hz).

(ix) Synthesis of the compound A10

To the diol (compound A9, 70 mg) were added pyridine (5 ml), triphenylmethyl chloride (261 mg) and 4-dimethylaminopyridine (5 mg), and the mixture was stirred at 60° C. for 2 hours. The reaction mixture was diluted with chloroform, washed with brine and concentrated. Purification on a silica gel column (Wako Gel C-200, 10 g) eluting with chloroform-acetone (100:1) afforded a tritylated derivative (compound A10) in an amount of 90.2 mg (yield, 91.6%).

Data of the compound A10
MS: FDMS 837.
NMR: $^1$H (500 MHz, $CDCl_3$; 27° C.)
δ (ppm) 7.25–7.47 (15H, m), 6.28 (1H, d, J=7.9 Hz), 3.93–3.96 (1H, m), 3.58–3.61 (1H, m), 3.52 (1H, dd, J=3.1, 9.8 Hz), 3.26 (1H, dd, J=3.7, 9.8 Hz), 2.95 (1H, d, J=9.2 Hz), 2.24 (2H, t, J=7.3 Hz), 1.25–1.70 (62H, m), 0.88 (6H, t, J=7.3 Hz).

(x) Synthesis of the compound A11

To the trityl derivative (compound A10, 87 mg) in pyridine (3.0 ml) were added benzoyl chloride (24 μl) and 4-dimethylaminopyridine (3 mg), and the mixture was stirred for 4 hours. After the mixture to which ice-water had been added was stirred for 30 minutes, it was diluted with chloroform, washed with water and concentrated. Purification on a silica gel column (Wako Gel C-200, 10 g) eluting with hexane-ethyl acetate (10:1) afforded a benzoyl derivative (compound A11) in an amount of 83.4 mg (yield, 85.3%).

Data of the compound A11
MS: FDMS 941.
NMR: $^1$H (500 MHz, $CDCl_3$; 27° C.)
δ (ppm) 7.16–7.93 (20H, m), 5.74 (1H, d, J=9.2 Hz), 5.34–5.37 (1H, m), 4.39–4.48 (1H, m), 3.40 (1H, dd, J=3.7, 9.8 Hz), 3.19 (1H, dd, J=3.7, 9.8 Hz), 2.09 (2H, dt, J=2.5, 9.8 Hz), 1.25–1.74 (64H, m), 0.88 & 0.87 (each 3H, t, J=7.3 Hz).

(xi) Synthesis of the compound A12

To the benzoyl derivative (compound A11, 80 mg) were added methylene chloride (1.0 ml) and methanol (0.5 ml). p-Toluenesulfonic acid monohydrate (20 mg) was added, and the mixture was stirred at room temperature for 2 hours. The reaction mixture was diluted with ethyl acetate, washed with a 5% aqueous sodium hydrogen carbonate and brine, and then concentrated. Purification on a silica gel column (Wako Gel C-200, 5 g) eluting with hexane-ethyl acetate (2:1) afforded an alcohol (compound A12) in an amount of 58 mg (yield, 93.6%).

Data of the compound A12
MS: FDMS 701.
NMR: $^1$H (500 MHz, $CDCl_3$; 27° C.)
δ (ppm) 7.46–8.06 (5H, m), 6.25 (1H, d, J=8.5 Hz), 5.06–5.09 (1H, m), 4.15–4.19 (1H, m), 3.58–3.68 (2H, m), 2.23 (2H, t, J=6.7 Hz), 1.22–1.77 (62H, m), 0.88 & 0.87 (each 3H, t, J=7.3 Hz).

(xii) Synthesis of the compound A14

A solution of the alcohol (compound A12, 58 mg) in tetrahydrofuran (3.0 ml) was stirred with stannous chloride (37 mg), silver perchlorate (41 mg) and Molecular Sieves 4A powder (300 mg). After stirring for 30 minutes, the mixture was cooled to −10° C., and a solution of benzyl galactosyl fluoride (compound A13, 68 mg) in tetrahydrofuran (1.5 ml) was added. The mixture was allowed to warm gradually to room temperature, stirred for 2 hours and filtered through celite. The filtrate was concentrated. Purification on a silica gel column (Wako Gel C-200, 5 g) eluting with hexane-ethyl acetate (5:1) afforded an α-galactoside (compound A14) in an amount of 62.6 mg (yield, 61.8%).

Data of the compound A14
MS: FDMS 1224.
NMR: $^1$H (500 MHz, $CDCl_3$; 27° C.)
δ (ppm) 8.02 (2H, d, J=7.3 Hz), 7.56 (1H, t, J=7.9 Hz), 7.43 (2H, t, J=7.9 Hz), 7.23–7.39 (20H, m), 6.58 (1H, d, J=9.2 Hz), 5.30 (1H, dt, J=3.7, 7.9 Hz), 4.90 & 4.55 (2H, ABq, J=11.6 Hz), 4.77 & 4.69 (2H, ABq, J=11.6 Hz), 4.75 (1H, d, J=3.7 Hz), 4.73 & 4.65 (2H, ABq, J=12.2 Hz), 4.47 & 4.38 (2H, ABq, J=12.2 Hz), 430–4.34 (1H, m), 4.10–4.12 (1H, m), 4.01 (1H, dd, J=3.7, 9.8 Hz), 3.97 (1H, dd, J=3.7, 12.2 Hz), 3.84–3.93 (2H, m), 3.57 (1H, dd, J=3.1, 12.2 Hz), 3.52 (1H, dd, J=7.3, 9.2 Hz), 3.29 (1H, dd, J=4.3, 9.8 Hz), 1.98–2.09 (2H, m), 1.18–1.68 (62H, m), 0.88 (3H, t, J=6.7 Hz), 0.86 (3H, t, J=7.3 Hz).

(xiii) Synthesis of the compound A15

To the α-galactoside (compound A14, 56 mg) were added tetrahydrofuran (4.0 ml) and palladium black (15 mg), and the mixture was stirred at room temperature for 16 hours after the reaction vessel was purged with hydrogen. The reaction mixture was filtered through celite, concentrated and purified on a silica gel column (Wako Gel C-200, 2 g) eluting with chloroform-methanol (20:1) to give a tetraol (compound A15) in an amount of 37.4 mg (yield, 94.7%).

Data of the compound A15
MS: FDMS 863.
NMR: $^1$H (500 MHz, $CDCl_3$; 27° C.)
δ (ppm) 8.04 (2H, d, J=7.9 Hz), 7.62 (1H, t, J=7.9 Hz), 7.48 (2H, t, J=7.3 Hz), 6.16 (1H, d, J=9.2 Hz), 5.21–5.24 (1H, m), 4.81 (1H, d, J=2.4 Hz), 4.45–4.46 (1H, m), 4.08 (1H, bs), 3.91–3.94 (1H, m), 3.87 (1H, dd, J=2.4, 10.4 Hz), 3.75–3.85 (4H, m), 3.57 (1H, dd, J=5.5, 11.6 Hz), 2.22 (2H, dt, J=1.8, 7.3 Hz), 1.22–1.79 (62H, m), 0.88 (3H, t, J=7.3 Hz), 0.87 (3H, t, J=6.7 Hz).

(xiv) Synthesis of the compound 9

To the tetraol (compound A15, 36.0 mg) were added methanol (3 ml) and a 1N methanolic sodium methoxide solution (0.3 ml), and the mixture was stirred for 2 hours. The mixture was neutralized with resins (Dowex 50W, X8; manufactured by The Dow Chemical Company), and then filtered. The solids removed was washed sufficiently with chloroform-methanol (1:1), and the extract was combined with the filtrate, and then concentrated. Purification on a silica gel column (Wako Gel C-200, 2 g) eluting with chloroform-methanol (10:1) afforded the compound 9 in an amount of 29.7 mg (yield, 94.0%).

Data of the compound 9
[α]$^{23}_D$=+49.0° (pyridine, c=1.31)
MS: FDMS 759.
IR: (cm$^{-1}$, KBr) 3200, 2870, 2800, 1630, 1530, 1450, 1080.
mp: 151°–155° C.
NMR: $^1$H (500 MHz, C$_5$D$_5$N; 27° C.)
δ (ppm) 8.49 (1H, d, J=8.6 Hz), 6.11–6.52 (5H, m), 5.45 (1H, d, J=3.7 Hz), 4.73 (1H, m), 4.65 (1H, dd, J=3.8, 10.4 Hz), 4.53–4.57 (2H, m), 4.43–4.49 (4H, m), 4.36 (1H, dd, J=5.5, 10.4 Hz), 4.27 (1H, m), 2.47 (2H, t, J=6.7 Hz), 1.83–1.91 (4H, m), 1.23–1.56 (58H, m), 0.88 (6H, t, J=7.3 Hz).
$^{13}$C (125 MHz, C$_5$D$_5$N; 27° C.)
δ (ppm) 173.4 (s), 102.1 (d), 73.1 (d), 71.9 (d), 71.7 (d), 71.0 (d), 70.5 (d), 69.7 (t), 62.7 (t), 54.9 (d), 36.8 (t), 35.1 (t), 32.1 (t), 30.2 (t), 30.1 (t), 30.0 (t), 29.9 (t), 29.8 (t), 29.7 (t), 29.6 (t), 26.6 (t), 26.4 (t), 22.9 (t), 14.3 (q).

(2) Synthetic route B

While this scheme specifically illustrates the synthetic routes of the aforementioned compounds 7 and 5, the compounds according to the present invention (1–4, 6, 8–14) can also be synthesized by applying this method.

Figure 6:
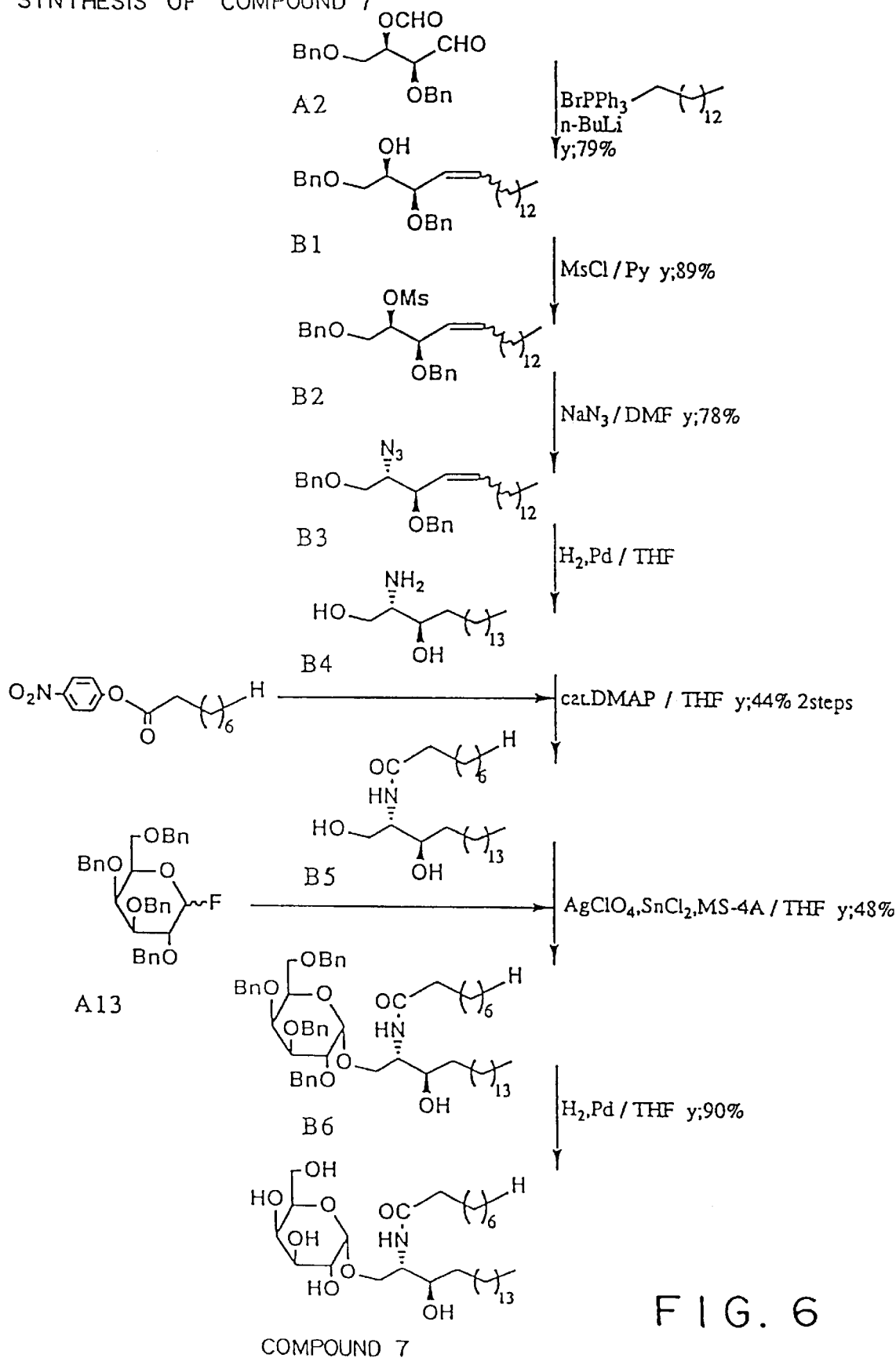
FIG. 6 shows the scheme which illustrates a preferred method for synthesizing the compound 7 ((2S,3R)-1-(α-D-galactopyranosyloxy)-2-octanoylamino-3-octadecanol)

[Synthesis of the compound 7 (FIG. 6)]

Abbreviatios in the aforementioned scheme are the same as those in the previously described scheme.

(i) Synthesis of the compound B1

To tetradecanetriphenylphosphonium bromide (213.7 g) was added tetrahydrofuran (630 ml), and the reaction vessel was purged with argon. A 2.3N solution of n-butyl lithium in hexane (173 ml) was added at −30° C., and the mixture was stirred for 3.5 hours. A (2R,3R)-aldehyde (compound A2, 31.73 g) dissolved in tetrahydrofuran (630 ml) was added dropwise, and the mixture was stirred for 2 hours, and then concentrated. The residue was diluted with ethyl acetate, washed with water and brine, and then concentrated. Purification on a silica gel column (Wako Gel C-200, 850 g) eluting with hexane-ethyl acetate (9:1) afforded an alcohol (compound B1) in an amount of 36.31 g (yield, 79.0%).

Data of the compound B1
MS: FDMS 481.
NMR: $^1$H (500 MHz, CDCl$_3$; 27° C.)
δ (ppm) 7.26–7.46 (10H, m), 5.69–5.78 (1H, m), 5.31–5.38 (1H, m), 4.34–4.63 (5H, m), 4.28 (0.7H, dd, J=6.7, 9.2 Hz), 3.85 (0.3H, t, J=7.3 Hz), 3.75–3.78 (1H, m), 3.56–3.60 (1H, m), 3.47 (1H, dd, J=5.5, 10.4 Hz), 1.98–2.11 (2H, m), 1.26–1.34 (22H, m), 0.88 (3H, t, J=6.7 Hz).

(ii) Synthesis of the compound B2

To a solution of the alcohol (compound B1, 5.03 g) in pyridine (50 ml) was added methanesulfonyl chloride (1.62 ml), and the mixture was stirred at room temperature for 16 hours. The mixture was concentrated and a residual acid chloride was distilled azeotropically together with toluene. The residue was diluted with diethyl ether, washed with brine, and then concentrated. Purification on a silica gel column (Wako Gel C-200, 200 g) eluting with hexane-acetone (10:1) afforded a mesyl derivative (compound B2) in an amount of 5.20 g (yield, 88.9%).

Data of the compound B2
MS: FDMS 558.
NMR:
$^1$H (500 MHz, CDCl$_3$; 27° C.)
δ (ppm)
7.23–7.35 (10H, m), 5.77–5.83 (1H, m), 5.26–5.35 (1H, m), 4.71–4.77 (1H, m), 4.33–4.62 (5H, m), 4.06 (0.3H, t, J=8.1 Hz), 3.74 (0.7H, dd, J=3.1, 11.0 Hz), 3.65–3.70 (1H, m), 2.964 (0.9H, s), 2.956 (2.1H, s), 1.99–2.17 (2H, m), 1.26–1.37 (22H, m), 0.88 (3H, t, J=6.8 Hz).

(iii) Synthesis of the compound B3

To the mesyl derivative (compound B2, 1.52 g) were added dimethylformamide (20 ml) and sodium azide (1.42 g). After stirring at 120° C. for 12 hours, the mixture was diluted with brine, extracted with ethyl acetate (three times), and then concentrated. Purification on a silica gel column (Wako Gel C-200, 50 g) eluting with hexane-ethyl acetate (40:1) afforded an azide derivative (compound B3) in an amount of 1.07 g (yield, 77.7%).

Data of the Compound B3
IR: (cm$^{-1}$, KBr)
2870, 2810, 2050, 1490, 1440.
NMR: $^1$H (500 MHz, CDCl$_3$; 27° C.)
δ (ppm)
7.25–7.35 (10H, m), 5.69–5.82 (1H, m), 5.35–5.43 (1H, m), 4.30–4.74 (4H, m), 3.89 (0.3H, dd, J=5.5, 8.5 Hz), 3.55–3.70 (3.7H, m), 1.97–2.10 (2H, m), 1.25–1.36 (22H, m), 0.88 (3H, t, J=6.8 Hz).

(iv) Synthesis of the compound B5

To a solution of the azide (compound B3, 0.45 g) in tetrahydrofuran (10 ml) were added a 10% methanolic hydrochloric acid solution (2 ml) and palladium black (0.25 g). After the reaction vessel was purged with hydrogen, the mixture was stirred at room temperature for 12 hours, and then filtered through celite. The filtrate was concentrated to give a white powdery amine (the hydrochloric salt of compound B4, 301 mg). Tetrahydrofuran (10 ml), p-nitrophenyl octanoate (260 mg) and triethylamine (0.15 ml) were added to the amine, the mixture was stirred at 60° C. for 12 hours. The reaction mixture was concentrated to give a syrup. Purification of the syrup on a silica gel column (Wako Gel C-200, 50 g) eluting with chloroform-methanol (20:1) afforded an amide derivative (compound B5) in an amount of 166 mg (yield based on the compound B3, 43.6%.

Data of the compound B5
MS: FDMS 429.
NMR: $^1$H (500 MHz, C$_5$D$_5$N; 27° C.)
δ (ppm)
8.37 (1H, d, J=7.9 Hz), 4.63–4.69 (1H, m), 4.44–4.49 (1H, m), 4.25–4.35 (2H, m), 2.46 (2H, dt, J=3.1, 7.9 Hz), 1.78–1.95 (4H, m), 1.16–1.59 (34H, m), 0.87 & 0.82 (each 3H, t, J=6.7 Hz).

(v) Synthesis of the compound B6

To a solution of the amide (compound B5, 48 mg) in tetrahydrofuran (1.0 ml) were added stannous chloride (75 mg), silver perchlorate (82 mg) and powdery Molecular Sieves 4A (200 mg), and the mixture was stirred for 30 minutes. The mixture was cooled to −10° C., and a solution of benzylgalactosyl fluoride (compound A13, 67 mg) in tetrahydrofuran (2.0 ml) was added thereto. The mixture was allowed to warm gradually to room temperature, stirred for 2 hours, and then filtered through celite. The solids removed were washed with a small amount of acetone and combined with the filtrate, and then concentrated. Purification on a silica gel column (Wako Gel C-200, 5 g) eluting with hexane-ethyl acetate (3:1) afforded a crude α-galactoside (compound B6), which was subjected to the subsequent reaction.

(vi) Synthesis of the compound 7

To a solution of the α-galactoside (compound B6, 47 mg) in ethyl acetate (1.5 ml) was added palladium black (15 mg). After the reaction vessel was purged with hydrogen, the mixture was stirred at room temperature for 16 hours. The reaction vessel was filtered through celite, and the filtrate was concentrated. Purification on a silica gel column (Wako Gel C-200, 2 g) eluting with chloroform-methanol (10:1) afforded the compound 7 in an amount of 25.1 mg (yield based on the compound B5, 37.9%).

Data of the compound 7

[α]$^{23}_D$=+58.2° (pyridine, c=0.56)

MS: FDMS 591.

IR: (cm$^{-1}$, KBr)

3300, 2870, 1640, 1535, 1460, 1060.

mp: 155–157° C.

NMR:

$^1$H (500 MHz, C$_5$D$_5$N; 27° C.)

δ (ppm)

8.49 (1H, d, J=8.6 Hz), 6.52 (2H, m), 6.42 (1H, m), 6.33 (1H, bs), 6.12 (1H, bd, J=6.7 Hz), 5.46 (1H, d, J=3.7 Hz), 4.73 (1H, m), 4.65 (1H, m), 4.53–4.57 (2H, m), 4.40–4.49 (5H, m), 4.36 (1H, dd, J=5.5, 10.4 Hz), 4.27 (1H, m), 2.45 (2H, dt, J=5.5, 7.9 Hz), 1.80–1.92 (4H, m), 1.18–1.58 (34H, m), 0.87 & 0.81 (each 3H, t, J=6.7 Hz).

$^{13}$C (125 MHz, C$_5$D$_5$N; 27° C.)

δ (ppm)

173.4 (s), 102.2 (d), 73.1 (d), 72.0 (d), 71.7 (d), 71.0 (d), 70.8 (d), 70.5 (d), 69.7 (t), 62.7 (t), 54.9 (d), 36.8 (t), 35.1 (t), 32.1 (t), 31.9 (t), 30.2 (t), 30.1 (t), 30.0 (t), 29.9 (t), 29.64 (t), 29.61 (t), 29.4 (t), 26.6 (t), 26.4 (t), 22.93 (t), 22.86 (t), 14.3 (q), 14.2 (q).

Figure 7:
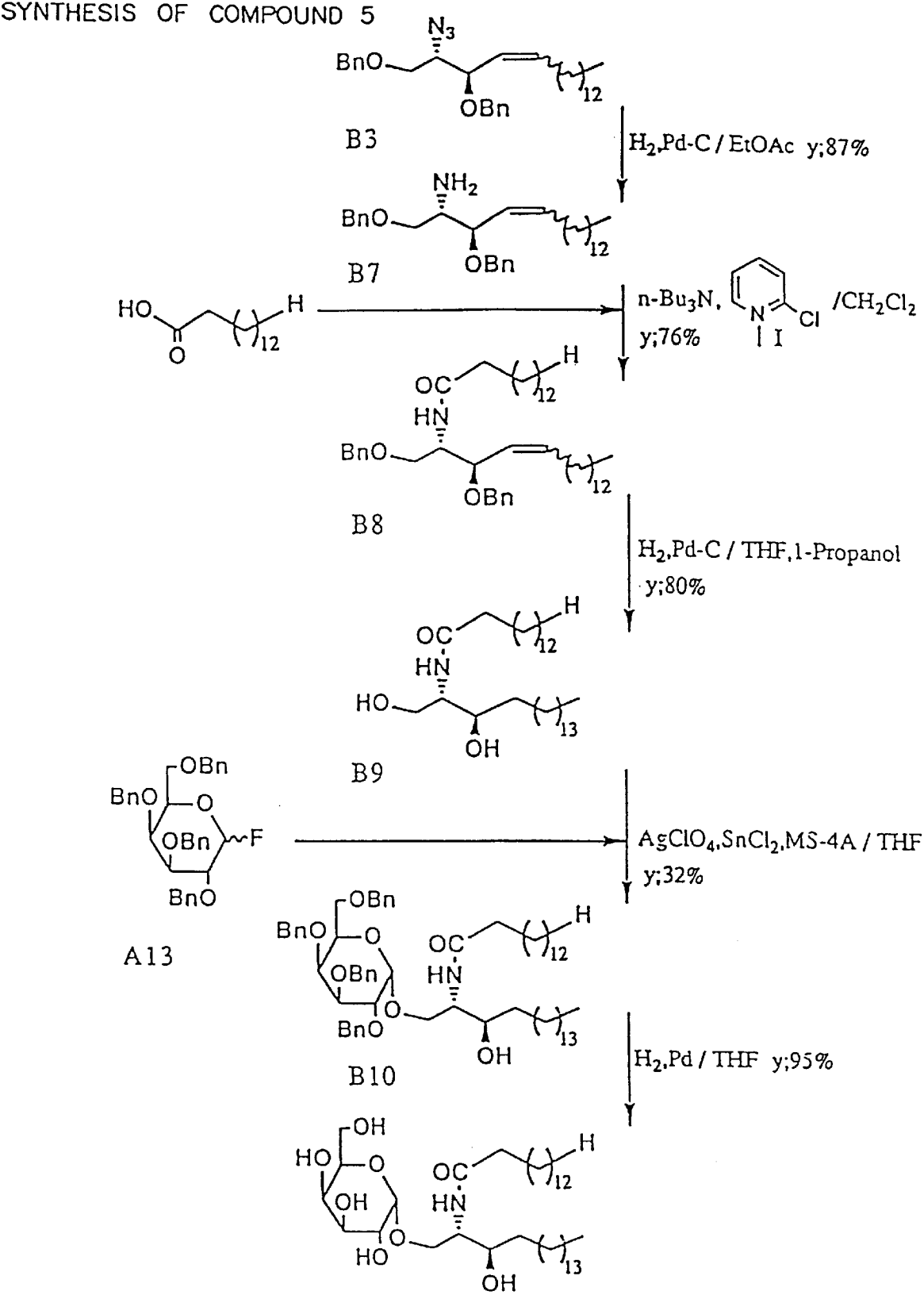
FIG. 7 shows the scheme which illustrates a preferred method for synthesizing the compound 5 ((2S,3R)-1-(α-D-galactopyranosyloxy)-2-tetradecanoylamino-3-octadecanol)

[Synthesis of the compound 5 (FIG. 7)]

Abbreviations in the aforementioned scheme are the same as those in the previously described scheme.

(i) Synthesis of the compound B7

To a solution of the azide (compound B3, 3.9 g) in ethyl acetate (50 ml) was added 10% palladium on charcoal (1.2 g). After the reaction vessel was purged with hydrogen, the mixture was stirred at room temperature for 16 hours. The catalyst was filtered off, and the filtrate was concentrated and purified on a silica gel column (Wako Gel C-200, 300 g, hexane-acetone (6:1)) to give an amine (compound B7) in an amount of 3.22 g (yield, 86.7%).

MS: FDMS 480.

NMR: $^1$H (500 MHz, CDCl$_3$; 27° C.)

δ (ppm)

7.24–7.35 (10H, m), 5.70 (0.7H, dt, J=7.3, 11.6 Hz), 5.71 (0.3H, dt, J=6.7, 15.3 Hz), 5.34–5.41 (1H, m), 4.30–4.58 (4H, m), 4.17 (0.7H, dd, J=6.7, 9.8 Hz), 3.72 (0.3H, dd, J=6.7, 8.5 Hz), 3.42–3.66 (2H, m), 3.06–3.10 (1H, m), 2.01–2.14 (2H, m), 1.26–1.50 (22H, m), 0.88 (3H, t, J=6.7 Hz).

(ii) Synthesis of the compound B8

To a solution of the amine (compound B7, 2.22 g) in methylene chloride (50 ml), 2-chloro-1-methylpyridinium iodide (1.88 g) were added n-tributylamine (1.75 ml) and myristic acid 1.47 g), and the mixture was heated under reflux and stirred for 2 hours. The reaction mixture was washed sequentially with a 5% aqueous sodium thiosulfate solution and brine, and then concentrated. Purification on a silica gel column (Wako Gel C-200, 100 g) eluting with chloroform-acetone (200:1) afforded an amide (compound B8) in an amount of 2.41 g (yield, 75.6%).

MS: FDMS 691.

NMR: $^1$H (500 MHz, CDCl$_3$; 27° C.)

δ (ppm)

7.26–7.32 (10H, m), 5.64–5.73 (2H, m), 5.33–5.41 (1H, m), 4.19–4.59 (6H, m), 3.79–3.89 (1H, m), 3.51–3.58 (1H, m), 1.98–2.13 (2H, m), 1.26–1.58 (46H, m), 0.88 (6H, t, J=6.7 Hz).

(iii) Synthesis of the compound B9

To the amide (compound B8, 3.50 g) were added 1-propanol (15 ml), tetrahydrofuran (15 ml), 10% palladium on charcoal (1.2 g) and formic acid (3.0 ml). The mixture was stirred at 45° C. for 16 hours under the nitrogen atmosphere. The catalyst was removed by filtration, and the filtrate was concentrated. Crystallization of the residue from chloroform-acetone afforded a ceramide (compound B9) in an amount of 2.08 g (yield, 80.4%).

[α]$^{24}_D$=+3.5° (pyridine, c=1.87)

MS: FDMS 513.

mp: 104–105° C.

NMR: $^1$H (500 MHz, C$_5$D$_5$N; 27° C.)

δ (ppm)

8.35 (1H, d, J=9.2 Hz), 6.36 (1H, t, J=4.9 Hz), 6.24 (1H, d, J=6.1 Hz), 4.62–4.67 (1H, m), 4.46 (1H, dt, J=4.9, 11.0 Hz), 4.25–4.33 (2H, m), 2.47 (2H, dt, J=1.8, 7.3 Hz), 1.25–1.95 (50H, m), 0.88 (6H, t, J=6.7 Hz).

(iv) Synthesis of the compound B10

To a solution of the ceramide (compound B9, 1.0 g) in tetrahydrofuran (30 ml) were added stannous chloride (129 g), silver perchlorate (1.41 g) and powdery Molecular Sieves 4A (1.5 g), and the mixture was stirred for 30 minutes. The mixture was cooled to −10° C., and a solution of benzylgalactosyl fluoride (compound A13, 1.11 g) in tetrahydrofuran (10 ml) was added. The resulting mixture was allowed to warm gradually to room temperature, stirred for 2 hours, and then filtered through celite. The solids removed were washed with a small amount of acetone, and the extract was combined with the filtrate, and then concentrated and purified on a silica gel column (Wako Gel C-200, 150 g, hexane-ethyl acetate (3:1)) to give an α-galactoside (compound B10) in an amount of 646 mg (yield, 32.0%).

MS: FDMS 1035.

NMR: $^1$H (500 MHz, CDCl$_3$; 27° C.)

δ (ppm)

7.23–7.37 (20H, m), 6.49 (1H, d, J=7.9 Hz), 4.92 (1H, d, J=11.3 Hz), 4.84 (1H, d, J=12.2 Hz), 4.73–4.78 (3H, m), 4.67 (1H, d, J=11.6 Hz), 4.46 (1H, d, J=11.6 Hz), 4.37 (1H, d, J=11.6 Hz), 4.03 (1H, dd, J=3.7, 9.8 Hz), 3.96 (1H, bs), 3.83–3.92 (4H, m), 3.70 (1H, dd, J=3.1, 10.4 Hz), 3.47–3.58 (3H, m), 3.40 (1H, d, J=9.8 Hz), 2.12 (2H, dt, J=1.8, 7.9 Hz), 1.25–1.61 (51H, m), 0.88 (6H, t, J=6.7 Hz).

(v) Synthesis of the compound 5

To a solution of the galactoside (compound B10, 1.59 g) in tetrahydrofuran (30 ml) was added palladium black (290 mg). After the reaction vessel was purged with hydrogen, the mixture was stirred at room temperature for 16 hours. The catalyst was removed by filtration, and the filtrate was concentrated. Purification on a silica gel column (Wako Gel C-200, 100 g) eluting with chloroform-methanol (5:1) afforded the compound 5 in an amount of 984 mg (yield, 95.0%).

Data of the compound 5

[α]$^{24}_D$=+57.8° (pyridine, c=1.69)

MS: FDMS 674.

IR: (cm$^{-1}$, KBr)

3400, 3270, 2920, 2850, 1640, 1550, 1465, 1135, 1075, 1045.

mp: 159.0–161.0° C.

NMR: $^1$H (500 MHz, C$_5$D$_5$N; 27° C.)

δ (ppm)

8.52 (1H, d, J=8.6 Hz), 6.51 (1H, m), 6.44 (1H, m), 6.33 (1H, m), 6.15 (1H, m), 5.45 (1H, d, J=3.7 Hz), 4.73 (1H, m), 4.65 (1H, m), 4.40–4.58 (6H, m), 4.36 (1H, dd, J=5.5, 10.0 Hz), 4.28 (1H, m), 2.48 (2H, t, J=7.0 Hz), 1.80–1.95 (4H, m), 1.57 (1H, m), 1.18–1.43 (49H, m), 0.88 (6H, t, J=6.7 Hz).

$^{13}$C (125 MHz, C$_5$D$_5$N; 2720 C.)

δ (ppm)

173.4 (s), 102.2 (d), 73.1 (d), 71.9 (d), 71.7 (d), 71.0 (d), 70.5 (d), 69.7 (t), 62.7 (t), 54.9 (d), 36.8 (t), 35.1 (t), 32.1 (t), 30.2 (t), 30.1 (t), 30.02 (t), 29.97 (t), 29.91 (t), 29.87 (t), 29.8 (t), 29.7 (t), 29.6 (t), 26.6 (t), 26.4 (t), 22.9 (t), 14.3 (q).

(3) Synthetic route C

A specific synthetic route with use of a sphingosine can be illustrated by the following scheme. While the scheme is illustrated specifically with reference to the aforementioned compounds 1 and 5, the compounds (2–4, 6–8, 14) according to the present invention can also be synthesized by applying this method. Furthermore, the compounds 15 and 35 having a double bond can be synthesized by conducting the deprotection with use of liquid ammonia and metallic sodium.

Figure 8:
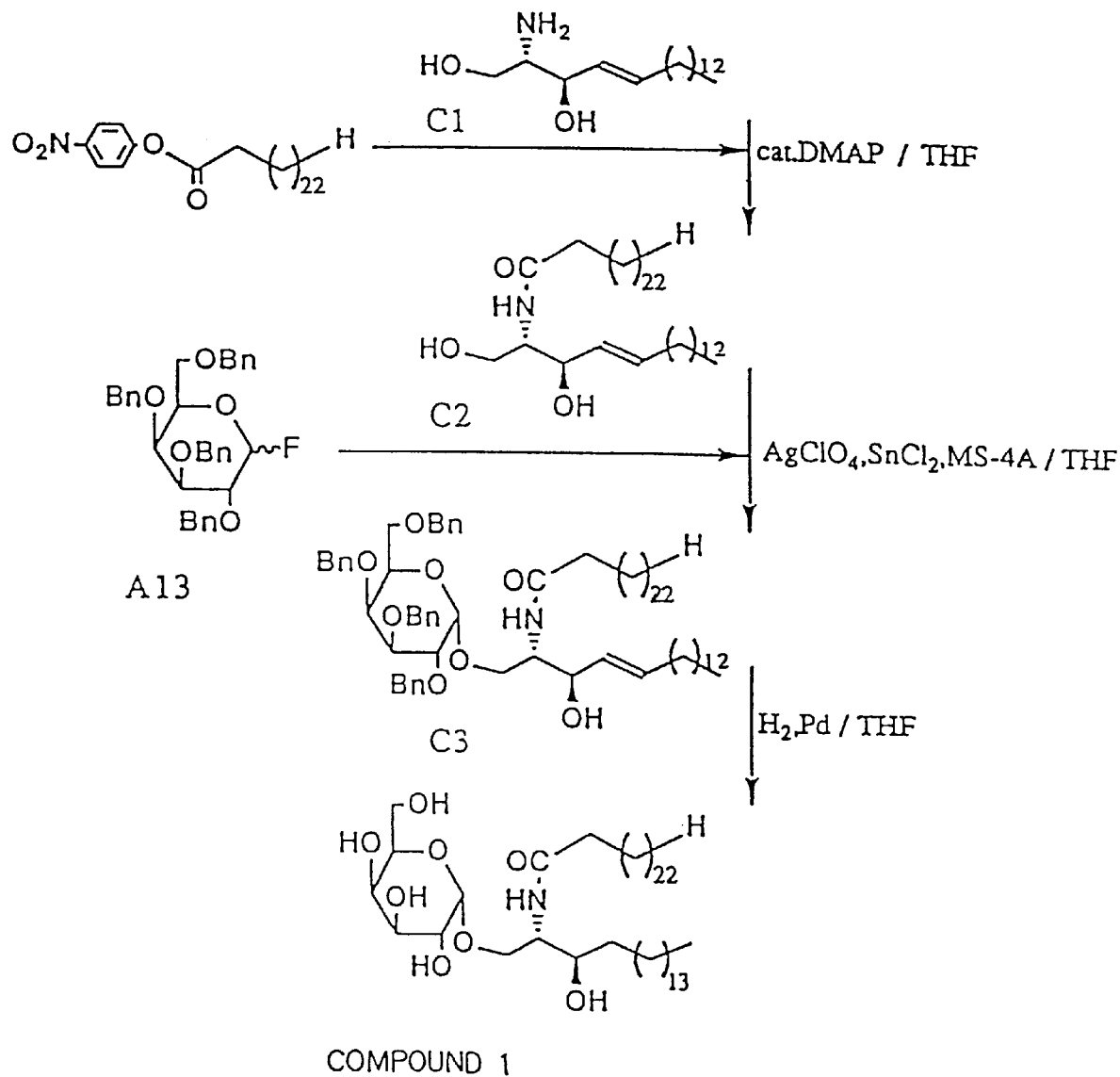
FIG. 8 shows the scheme which illustrates a preferred method for synthesizing the compound 1 ((2S,3R)-1-(α-D-galactopyranosyloxy)-2-tetracosanoylamino-3-octadecanol)

[Synthesis of the compound 1 (FIG. 8)]

Abbreviations in the aforementioned scheme are the same as those in the previously described schemes.

(i) Synthesis of the compound C2

To a solution of sphingosine (25 mg) in tetrahydrofuran (1ml) were added p-nitrophenyl tetracosanate (81.8 mg) and 4-dimethylaminopyridine (2.5 mg), and the mixture was stirred at 40° C. for 12 hours. The mixture was evaporated under reduced pressure. Purification on a silica gel column (Wako Gel C-200, 10 g) eluting with chloroform-methanol (4:1) afforded an amide (compound C2) in an amount of 23.2 mg (yield, 42.7%).

Data of the compound C2

$[\alpha]^{23}_D$=−11.3° (pyridine, c=1.03)

MS: FDMS 651.

IR: ($cm^{-1}$, KBr)

3280, 2910, 2840, 1635, 1540, 1465.

mp: 87.5–89.5° C.

NMR: $^1$H (500 MHz, $CDCl_3+CD_3+OD$ (1 drop); 27° C.)

δ (ppm)

5.76 (1H, dt, J=6.7, 15.3 Hz), 5.49 (1H, dd, J=6.7, 15.3 Hz), 4.24 (1H, bs), 3.82–3.91 (2H, m), 3.67 (1H, m), 2.21 (2H, t, J=7.6 Hz), 1.9–2.1 (2H, m), 1.62 (2H, m), 1.2–1.4 (62H, m), 0.88 (6H, t, J=6.7 Hz).

(ii) Synthesis of the compound C3

To a solution of the amide (compound C-b 2, 33.8mg) in tetrahydrofuran (1.5 ml) were added stannous chloride (33 mg), silver perchlorate (36 mg) and powdered Molecular Sieves 4A (140 mg), and the mixture was stirred for 30 minutes. The mixture was next cooled to −10° C., a solution of benzylgalactosyl fluoride (compound A13, 28 mg) in tetrahydrofuran (0.5 ml) was added to it. The resulting mixture was allowed to gradually warm to room temperature. After being stirred for 3 hours, the mixture was diluted with acetone, filtered through celite, and the filtrate was evaporated under reduced pressure. Purification on a silica gel column (Wako Gel C-200, 10 g) eluting with hexane-ethyl acetate (3:1) afforded an α-galactoside (compound C3) in an amount of 19.7 mg (yield, 32.4%).

Data of the compound C3

$[\alpha]^{23}_D$=+25.1° ($CHCl_3$, c=0.47)

MS: FDMS 1173.

IR: ($cm^{-1}$, KBr)

3210, 2920, 2850, 1640, 1590, 1545, 1495, 1465, 1450, 1335, 1290, 1110.

mp: 63.0–64.5° C.

NMR: $^1$H (500 MHz, $CDCl_3$; 27° C.)

δ (ppm)

7.23–7.37 (20H, m), 6.40 (1H, d, J=7.9 Hz), 5.65 (1H, m), 5.42 (1H, dd, J=6.1, 15.3 Hz), 4.91, 4.85, 4.70, 4.55, 4.47 & 4.38 (each 1H, d, J=11.6 Hz), 4.75 (2H, s), 4.12 (1H, m), 3.95–4.06 (3H, m), 3.79–3.92 (3H, m), 3.4–3.71 (3H, m), 2.12 (2H, dt, J=3.4, 7.6 Hz), 1.90–2.01 (3H, m), 1.1–1.6 (63H, m), 0.88 (6H, t, J=6.7 Hz).

(iii) Synthesis of the compound 1

To a solution of the α-galactoside (compound C3, 9.7 mg) in tetrahydrofuran (1.0 ml) was added a 5% palladium on barium sulfate (5 mg). After the reaction vessel was purged with hydrogen, the mixture was stirred at room temperature for 16 hours, and then filtered through celite. The filtrate was concentrated and purified on a silica gel column (Wako Gel C-200, 10 g, chloroform-methanol (10:1)) to give the compound 1 in an amount of 3.0 mg (yield, 44.5 mg).

Data of the compound 1

$[\alpha]^{23}_D$=+50.0° (pyridine, c=0.26)

MS: FDMS 814.

IR: ($cm^{-1}$, KBr)

3260, 2910, 2850, 1645, 1545, 1470, 1350, 1125, 1065.

mp: 184.5–186.5° C.

NMR: $^1$H (500 MHz, $C_5D_5N$; 27° C.)

δ (ppm)

8.52 (1H, d, J=8.6 Hz), 5.46 (1H, d, J=3.7 Hz), 4.74 (1H, m), 4.66 (1H, dd, J=3.6, 9.8 Hz), 4.54–4.60 (2H, m), 4.40–4.52 (4H, m), 4.37 (1H, dd, J=5.5, 10.4 Hz), 4.29 (1H, m), 2.48 (2H, t, J=7.3 Hz), 1.8–2.0 (4H, m), 1.58 (1H, m), 1.20–1.45 (65H, m), 0.881 & 0.877 (each 3H, t, J=7.3 Hz).

$^{13}$C (125 MHz, $C_5D_5N$; 27° C.)

δ (ppm)

173.4 (s), 102.2 (d), 73.1 (d), 71.9 (d), 71.7 (d), 71.0 (d), 70.5 (d), 69.7 (t), 62.7 (t), 54.9 (d), 36.8 (t), 35.1 (t), 32.1 (t), 30.2 (t), 30.1 (t), 30.0 (t), 29.9 (t), 29.83 (t), 29.76 (t), 29.6 (t), 26.6 (t), 26.4 (t), 22.9 (t), 14.3 (q).

Figure 9:
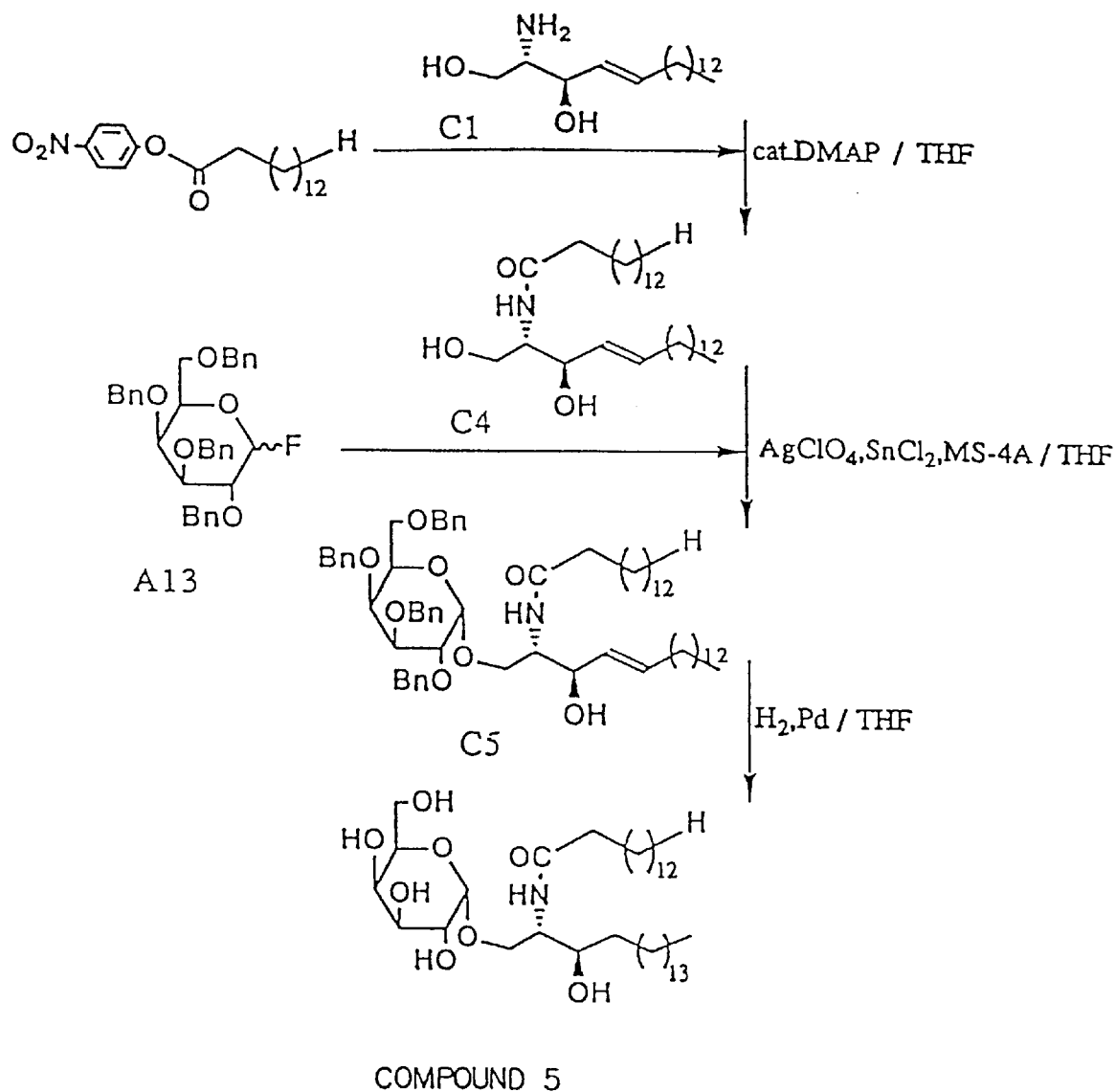
FIG. 9 shows the scheme which illustrates another preferred method for synthesizing the compound 5.

[Synthesis of the compound 5 (FIG. 9)]

Abbreviations in the aforementioned scheme are the same as those in the previously described schemes.

(i) Synthesis of the compound C4

To a solution of sphingosine (75 mg) in tetrahydrofuran (1.5 ml) were added p-nitrophenyl myristate (175 mg) and 4-dimethylaminopyridine (7.6 mg), and the mixture was stirred at 46° C. for 12 hours. The reaction mixture was concentrated directly and purified on a silica gel column (Wako Gel C-200, 10 g, hexane-acetone (3:1)) to give an amide (compound C4) in an amount of 112.6 mg (yield, 88.3%).

Data of the compound C4

$[\alpha]^{23}_D$=−11.4° (pyridine, c=0.58)

MS: FDMS 510.

IR: ($cm^{-1}$, KBr)

3300, 2910, 2850, 1640, 1620, 1550, 1470, 1380, 1265, 1240, 1040.

mp: 96.5–98.0° C.

NMR: $^1$H (500 MHz, $C_5D_5N$; 27° C.)

δ (ppm)

8.33 (1H, d, J=8.5 Hz), 6.7 (1H, m), 6.05 (1H, dd, J=6.4, 15.9 Hz), 5.96 (1H, dt, J=6.4, 15.9 Hz), 4.85 (1H, t, J=6.7 Hz), 4.75 (1H, m), 4.47 (1H, dd, J=4.9, 11.0 Hz), 4.30 (1H, dd, J=4.0, 10.7 Hz), 2.47 (2H, t, J=7.6 Hz), 2.10 (2H, m), 1.85 (2H, m), 1.39 (4H, m), 1.20–1.33 (38H, m), 0.88 (6H, t, J=6.7 Hz).

$^{13}$C (125 MHz, $C_5D_5N$; 27° C.)

δ (ppm)

173.5 (s), 132.4 (d), 132.3 (d), 73.3 (d), 62.2 (t), 56.9 (d), 36.9 (t), 32.7 (t), 32.1 (t), 29.99 (t), 29.96 (t), 29.93 (t), 29.87 (t), 29.8 (t), 29.7 (t), 26.61 (t), 29.55 (d), 26.4 (t), 22.9 (t), 14.3 (q).

(ii) Synthesis of the compound C5

To a solution of the amide (compound C4, 106.8 mg) in tetrahydrofuran (4.5 ml) was added a powdered Molecular Sieves 4A (400 mg), and the mixture was stirred for 10 minutes. Stannous chloride (133 mg) and silver perchlorate (146 mg) were added, and the mixture was further stirred for 30 minutes. The reaction mixture was cooled to −10° C., and a solution of benzylgalactosyl fluoride (compound A13, 113 mg) in tetrahydrofuran (1.5 ml) was added thereto. After 30 minutes, it was allowed to warm to room temperature, stirred for 30 minutes, and then diluted with chloroform-methanol (1:1), filtered through celite, and the filtrate was evaporated under reduced pressure. Purification of the residue on a silica gel column (Wako Gel C-200, 15 g) eluting with hexane-ethyl acetate (5:2) afforded an α-galactoside (compound C5) in an amount of 76.0 mg (yield, 35.2%).

Data of the compound C5

$[\alpha]^{24}_D$=+32.7° (CHCl$_3$, c=2.26)

MS: FDMS 1033.

IR: (cm$^{-1}$, KBr)

3320, 2920, 2850, 1640, 1615, 1545, 1465, 1450, 1350, 1105, 1045.

mp: 66.0–68.0° C.

NMR: $^1$H (500 MHz, CDCl$_3$; 27° C.)

δ (ppm)

7.25–7.37 (20H, m), 6.40 (1H, d, J=7.9 Hz), 5.66 (1H, dt, J=7.9, 15.3 Hz), 5.42 (1H, dd, J=5.5, 15.3 Hz), 4.91, 4.85, 4.70, 4.55, 4.47 & 4.38 (each 1H, d, J=11.6 Hz), 4.752 (2H, s), 4.747 (1H, d, J=4.9 Hz), 4.13 (1H, m), 4.03 (1H, dd, J=3.7, 10.4 Hz), 3.95–4.01 (2H, m), 3.79–3.89 (4H, m), 3.69 (1H, dd, J=3.7, 10.3 Hz), 3.45–3.55 (2H, m), 2.12 (2H, dt, J=3.7, 7.9 Hz), 1.99 (2H, m), 1.58 (2H, m), 1.2–1.4 (42H, m), 0.88 (6H, t, J=7.0 Hz).

$^{13}$C (125 MHz, CDCl$_3$; 27° C.)

δ (ppm)

173.3 (s), 138.5 (s), 138.4 (s), 138.0 (s), 137.6 (s), 133.0 (d), 129.2 (d), 128.44 (d), 128.41 (d), 128.3 (d), 128.13 (d), 128.10 (d), 127.90 (d), 127.86 (d), 127.6 (d), 127.4 (d), 126.1 (d), 99.1 (d), 79.2 (d), 75.9 (d), 74.8 (t), 74.4 (d), 74.2 (t), 74.0 (d), 73.6 (t), 72.2 (t), 69.8 (d), 69.0 (t), 68.7 (t), 52.8 (d), 36.7 (t), 32.3 (t), 31.9 (t), 29.68 (t), 29.65 (t), 29.5 (t), 29.41 (t), 29.36 (t), 29.32 (t), 29.26 (t), 25.8 (t), 22.7 (t), 14.1 (q).

(iii) Synthesis of the compound 5

To a solution of the galactoside (compound 5, 7.3 mg) in tetrahydrofuran (2.0 ml) was added palladium black (1.5 mg). After the reaction vessel was purged with hydrogen, the mixture was stirred at room temperature for 16 hours, and then filtered through celite. The filtrate was concentrated to give a crude product. Purification on a silica gel column (Wako Gel C-200, 2 g) eluting with chloroform-methanol (8:1) afforded the compound 5 in an amount of 4.4 mg (yield, 90.0%).

Data of the compound 5 was the same as those described above.

The compounds other than those described above (1–14) were synthesized by using appropriate carboxylic acids or combining Wittig's salts having alkyl groups of a variety of lengths in accordance with the synthetic methods of the compounds (9, 7, 5, 1) (synthetic routes A–C). The compounds 15, 35 and 29 had double bonds unreduced by conducting the reduction at the final stage with liquid ammonia and metallic sodium. Examples of the synthesis of these compounds are illustrated below.

Compound 2

The compound 2 was obtained by reacting the sphingosine C1 with p-nitrophenyl docosanoate in place of p-nitrophenyl tetracosanoate in the synthesis of the compound 1 and conducting synthesis by applying the route C.

As an alternative method, the compound 2 was obtained by reacting the amine B4 with p-nitrophenyl docosanoate in place of p-nitrophenyl octanoate in the synthesis of the compound 7 and conducting synthesis by applying the route B.

[Data]

$[\alpha]^{25}_D$=+50.7° (CHCl$_3$, c=0.82)

MS: FDMS 787.

IR: (cm$^{-1}$, KBr)

3390, 3220, 2870, 2810, 1635, 1535, 1455, 1080, 1055.

mp: 147.0–149.5° C.

NMR: $^1$H (500 MHz, C$_5$D$_5$N; 27° C.)

δ (ppm)

8.53 (1H, d, J=8.6 Hz), 5.46 (1H, d, J=3.1 Hz), 4.74 (1H, m), 4.66 (1H, m), 4.4–4.6 (6H, m), 4.37 (1H, dd, J=5.8, 10.1 Hz), 4.29 (1H, m), 2.48 (2H, t, J=7.3 Hz), 1.80–1.97 (4H, m), 1.58 (1H, m), 1.20–1.45 (61H, m), 0.880 & 0.876 (each 3H, t, J=7.3 Hz).

$^{13}$C (125 MHz, C$_5$D$_5$N; 27° C.)

δ (ppm)

173.4 (s), 102.2 (d), 73.1 (d), 72.0 (d), 71.7 (d), 71.0 (d), 70.6 (d), 69.7 (t), 62.7 (t), 54.9 (d), 36.8 (t), 35.1 (t), 32.1 (t), 30.2 (t), 30.1 (t), 30.0 (t), 29.95 (t), 29.92 (t), 29.83 (t), 29.76 (t), 29.62 (t), 29.61 (t), 26.6 (t), 26.4 (t), 22.9 (t), 14.3 (q).

Compound 3

The compound 3 was obtained by reacting the sphingosine C1 with p-nitrophenyl icosanoate in place of p-nitrophenyl tetracosanoate in the synthesis of the compound 1 and conducting synthesis by applying the route C.

As an alternative method, the compound 3 was obtained by reacting the amine b4 with p-nitrophenyl icosanoate in place of p-nitrophenyl octanoate in the synthesis of the compound 7 and conducting further synthesis by applying the route B.

[Data]

$[\alpha]^{25}_D$=+47.3° (pyridine, c=1.76)

MS: FDMS 759.

IR: (cm$^{-1}$, KBr)

3390, 3220, 2870, 2880, 2810, 1635, 1530, 1455, 1080, 1055.

mp: 151.5–153.0° C.

NMR: $^1$H (500 MHz, C$_5$D$_5$N; 27° C.)

δ (ppm)

8.52 (1H, d, J=8.6 Hz), 5.46 (1H, d, J=4.3 Hz), 4.73 (1H, m), 4.66 (1H, dd, J=4.5, 10.1 Hz), 4.4–4.6 (6H, m), 4.37 (1H, dd, J=5.5, 10.4 Hz), 4.29 (1H, m), 2.48 (2H, t, J=7.3 Hz), 1.80–1.97 (4H, m), 1.58 (1H, m), 1.20–1.42 (57H, m), 0.879 & 0.876 (each 3H, t, J=7.3 Hz).

$^{13}$C (125 MHz, C$_5$D$_5$N; 27° C.)

δ (ppm)

173.4 (s), 102.1 (d), 73.1 (d), 71.9 (d), 71.6 (d), 71.0 (d), 70.5 (d), 69.7 (t), 62.7 (t), 54.9 (d), 36.8 (t), 35.1 (t), 32.1 (t), 30.2 (t), 30.1 (t), 30.0 (t), 29.9 (t), 29.8 (t), 29.7 (t), 29.6 (t), 26.6 (t), 26.4 (t), 22.9 (t), 14.3 (q).

Compound 4

The compound 4 was obtained by reacting the sphingosine C1 with p-nitrophenyl stearate in place of p-nitrophenyl tetracosanoate in the synthesis of the compound 1 and conducting further synthesis by applying the route C.

As an alternative method, the compound 4 was obtained by reacting the amine B4 with p-nitrophenyl stearate in place of p-nitrophenyl octanoate in the synthesis of the compound 7 and conducting further synthesis by applying the route B.

[Data]
$[\alpha]^{25}_D$=+55.5° (pyridine, c=0.84)
MS: FDMS 731.
IR: (cm$^{-1}$, KBr)
3230, 2940, 2830, 1640, 1540, 1465, 1345, 1120, 1090, 1060.
mp: 157.5–159.5° C.
NMR: $^1$H (500 MHz, C$_5$D$_5$N; 27° C.)
δ (ppm)
8.52 (1H, d, J=8.6 Hz), 5.46 (1H, d, J=3,7 Hz), 4.73 (1H, m), 4.66 (1H, dd, J=3.7, 9.8 Hz), 4.57 (1H, d, J=2.5 Hz), 4.55 (1H, t, J=6.1 Hz), 4.40–4.51 (4H, m), 4.37 (1H, dd, J=5.8, 10.7 Hz), 4.29 (1H, m), 2.48 (2H, t, J=7.3 Hz), 1.80–1.96 (4H, m), 1.59 (1H, m), 1.2–1.44 (53H, m), 0.88 (6H, t, J=6.7 Hz).
$^{13}$C (125 MHz, C$_5$D$_5$N; 27° C.)
δ (ppm)
173.4 (s), 102.1 (d), 73.1 (d), 71.9 (d), 71.7 (d), 71.0 (d), 70.5 (d), 69.7 (t), 62.7 (t), 54.9 (d), 36.8 (t), 35.1 (t), 32.1 (t), 30.2 (t), 30.1 (t), 30.0 (t), 29.9 (t), 29.8 (t), 29.7 (t), 29.6 (t), 26.6 (t), 26.4 (t), 22.9 (t), 22.8 (t), 14.3 (q).

Compound 6

The compound 6 was obtained by reacting the sphingosine C1 with p-nitrophenyl decanoate in place of p-nitrophenyl tetracosanoate in the synthesis of the compound 1 and conducting further synthesis by applying the route C.

As an alternative method, the compound 6 was obtained by reacting the amine B4 with p-nitrophenyl decanoate in place of p-nitrophenyl octanoate in the synthesis of the compound 7 and conducting further synthesis by applying the route B.

[Data]
$[\alpha]^{25}_D$=+54.8° (pyridine, c=0.93)
MS: FDMS 619.
IR: (cm$^{-1}$, KBr)
3245, 2900, 2840, 1635, 1540, 1460, 1345, 1120, 1090, 1060.
mp: 151.0–154.0° C.
NMR: $^1$H (500 MHz, C$_5$D$_5$N; 27° C.)
δ (ppm)
8.52 (1H, d, J=9.2 Hz), 6.14 (1H, m), 5.45 (1H, d, J=3.7 Hz), 4.74 (1H, m), 4.65 (1H, dd, J=4.0, 10.1 Hz), 4.57 (1H, d, J=3.4 Hz), 4.54 (1H, t, J=5.8 Hz), 4.40–4.50 (4H, m), 4.36 (1H, dd, J=5.5, 11.0 Hz), 4.28 (1H, m), 2.47 (2H, dt, J=1.5, 7.6 Hz), 1.80–1.95 (4H, m), 1.57 (1H, m), 1.15–1.40 (37H, m), 0.87 & 0.85 (each 3H, t, J=6.7 Hz).
$^{13}$C (125 MHz, C$_5$D$_5$N; 27° C.)
δ (ppm)
173.4 (s), 102.1 (d), 73.1 (d), 71.9 (d), 71.6 (d), 71.0 (d), 70.5 (d), 69.7 (t), 62.7 (t), 54.9 (d), 36.8 (t), 35.1 (t), 32.12 (t), 30.05 (t), 30.2 (t), 30.1 (t), 30.0 (t), 29.9 (t), 29.8 (t), 29.7 (t), 29.61 (t), 29.55 (t), 26.6 (t), 26.4 (t), 22.93 (t), 22.90 (t), 14.3 (q).

Compound 8

The compound 8 was obtained by reacting the sphingosine C1 with acetic anhydride in place of p-nitrophenyl tetracosanoate in the synthesis of the compound 1 and conducting further synthesis by applying the route C.

As an alternative method, the compound 8 was obtained by reacting the amine B4 with acetic anhydride in place of p-nitrophenyl octanoate in the synthesis of the compound 7 and conducting further synthesis by applying the route B.

[Data]
$[\alpha]^{25}_D$=+74.3° (pyridine, c=1.36)
MS: FDMS 507.
IR: (cm$^{-1}$, KBr)
3230, 2890, 2830, 1630, 1540, 1465, 1370, 1140.
mp: 171.0–172.0° C.
NMR: $^1$H (500 MHz, C$_5$D$_5$N; 27° C.)
δ (ppm)
8.63 (1H, d, J=8.6 Hz), 6.1 (2H, m), 5.43 (1H, d, J=3.7 Hz), 4.70 (1H, m), 4.64 (1H, dd, J=4.0, 10.1 Hz), 4.55 (1H, d, J=2.4 Hz), 4.52 (1H, t, J=6.1 Hz), 4.46 (1H, dd, J=3.7, 10.4 Hz), 4.38–4.44 (3H, m), 4.31 (1H, dd, J=6.1, 10.4 Hz), 4.26 (1H, m), 2.13 (3H, s), 1.77–1.90 (3H, m), 1.55 (1H, m), 1.20–1.40 (24H, m), 0.87 (3H, t, J=7.0 Hz).
$^{13}$C (125 MHz, C$_5$D$_5$N; 27° C.)
δ (ppm)
170.3 (s), 102.0 (d), 73.0 (d), 71.9 (d), 71.6 (d), 70.9 (d), 70.5 (d), 69.4 (t), 62.6 (t), 55.0 (d), 35.0 (t), 32.1 (t), 30.1 (t), 30.04 (t), 29.97 (t), 29.9 (t), 29.6 (t), 26.6 (t), 23.3 (q), 22.9 (t), 14.3 (q).

Compound 10

In the synthesis of the compound 7, the aldehyde A2 was reacted with dodecanetriphenylphosphonium bromide in place of tetradecanetriphenylphosphonium bromide. Next, the amine obtained in the reduction was reacted with p-nitrophenyl myristate in place of p-nitrophenyl octanoate, and synthesis was further conducted by applying the route B to give the compound 10.

[Data]
$[\alpha]^{24}_D$=+74.3° (pyridine, c=0.35)
MS: FDMS 646.
IR: (cm$^{-1}$, KBr)
3250, 2900, 2830, 1640, 1540, 1460, 1120, 1085, 1060.
mp: 153.5–156.0° C.
NMR: $^1$H (500 MHz, C$_5$D$_5$N; 27° C.)
δ (ppm)
8.52 (1H, d, J=8.6 Hz), 6.1 (1H, m), 5.47 (1H, d, J=3.7 Hz), 4.75 (1H, m), 4.67 (1H, dd, J=3.7, 9.8 Hz), 4.34–4.60 (7H, m), 4.29 (1H, m), 2.48 (2H, dt, J=1.2, 7.3 Hz), 1.80–1.95 (4H, m), 1.58 (1H, m), 1.20–1.42 (41H, m), 0.87 (6H, t, J=6.8 Hz).
$^{13}$C (125 MHz, C$_5$D$_5$N; 27° C.)
δ (ppm)
173,4 (s), 102.1 (d), 73.1 (d), 72.0 (d), 71.7 (d), 71.0 (d), 70.6 (d), 69.7 (t), 62.7 (t), 54.9 (d), 36.8 (t), 35.1 (t), 32.1 (t), 30.2 (t), 30.1 (t), 30.00 (t), 29.97 (t), 29.9 (t), 29.8 (t), 29.7 (t), 29.6 (t), 26.6 (t), 26.4 (t), 22.9 (t), 14.3 (q).

Compound 11

In the synthesis of the compound 10, the (2S,3S)-aldehyde was used in place of the aldehyde A2, and the synthesis was conducted by applying the route B to give the compound 11.

[Data]
$[\alpha]^{24}_D$=+62.0° (pyridine, c=0.50)
MS: FDMS 646.
IR: (cm$^{-1}$, KBr)
3290, 2910, 2840, 1640, 1615, 1540, 1456, 1140, 1050.
mp: 145.0–147.0° C.
NMR: $^1$H (500 MHz, C$_5$D$_5$N; 27° C.)
δ (ppm)
8.40 (1H, d, J=8.5 Hz), 6.28 (1H, m), 5.47 (1H, d, J=3.7 Hz), 4.66–4.76 (3H, m), 4.10–4.62 (7H, m), 2.48 (2H, dt, J=1.8, 7.3 Hz), 1.80–2.00 (3H, m), 1.70 (1H, m), 1.57 (1H, m), 1.20–1.42 (41H, m), 0.88 (6H, t, J=6.7 Hz).

Compound 12

In the synthesis of the compound 10, the (2S, 3R)-aldehyde was used in place of the aldehyde A2, and the synthesis was conducted by applying the route B to give the compound 12.

[Data]
$[\alpha]^{23}_D$=+52.5° (pyridine, c=0.75)
MS: FDMS 646.
IR: (cm$^{-1}$, KBr)
3480, 3240, 2910, 2840, 1630, 1560, 1460, 1070, 1005.
mp: 148.5–152.5° C.
NMR: $^1$H (500 MHz, C$_5$D$_5$N; 27° C.)
δ (ppm)
8.10 (1H, d, J=8.6 Hz), 5.46 (1H, d, J=3.7 Hz), 4.79 (1H, m), 4.66 (1H, dd, J=3.7, 9.8 Hz), 4.34–4.56 (7H, m), 4.12 (1H, t, J=6.1 Hz), 4.07 (1H, dd, J=6.1, 9.8 Hz), 2.49 (2H, t, J=6.5 Hz), 1.75–1.92 (3H, m), 1.69 (1H, m), 1.55 (1H, m), 1.20–1.42 (41H, m), 0.88 (6H, t, J=6.7 Hz).
$^{13}$C (125 MHz, C$_5$D$_5$N; 27° C.)
δ (ppm)
173.6 (s), 101.4 (d), 73.0 (d), 71.8 (d), 71.1 (d), 70.6 (d), 70.4 (d), 69.8 (t), 62.8 (t), 53.1 (d), 36.8 (t), 35.3 (t), 32.1 (t), 30.2 (t), 30.0 (t), 29.93 (t), 29.89 (t), 29.8 (t), 29.7 (t), 29.6 (t), 26.6 (t), 26.5 (t), 22.9 (t), 14.3 (q).

Compound 13

In the synthesis of the compound 10, the (2R, 3S)-aldehyde was used in place of the aldehyde A2, and the synthesis was conducted by applying the route B to give the compound 13.

[Data]
$[\alpha]^{24}_D$=+80.7° (pyridine, c=0.27)
MS: FDMS 646.
IR: (cm$^{-1}$, KBr)
3300, 2900, 2820, 1635, 1520, 1460, 1065, 1005.
mp: 149.0–150.5° C.
NMR: $^1$H (500 MHz, C$_5$D$_5$N; 27° C.)
δ (ppm)
8.04 (1H, d, J=8.6 Hz), 6.4 (1H, m), 5.49 (1H, d, J=3.7 Hz), 4.80 (1H, m), 4.68 (1H, dd, J=3.7, 9.8 Hz), 4.65 (1H, bd, J=2.4 Hz), 4.36–4.58 (6H, m), 4.16 (1H, dd, J=6.7, 10.4 Hz), 2.50 (2H, t, J=7.3 Hz), 1.75–1.92 (3H, m), 1.69 (1H, m), 1.53 (1H, m), 1.20–1.42 (41H, m), 0.88 (6H, t, J=7.0 Hz).

Compound 14

The compound 14 was obtained by reacting the sphingosine C1 with p-nitrophenyl (R)-2-acetoxytetracosanoate in place of p-nitrophenyl tetracosanoate in the synthesis of the compound 1 and further conducting the synthesis by applying the route C.

As an alternative method, the compound 14 was obtained by reacting the amine B4 with p-nitrophenyl (R)-2-acetoxytetracosanoate in place of p-nitrophenyl octanoate in the synthesis of the compound 7 and conducting further synthesis by applying the route B.

[Data]
MS: FDMS 831.
NMR: $^1$H (500 MHz, C$_5$D$_5$N; 27° C.)
δ (ppm)
8.45 (1H, d, J=9.2 Hz), 5.44 (1H, d, J=3.7 Hz), 4.71 (1H, m), 4.64 (2H, m), 4.53 (3H, m), 4.40 (3H, m), 4.25 (1H, m), 2.22 (1H, m), 2.09 (1H, m), 1.70–1.95 (4H, m), 1.54 (1H, m), 1.2–1.45 (63H, m), 0.884 & 0.876 (each 3H, t, J=6.7 Hz).
$^{13}$C (125 MHz, C$_5$D$_5$N; 27° C.)
δ (ppm)
175.1 (s), 101.9 (d), 73.2 (d), 72.4 (d), 71.7 (d), 71.0 (d), 70.5 (d), 69.4 (t), 62.7 (t), 54.1 (d), 35.6 (t), 35.2 (t), 32.1 (t), 30.3 (t), 30.04 (t), 29.97 (t), 29.9 (t), 29.64 (t), 29.61 (t), 26.5 (t), 25.8 (t), 22.9 (t), 14.3 (q).

Compound 15

The compound 15 was obtained by reacting the sphingosine C1 with p-nitrophenyl stearate in place of p-nitrophenyl tetracosanoate in the synthesis of the compound 1 and further conducting the synthesis by applying the route C. The compound 15 as the deprotected derivative was obtained by conducting the deprotection in the final step by wetting the raw material with a small amount of tetrahydrofuran and adding thereto liquid ammonia and next metallic sodium.

[Data]
$[\alpha]^{25}_D$=+41.4° (pyridine, c=0.14)
MS: FDMS 729.
IR: (cm$^{-1}$, KBr)
3230, 2880, 2810, 1630, 1535, 1460, 1375, 1065, 1040.
mp: 169.0–172.0° C.
NMR: $^1$H (500 MHz, C$_5$D$_5$N; 27° C.)
δ (ppm)
8.50 (1H, d, J=8.6 Hz), 6.01 (2H, bs), 5.47 (1H, d, J=3.7 Hz), 4.86 (2H, m), 4.67 (1H, dd, J=4.0, 10.1 (Hz), 4.59 (1H, d, J=2.4 Hz), 4.54 (1H, t, J=5.8 Hz), 4.40–4.50 (5H, m), 4.37 (1H, m), 2.46 (2H, dt, J=3.1, 7.6 Hz), 2.09 (2H, bs), 1.84 (2H, m), 1.15–1.45 (50H, m), 0.88 (6H, t, J=6.4 Hz).

Compound 29

The synthesis was conducted by reacting the amine A7 with oleic acid in place of tetracosanoic acid in the synthesis of the compound 9 and further continuing the synthesis by applying the route C. The compound 29 as the deprotected derivative was obtained by conducting the deprotection in the final step by wetting the raw material with a small amount of tetrahydrofuran and then adding thereto liquid ammonia and metallic sodium.

[Data]
$[\alpha]^{24}_D$=+46.4° (pyridine, c=0.17)
MS: FDMS 728.
IR: (cm$^{-1}$, KBr)
3400, 2900, 2820, 1640, 1540, 1460, 1060.
mp: 134–136° C.
NMR: $^1$H (500 MHz, C$_5$D$_5$N; 27° C.)
δ (ppm)
8.52 (1H, d, J=8.6 Hz), 6.54 (1H, bs), 6.45 (1H, bs), 6.35 (1H, bs), 6.15 (1H, bs), 5.44 (3H, m), 4.73 (1H, m), 4.66 (1H, dd, J=3.7, 9.8 Hz), 4.33–4.58 (7H, m), 4.27 (1H, m), 2.45 (2H, m), 2.06 (3H, m), 1.75–1.92 (2H, m), 1.55 (1H, m), 1.14–1.42 (48H, m), 0.84 (6H, m).
$^{13}$C (125 MHz, C$_5$D$_5$N; 27° C.)
δ (ppm)
173.3 (s), 130.1 (d), 130.1 (d), 102.0 (d), 73.0 (d), 71.8 (d), 71.6 (d), 70.9 (d), 70.4 (d), 69.6 (t), 62.6 (t), 54.9 (d), 36.7 (t), 35.0 (t), 32.0 (t), 32.0 (t), 30.1 (t), 30.0 (t), 29.9 (t), 29.8 (t), 29.7 (t), 29.5 (t), 29.6 (t), 29.5 (t), 29.5 (t), 29.4 (t), 27.4 (t), 26.5 (t), 26.3 (t), 22.9 (t), 14.2 (q).

Compound 35

The synthesis was conducted by reacting the sphingosine C1 with p-nitrophenyl myristate in place of p-nitrophenyl tetracosanoate in the synthesis of the compound 1 and further by applying the route C. The compound 29 as the deprotected derivative was obtained by conducting the deprotection in the final step by wetting the raw material with a small amount of tetrahydrofuran and then adding thereto liquid ammonia and metallic sodium.

[Data]
$[\alpha]^{24}_D$=+48.9° (pyridine, c=0.45)
MS: FDMS 673.
IR: (cm$^{-1}$, KBr)
3320, 2920, 2855, 1640, 1545, 1470, 1345, 1150.
mp: 158.0–160.0° C.
NMR: $^1$H (500 MHz, C$_5$D$_5$N; 27° C.)
δ (ppm)
8.46 (1H, d, J=7.3 Hz), 6.59 (1H, m), 6.41 (1H, m), 6.33 (1H, m), 6.00 (2H, bs), 5.46 (1H, d, J=3.7 Hz), 4.85 (2H, m), 4.65 (1H, dd, J=3.7, 9.8 Hz), 4.58 (1H, m), 4.53 (1H, t, J=6.1 Hz), 4.40–4.50 (4H, m), 4.35 (1H, dd, J=5.2, 10.1 Hz), 2.45 (2H, dt, J=3.1, 7.3 Hz), 2.08 (2H, m), 1.84 (2H, m), 1.37 (4H, m), 1.20–1.32 (38H, m), 0.88 (6H, t, J=6.7 Hz).
$^{13}$C (125 MHz, C$_5$D$_5$N; 27° C.)
δ (ppm)
173.5 (s), 132.4 (d), 132.0 (d), 102.1 (d), 73.0 (d), 71.7 (d), 70.9 (d), 70.6 (d), 69.4 (t), 62.7 (t), 55.1 (d), 36.8 (t), 32.7 (t), 32.1 (t), 30.01 (t), 29.9 (t), 29.96 (t), 29.63 (t), 29.87 (t), 29.83 (t), 29.76 (t), 29.73 (t), 29.6 (t), 26.4 (t), 22.9 (t), 14.2 (q).

(4) Synthetic route D

Figure 10A:
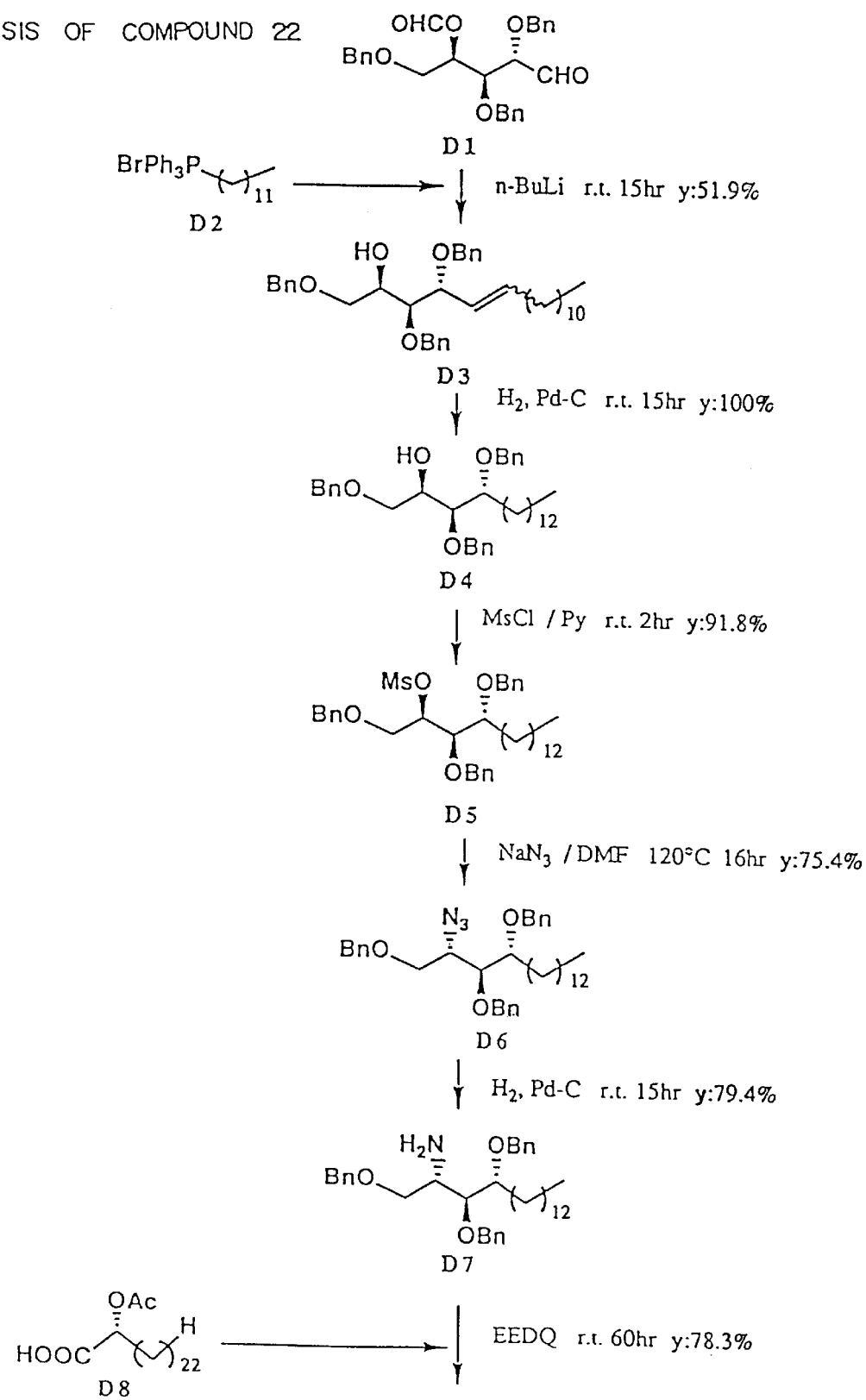
FIG. 10(*a–c*) shows the scheme which illustrates a preferred method for synthesizing the compound 22 ((2S,3S,4R)-1-(α-D-galactopyranosyloxy)-2-[(R)-2-hydroxyltetracosanoylamino]-3,4-heptadecanediol).
Figure 10B:
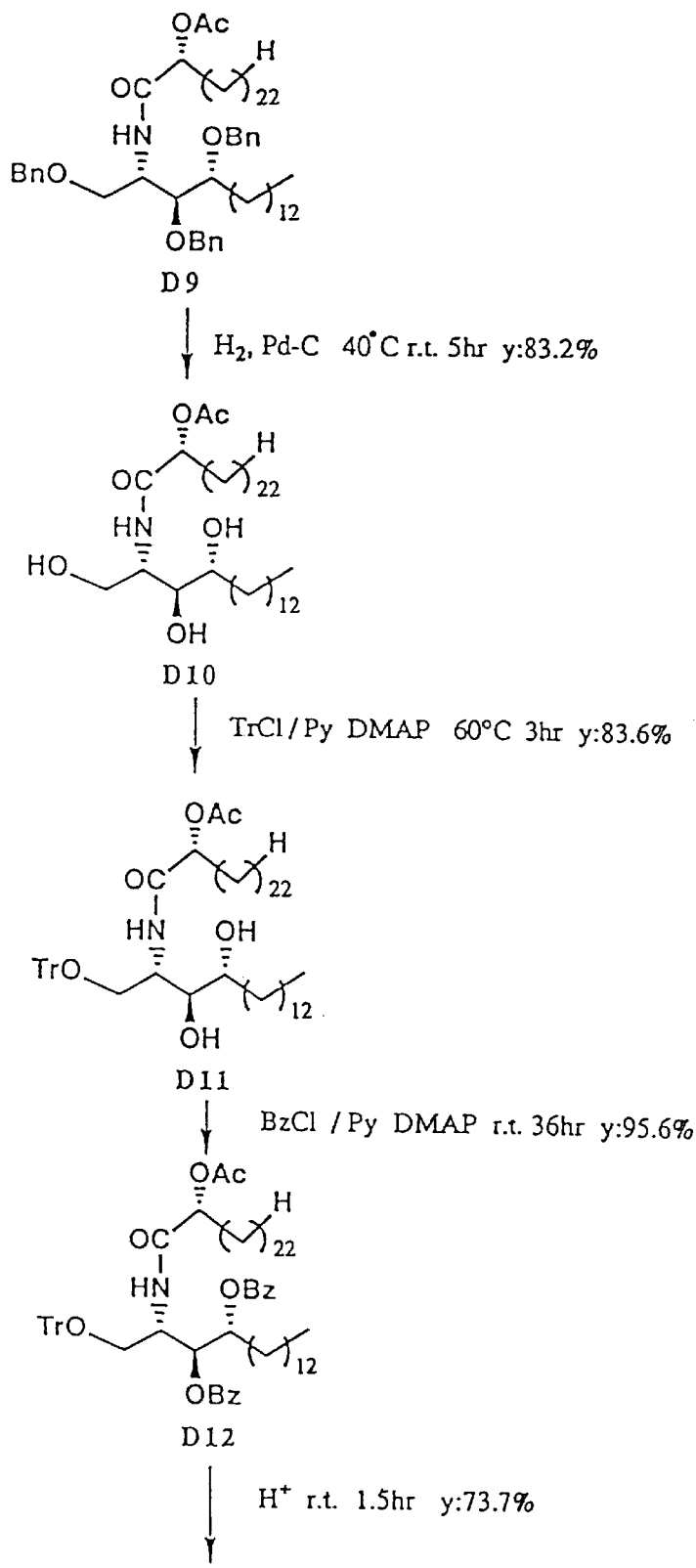
Figure 10C:
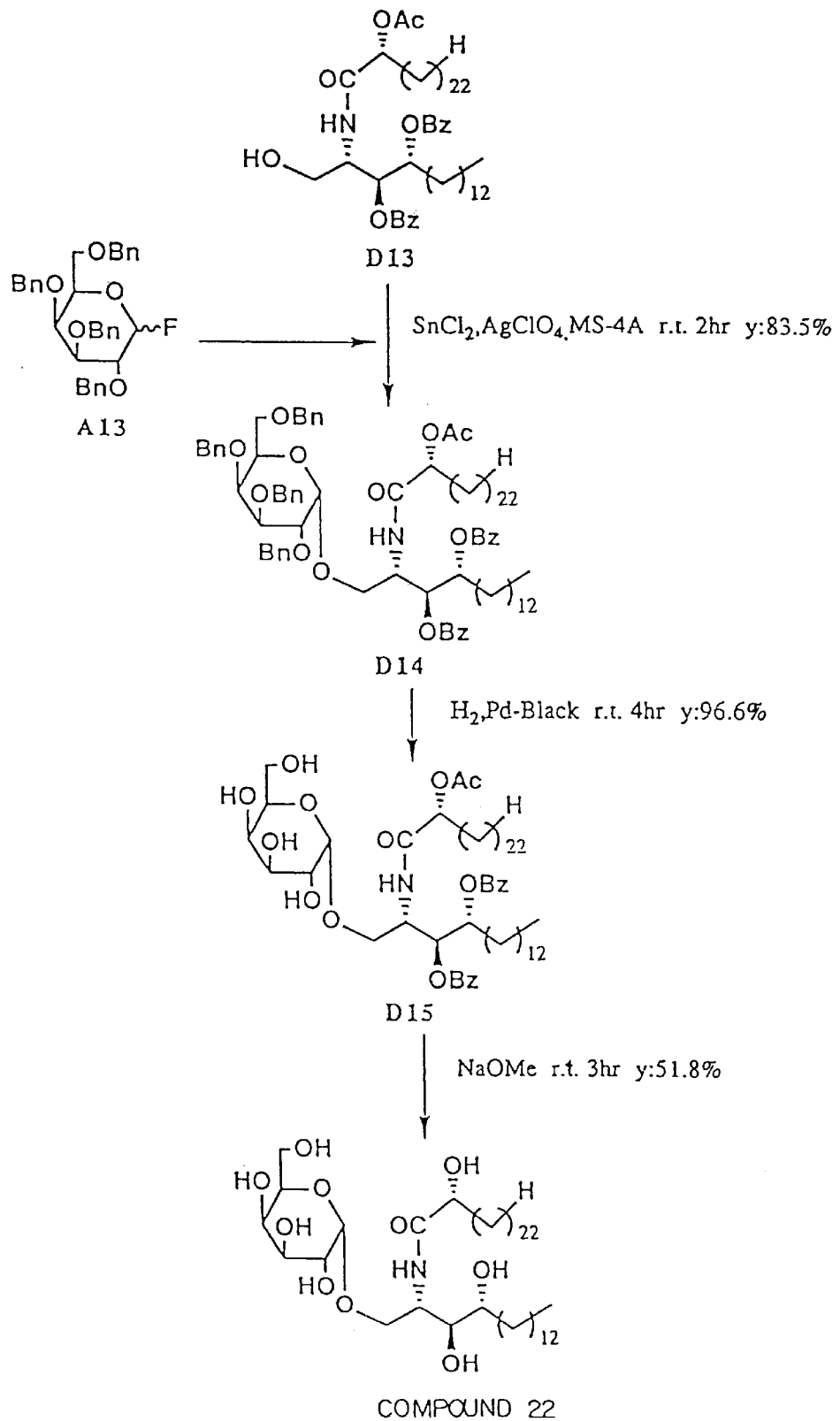

The specific method for synthesizing a compound having a hydroxyl group at C-4 of the long chain base in formula (A) can be illustrated by the following reaction route scheme. Although the reaction route scheme specifically illustrates the method with reference to the compound 22, the compounds according to the present invention including 16–34 and 36–37 except for 22 and 29 can also be synthesized by applying the method (synthesis of the compound 22 (FIGS. 10a–10c)).

In the aforementioned scheme, the following abbreviations are used:
EEDQ: 2-ethoxy-1-ethoxycarbonyl-1,2-dihydroquinoline.

The other abbreviations are the same as those in the previous reaction schemes.

(i) Synthesis of the compound D1

The compound D1 can be synthesized by applying the method described in Agricultural and Biological Chemistry, 54 (3), 663–667, 1990.

(ii) synthesis of the compound D3

To the Wittig's salt (compound D2, 32.07 g) was added tetrahydrofuran (40 ml), and the reaction vessel was purged with argon. A 2 N solution of n-butyl lithium in hexane (30 ml) was added, and the mixture was stirred for 15 minutes. A solution of the aldehyde (compound D1, 13.18 g) in tetrahydrofuran (20 ml) was dropwise added to the mixture, which was then allowed to warm to room temperature and stirred for 15 hours. To the reaction mixture were added methanol (3 ml) followed by 20% aqueous methanol (300 ml), and the mixture was extracted thrice with n-hexane. The extracts were washed with brine and concentrated. Purification on a silica gel column (Wako Gel C-200, 400 g) eluting with hexane-ethyl acetate (9:1) afforded an alcohol (compound D3) in an amount of 9.31 g (yield, 51.9%).

Data of the compound D3
$[\alpha]^{24}_D$=-38.2° (CHCl$_3$, c=1.0)
MS: FDMS 573, 301.
NMR: $^1$H (500 MHz, CDCl$_3$; 27° C.)
δ (ppm)
7.20–7.35 (15H, m), 5.72 (1H, m), 5.46 (1H, bt, J=9.2 Hz), 4.68 (1H, d, J=11.2 Hz), 4.60 (1H, d, J=11.7 Hz), 4.47–4.52 (3H, m), 4.44 (1H, dd, J=5.5, 9.8 Hz), 4.33 (1H, d, J=11.7 Hz), 4.08 (1H, m), 3.56 (1H, dd, J=2.4, 5.5 Hz), 3.51 (2H, d, J=6.1 Hz), 3.01 (1H, d, J=5.5 Hz), 1.85–2.01 (2H, m), 1.17–1.36 (18H, m), 0.88 (3H, t, J=6.7 Hz).

(iii) Synthesis of the compound D4

To a solution of the alcohol (compound D3, 931 g) in tetrahydrofuran (30 ml) was added 10% palladium on charcoal (0.53 g). After the reaction vessel was purged with hydrogen, and the mixture was stirred at room temperature for 15 hours, and then filtered through celite. The filtrate was concentrated to give a reduced product (compound D4) in an amount of 9.34 g (yield, quantitatively).

Data of the compound D4
$[\alpha]^{24}_D$=-35.1° (CHCl$_3$, c=0.5)
MS: FDMS 575.
NMR: $^1$H (500 MHz, CDCl$_3$; 27° C.)
δ (ppm)
7.22–7.34 (15H, m), 4.69 (1H, d, J=11.6 Hz), 4.65 (1H, d, J=11.6 Hz), 4.55 (1H, d, J=11.0 Hz), 4.52 (1H, d, J=11.6 Hz), 4.50 (1H, d, J=11.0 Hz), 4.48 (1H, d, J=12.2 Hz), 4.04 (1H, m), 3.68 (1H, m), 3.61 (1H, m), 3.54 (2H, m), 3.17 (1H, d, J=4.9 Hz), 1.85 (3H, m), 1.65 (2H, m), 1.56 (1H, m), 1.41 (1H, m), 1.16–1.35 (17H, m), 0.88 (3H, t, J=7.3 Hz).

(iv) synthesis of the compound D5

To a solution of the reduced product (compound D4, 9.34 g) in pyridine (70 ml) was added methanesulfonyl chloride (2.5 ml), and the mixture was stirred at room temperature for 2 hours, and then concentrated. After the residual acid chloride was distilled azeotropically with toluene, the residue was taken into diethyl ether and washed with brine. The organic layer was concentrated and purified on a silica gel column (Wako Gel C-200, 500 g, hexane-ethyl acetate (9:1)) to give a mesyl derivative (compound D5) in an amount of 9.74 g (yield, 91.8%).

Data of the compound D5
$[\alpha]^{24}_D$=+6.5° (CHCl$_3$, c=1.0)
MS: FDMS 653.
NMR: $^1$H (500 MHz, CDCl$_3$; 27° C.)
δ (ppm)
7.25–7.38 (15H, m), 4.91 (1H, dt, J=3.9, 5.6 Hz), 4.76 (1H, d, J=11.2 Hz), 4.62 (1H, d, J=11.2 Hz), 4.58 (1H, d, J=11.5 Hz), 4.55 (1H, d, J=11.7 Hz), 4.48 (1H, d, J=11.2 Hz), 4.48 (1H, d, J=11.7 Hz), 3.89 (1H, t, J=4.9 Hz), 3.67–3.76 (2H, m), 3.61 (1H, m), 2.91 (3H, s), 1.72 (1H, m), 1.54 (1H, m), 1.41 (1H, m), 1.16–1.35 (21H, m), 0.88 (3H, t, J=7.3 Hz).

(v) Synthesis of the compound D6

To the solution of the mesyl derivative (compound D5, 9.74 g) in dimethylformamide (100 ml) was added sodium azide (9.70 g), and the mixture was stirred at 120° C. for 16 hours, then concentrated, taken into ethyl acetate and washed with water and brine. The organic layer was concentrated and purified on a silica gel column (Wako Gel C-200, 200 g, hexane-ethyl acetate (98:2)) to give an azide derivative (compound D6) in an amount of 6.75 g (yield, 75.4%).

Data of the compound D6
$[\alpha]^{24}_D$=+8.2° (CHCl$_3$, c=1.0)
MS: FDMS 600, 573, 450.
NMR: $^1$H (500 MHz, CDCl$_3$; 27° C.)
δ (ppm)
7.25–7.40 (15H, m), 4.69 (1H, d, J=11.2 Hz), 4.60 (1H, d, J=11.2 Hz), 4.55 (1H, d, J=11.2 Hz), 4.48–4.53 (3H, m), 3.75–3.81 (2H, m), 3.54–3.72 (2H, m), 3.60 (1H, dt, J=3.7, 7.3 Hz), 1.66 (1H, m), 1.56 (1H, m), 1.41 (1H, m), 1.19–1.36 (21H, m), 0.88 (3H, t, J=6.7 Hz).

(vi) Synthesis of the compound D7

To the solution of the azide derivative (compound D6, 605.5 mg) in tetrahydrofuran (6 ml) was added 10% palladium on charcoal (60 mg). After the reaction vessel was purged with hydrogen, the mixture was stirred at room temperature for 15 hours, filtered through celite, and the filtrate was concentrated and purified on a silica gel column (Wake Gel C-200, 30 g, hexane-ethyl acetate (7:3)) to give an amine (compound D7) in an amount of 459.9 mg (yield, 79.4%).

Data of the compound D7
$[\alpha]^{24}_D = -7.0°$ (CHCl$_3$, c=0.5)
MS: FDMS 574.
NMR: $^1$H (500 MHz, CDCl$_3$; 27° C.)
δ (ppm)
7.23–7.36 (15H, m), 4.74 (1H, d, J=11.2 Hz), 4.63 (1H, d, J=11.5 Hz), 4.53 (1H, d, J=11.5 Hz), 4.52 (1H, d, J=11.5 Hz), 4.49 (2H, d, J=1.8 Hz), 3.71 (2H, m), 3.57 (1H, dd, J=3.7, 6.7 Hz), 3.49 (1H, m), 3.16 (1H, m), 1.82 (1H, m), 1.69 (1H, m), 1.58 (1H, m), 1.49 (1H, m), 1.20–1.35 (20H, bs), 0.88 (3H, t, J=7.3 Hz).

(vii) Synthesis of the compound D8

(R)-2-Acetoxytetracosanoic acid (compound D8) is obtained, for example, by reacting (R)-2-α-hydroxytetracosanoic acid which is synthesized by applying the method described in Agricultural and Biological Chemistry, 54 (12), 3337–3338, 1990 with acetic anhydride in pyridine.

Data of the compound D8
$[\alpha]^{20}_D = +8.5°$ (CHCl$_3$, c=1.0)

(viii) Synthesis of the compound D9

The amine (compound D7, 153.3 mg) and (R)-2-acetoxytetracosanoic acid (compound D8, 113.8 mg) were dissolved in tetrahydrofuran (4 ml), and 2-ethoxy-1-ethoxycarbonyl-1,2-dihydroquinoline (EEDQ, 99.0 mg) was added to the solution. The mixture was stirred at room temperature for 60 hours, and then concentrated and purified on a silica gel column (Wake Gel C-200, 10 g, hexane-ethyl acetate (9:1)) to give a benzylceramide (compound D9) in an amount of 205.6 mg (yield, 78.3%).

Data of the compound D9 $[\alpha]^{23}_D = +2.1°$ (CHCl$_3$, c=0.6)
MS: FDMS 983.
NMR: $^1$H (500 MHz, CDCl$_3$; 27° C.)
δ (ppm)
7.22–7.36 (15H, m), 6.50 (1H, d, J=9.2 Hz), 5.05 (1H, dd, J=4.9, 7.3 Hz), 4.82 (1H, d, J=11.6 Hz), 4.62 (1H, d, J=11.6 Hz), 4.55 (1H, d, J=11.6 Hz), 4.52 (1H, d, J=11.6 Hz), 4.42 (2H, s), 4.23 (1H, m), 3.84 (2H, m), 3.51 (1H, m), 3.48 (1H, dd, J=3.7, 9.8 Hz), 1.98 (3H, s), 1.60–1.82 (2H, m), 1.50 (1H, m), 1.20–1.35 (63H, m), 0.88 (6H, t, J=7.3 Hz).

(ix) Synthesis of the compound D10

To the solution of the benzylceramide (compound D9, 317.7 mg) in tetrahydrofuran-n-propanol (1:1) (6 ml) were added 10% palladium on charcoal (167.4 mg) and formic acid (0.6 ml). After the reaction vessel was purged with hydrogen, the mixture was stirred at 40° C. for 5 hours. The reaction mixture was diluted with chloroform (10 ml), filtered through celite, and the filtrate was concentrated. Purification on a silica gel column (Wako Gel C-200, 15 g) eluting with chloroform-methanol (98.2) afforded a ceramide (compound D10) in an amount of 191.6 mg (yield, 83.2%).

Data of the compound D10
$[\alpha]^{23}_D = +6.0°$ (CHCl$_3$, c=0.1)
MS: FDMS 713.
NMR: $^1$H (500 MHz, C$_5$D$_5$N; 27° C.)
δ (ppm)
8.63 (1H, d, J=8.5 Hz), 6.56 (2H, m), 6.13 (1H, bd, J=5.7 Hz), 5.54 (1H, dd, J=5.5, 7.3 Hz), 5.07 (1H, m), 4.47 (1H, m), 4.43 (1H, m), 4.38 (1H, m), 4.28 (1H, m), 2.20 (1H, m), 2.07 (2H, m), 2.04 (3H, s), 1.90 (2H, m), 1.68 (1H, m), 1.15–1.60 (60H, m), 0.85 (6H, t, J=6.7 Hz).

(x) Synthesis of the compound D11

To the solution of the ceramide (compound D10, 99.7 mg) in pyridine (3 ml) were added triphenylmethyl chloride (390.3 mg) and 4-dimethylaminopyridine (5.0 mg), and the mixture was stirred at 60° C. for 3 hours. After dilution with chloroform (30 ml), the mixture was washed with brine and concentrated. Purification on a silica gel column (Wako Gel C-200, 5 g) eluting with chloroform afforded a trityl derivative (compound D11) in an amount of 111.7 mg (yield, 83.6%).

Data of the compound D11
$[\alpha]^{23}_D 32 -13.3°$ (CHCl$_3$, c=0.1)
NMR: $^1$H (500 MHz, CDCl$_3$; 27° C.)
δ (ppm)
7.21–7.40 (15H, m), 6.89 (1H, d, J=8.6 Hz), 5.21 (1H, dd, J=5.1, 6.6 Hz), 4.27 (1H, m), 3.60 (1H, m), 3.43 (1H, dd, J=3.2, 7.1 Hz), 3.36 (1H, dd, J=4.2, 7.1 Hz), 3.34 (1H, m), 3.01 (1H, m), 2.08 (1H, m), 2.05 (3H, s), 1.85 (1H, m), 1.75 (1H, m), 1.68 (1H, m), 1.10–1.50 (62H, m), 0.88 (6H, t, J=7.3 Hz).

(xi) Synthesis of the compound D12

To the solution of the trityl derivative (compound D11, 166.5 mg) in pyridine (3 ml) were added benzoyl chloride (0.18 ml) and 4-dimethylaminopyridine (5.0 mg). After stirring at room temperature for 36 hours, the mixture was diluted with brine, extracted with chloroform and concentrated. Purification on a silica gel column (Wake Gel C-200, 15 g) eluting with hexane-ethyl acetate (95.5) afforded a benzoyl derivative (compound D12) in an amount of 193.9 mg (yield, 95.6%).

Data of the compound D12
$[\alpha]^{23}_D 32 +7.3°$ (CHCl$_3$, c=0.5)
MS: FDMS 1162, 920.
NMR: $^1$H (500 MHz, CDCl$_3$; 27° C.)
δ (ppm)
7.04–8.16 (25H, m), 5.91 (1H, dd, J=2.4, 9.0 Hz), 5.54 (1H, dt, J=2.9, 9.8 Hz), 5.37 (1H, t, J=7.3 Hz), 4.68 (1H, m), 3.34 (1H, dd, J=3.7, 9.8 Hz), 3.26 (1H, dd, J=2.9, 9.8 Hz), 2.02 (3H, s), 1.12–2.02 (66H, m), 0.87 (6H, m).

(xii) Synthesis of the compound D13

To the solution of benzoyl derivative (compound D12, 193.9 mg) in a solution of methylene chloride-methanol (2:1) (3 ml) was added p-toluenesulfonic acid monohydrate (63.4 mg). After being stirred at room temperature for 1.5 hours, the mixture was concentrated. The residue was dissolved in ethyl acetate and washed with aqueous sodium hydrogen carbonate and brine, and then concentrated. Purification on a silica gel column (Wako Gel C-200, 15 g) eluting with hexane-ethyl acetate (8:2) afforded an alcohol (compound D13) in an amount of 113.1 mg (yield, 73.3%).

Data of the compound D13
$[\alpha]^{23}_D = +27.2°$ (CHCl$_3$, c=0.1)
MS: FDMS 921.
NMR: $^1$H (500 MHz, CDCl$_3$; 27° C.)
δ (ppm)
8.06 (2H, d, J=7.3 Hz), 7.96 (2H, d, J=7.3 Hz), 7.64 (1H, t, J=7.3 Hz), 7.54 (1H, t, J=7.6 Hz), 7.50 (2H, t, J=7.9 Hz), 7.39 (2H, t, J=7.9 Hz), 7.06 (1H, d, J=9.2 Hz), 5.48 (1H, dd, J=2.4, 9.1 Hz), 5.38 (1H, dt, J=3.1, 9.8 Hz), 5.19 (1H, t, J=6.1 Hz), 4.37 (1H, m), 3.57–3.68 (2H, m), 2.20 (3H, s), 2.02 (2H, m), 1.92 (2H, m), 1.16–1.50 (62H, m), 0.88 (6H, m).

(xiii) Synthesis of the compound D14

To the solution of the alcohol (compound D13, 113.1 mg) in tetrahydrofuran (2 ml) were added stannous chloride (54.8 mg), silver perchlorate (59.9 mg) and powdered Molecular Sieves 4A (500 mg), and the mixture was stirred at room temperature for 30 minutes. After the mixture was cooled to =10° C., a solution of benzylgalactosyl fluoride (compound A13, 313.4 mg) in tetrahydrofuran (2 ml) was added. The resulting mixture was allowed to warm to room temperature, stirred for 2 hours, and then diluted with acetone, filtered through celite. The filtrate was evaporated under reduced pressure, and the residue was suspended in ethyl acetate, washed with brine and concentrated. Purification on a silica gel column (Wako Gel C-200, 10 g) eluting with hexane-ethyl acetate (19:1) afforded an α-galactoside (compound D14) in an amount of 148.0 mg (yield, 83.5%).

Data of the compound D14

$[\alpha]^{23}_D$=+21.0° ($CHCl_3$, c=0.1)

MS: FDMS 1443.

NMR: $^1H$ (500 MHz, $CDCl_3$; 27° C.)

δ (ppm)

8.03 (2H, d, J=7.9 Hz), 7.90 (2H, d, J=7.9 Hz), 7.73 (1H, d, J=8.3 Hz), 7.59 (1H, t, J=6.4 Hz), 7.50 (1H, t, J=6.4 Hz), 7.45 (2H, t, J=7.6 Hz), 7.15–7.40 (22H, m), 5.78 (1H, dd, J=2.6, 9.8 Hz), 5.40 (1H, m), 5.10 (1H, dd, J=5.2, 7.6 Hz), 4.88 (1H, d, J=11.3 Hz), 4.53–4.76 (7H, m), 4.48 (1H, d, J=11.8 Hz), 4.40 (1H, d, J=11.8 Hz), 4.09 (1H, t, J=7.2 Hz), 3.99 (1H, dd, J=3.3, 10.4 Hz), 3.93 (1H, m), 3.90 (1H, m), 3.82 (1H, dd, J=2.4, 9.8 Hz), 3.59 (1H, dd, J=2.3, 12.1 Hz), 3.53 (1H, dd, J=6.4, 8.9 Hz), 3.54 (1H, dd, J=6.7, 9.2 Hz), 2.44 (1H, bs), 2.02 (3H, s), 1.89 (3H, m), 1.40 (2H, m), 1.10–1.35 (61H, m), 0.88 (6H, m).

(xiv) Synthesis of the compound D15

To the solution of the α-galactoside (compound D14, 147.1 mg) in ethyl acetate (3 ml) was added palladium black (15 mg). After the reaction vessel was purged with hydrogen, the mixture was stirred at room temperature for 4 hours, filtered through celite, and the filtrate was concentrated to give a tetraol (compound D15) in an amount of 106.6 mg (yield, 96.6%).

Data of the Compound D15

$[\alpha]^{23}_D$=+26.0° ($CHCl_3$, c=0.1)

MS: FDMS 1083, 921.

NMR: $^1H$ (500 MHz, $CDCl_3$; 27° C.)

δ (ppm)

7.99 (2H, d, J=7.9 Hz), 7.90 (2H, d, J=7.9 Hz), 7.75 (1H, d, J=8.3 Hz), 7.60 (1H, t, J=6.4 Hz), 7.53 (1H, t, J=6.4 Hz), 7.48 (2H, t, J=7/6 Hz), 7.38 (2H, t, J=7.6 Hz), 5.78 (1H, dd, J=2.4, 9.8 Hz), 5.26 (1H, m), 5.07 (1H, t, J=6.7 Hz), 4.70 (1H, d, J=3.7 Hz), 4.57 (1H, m), 3.98 (1H, bs), 3.90 (1H, m), 3.80–3.90 (3H, m), 3.787 (1H, m), 3.70 (1H, m), 3.65 (1H, bd, J=10.4 Hz), 3.46 (2H, m), 3.13 (1H, bs), 2.78 (1H, m), 2.18 (3H, s), 1.81–1.95 (4H, m), 1.41 (2H, m), 1.16–1.35 (60H, m), 0.88 (6H, m).

(xv) Synthesis of the compound 22

To the solution of the tetraol (compound D15, 105.5 mg) in methanol (5 ml) was added slowly a 1 N methanolic sodium methoxide solution (2 ml), and the mixture was stirred at room temperature for 30 minutes. A cation exchange resin (Dowex 50W, X8, manufactured by The Dow Chemical Company) was added to neutralize the mixture, and the resulting mixture was filtered. The solids removed were washed sufficiently with a chloroform-methanol (1:1) solution. The extract was combined with the filtrate, and concentrated. Purification on a silica gel column (Wako Gel C-200, 5 g) eluting with chloroform-methanol-water (90:10:1) afforded a cerebroside (compound 22) in an amount of 66.7 mg (yield, 82.2%).

Data of the compound 22

The various data of the compound 22 accorded with those of the product obtained from the natural material (Example 1-A).

The compounds (16–21, 23–28, 30–33) were synthesized by using various caboxylic acids or combining a variety of Wittig's salts by applying the method for synthesizing the compound 22 (reaction route D). Synthetic examples of these compounds are herein illustrated.

Compound 16

The aldehyde D1 was reacted with tridecanetriphenylphosphonium bromide in place of the Wittig's salt in the synthesis of the compound 22. Synthesis was further conducted by applying the route D. The amine obtained by reducing an azide group was reacted with tetracosanoic acid in place of (R)-2-acetoxytetracosanoic acid D8, and the synthetic process was followed by applying the route D to obtain the compound 16.

[Data]

$[\alpha]^{24}_D$=+28.2° (pyridine, c=0.27)

MS: FDMS 831.

IR: ($cm^{-1}$, KBr)

3350, 2920, 2850, 1640, 1540, 1465.

mp: 146–147° C.

NMR: $^1H$ (500 MHz, $C_5D_5N$; 27° C)

δ (ppm)

8.45 (1H, d, J=8.5 Hz), 5.55 (1H, d, J=3.7 Hz), 5.24 (1H, m), 4.64 (2H, m), 4.52 (1H, m), 4.48 (1H, m), 4.38 (4H, m), 4.28 (2H, bs), 2.41 (2H, t, J=6.3 Hz), 2.24 (1H, m), 1.88 (2H, m), 1.78 (2H, m), 1.64 (1H, m), 1.10–1.45 (62H, m), 0.85 (6H, t, J=6.7 Hz).

$^{13}C$ (125 MHz, $C_5D_5N$; 27° C.)

δ (ppm)

173.2 (s), 101.5 (d), 76.7 (d), 73.0 (d), 72.5 (d), 71.6 (d), 71.0 (d), 70.3 (d), 68.7 (t), 62.7 (t), 51.5 (d), 36.8 (t), 34.3 (t), 32.1 (t), 30.4 (t), 30.1 (t), 30.0 (t), 29.9 (t), 29.9 (t), 29.8 (t), 29.7 (t), 29.6 (t), 26.5 (t), 26.4 (t), 22.9 (t), 14.3 (q).

Compound 17

The amine obtained by reducing an azide group by applying the route D in the synthesis of the compound 22 was reacted with tetracosanoic acid in place of (R)-2-acetoxytetracosanoic acid D8, and the synthetic process was followed by applying the route D to obtain the compound 17.

[Data]

$[\alpha]^{23}_D$=+42.4° (pyridine, c=0.8)

MS: FDMS 817.

IR: ($cm^{-1}$, KBr)

3400, 2950, 2870, 1645, 1535, 1475, 1080.

mp: 166–168° C.

NMR: $^1H$ (500 MHz, $C_5D_5N$; 27° C.)

δ (ppm)

8.43 (1H, d, J=8.6 Hz), 5.55 (1H, d, J=3.7 Hz), 5.23 (1H, m), 4.64 (1H, dd, J=5.5, 10.4 Hz), 4.62 (1H, dd, J=4.3, 10.4 Hz), 4.52 (1H, m), 4.49 (1H, bt, J=6.1 Hz), 4.33–4.42 (4H, m), 4.30 (2H, m), 2.42 (2H, dd, J=6.7, 7.3 Hz), 2.26 (1H, m), 1.86 (2H, m), 1.78 (2H, m), 1.65 (1H, m), 1.16–1.46 (60H, m), 0.85 (6H, t, J=6.7 Hz).

$^{13}C$ (125 MHz, $C_5D_5N$; 27° C.)

δ (ppm)

173.2 (s), 101.5 (d), 76.7 (d), 73.0 (d), 72.4 (d), 71.5 (d), 70.9 (d), 70.2 (d), 68.6 (t), 62.6 (t), 51.4 (d), 36.7 (t), 34.3 (t), 32.1 (t), 30.3 (t), 30.1 (t), 30.0 (t), 29.9 (t), 29.8 (t), 29.8 (t), 29.7 (t), 29.7 (t), 29.5 (t), 26.4 (t), 26.3 (t), 22.9 (t), 14.2 (q).

Compound 18

The aldehyde D1 was reacted with decanetriphenylphosphonium bromide in place of the Wittig's salt D2 in the synthesis of the compound 22. The subsequent synthetic process was followed by applying the route D. The amine obtained by reducing the azide group was reacted with tetracosanoic acid in place of (R)-2-acetoxytetracosanoic acid D8, and the subsequent steps were followed by applying the route D to obtain the compound 18.

[Data]

$[\alpha]^{24}_D$=+30.0° (pyridine, c=0.2)

MS: FDMS 789.

IR: (cm$^{-1}$, KBr)

3350, 2920, 2840, 1640, 1540, 1465.

mp: 154–155° C.

NMR: $^1$H (500 MHz, C$_5$D$_5$N; 27° C.)

δ (ppm)

8.45 (1H, d, J=8.5 Hz), 5.55 (1H, d, J=3.7 Hz), 5.24 (1H, m), 4.64 (2H, m), 4.53 (1H, m), 4.49 (1H, m), 4.39 (4H, m), 4.30 (2H, bs), 2.42 (2H, t, J=6.7 Hz), 2.25 (1H, m), 1.88 (2H, m), 1.78 (2H, m), 1.64 (1H, m), 1.15–1.45 (56H, m) 0.85 & 0.84 (each 3H, t, J=7.3 Hz).

$^{13}$C (125 MHz, C$_5$D$_5$N; 27° C.)

δ (ppm)

173.3 (s), 101.5 (d), 76.7 (d), 73.0 (d), 72.5 (d), 71.6 (d), 71.0 (d), 70.3 (d), 68.7 (t), 62.7 (t), 51.5 (d), 36.8 (t), 34.3 (t), 32.1 (t), 30.3 (t), 29.6–30.1, 26.5 (t), 26.4 (t), 22.9 (t), 14.3 (q).

Compound 19

The aldehyde D1 was reacted with hexanetriphenylphosphonium bromide in place of the Wittig's salt D2 in the synthesis of the compound 22. The subsequent synthetic process was followed by applying the route D. The amine obtained by reducing the azide group was reacted with tetracosanoic acid in place of (R)-2-acetoxytetracosanoic acid D8, and the subsequent steps were followed by applying the route D to obtain the compound 19.

[Data]

MS: FDMS 732.

NMR: $^1$H (500 MHz, C$_5$D$_5$N; 27° C.)

δ (ppm)

8.45 (1H, d, J=8.6 Hz), 6.97 (1H, bs), 6.62 (1H, bs), 6.52 (1H, m), 6.43 (1H, bs), 6.29 (1H, d, J=3.7 Hz), 6.06 (1H, bs), 5.58 (1H, d, J=3.7 Hz), 5.26 (1H, m), 4.66–4.68 (2H, m), 4.55 (1H, bs), 4.51 (1H, m), 4.38–4.42 (4H, m), 4.30 (1H, bs), 2.44 (2H, t, J=7.3 Hz), 1.80–1.88 (4H, m), 1.19–1.59 (50H, m), 0.88 & 0.81 (each 3H, t, J=6.7 Hz).

Compound 20

Synthesis was conducted by applying the route D in the synthesis of the compound 22. The amine obtained by reducing the azide group was reacted with hexacosanoic acid in place of (R)-2-acetoxytetracosanoic acid D8, and the subsequent steps were followed by applying the route D to obtain the compound 20.

[Data]

$[\alpha]^{25}_D$=+37.3° (pyridine, c=0.97)

MS: FDMS 845.

IR: (cm$^{-1}$, KBr)

3380, 2920, 2840, 1635, 1545, 1465, 1065.

mp: 156–158° C.

NMR: $^1$H (500 MHz, C$_5$D$_5$N; 27° C.)

δ (ppm)

8.46 (1H, d, J=8.6 Hz), 6.42 (1H, m), 6.09 (1H, m), 5.57 (1H, d, J=3.7 Hz), 5.26 (1H, m), 4.66 (2H, m), 4.55 (1H, m), 4.51 (1H, t, J=5.8 Hz), 4.41 (4H, m), 4.32 (2H, m), 2.44 (2H, t, J=7.0 Hz), 2.28 (1H, m), 1.90 (2H, m), 1.81 (2H, m), 1.68 (1H, m), 1.15–1.45 (64H, m), 0.88 (6H, t, J=6.7 Hz).

$^{13}$C (125 MHz, C$_5$D$_5$N; 27° C.)

δ (ppm)

173.2 (s), 101.5 (d), 76.7 (d), 73.0 (d), 72.5 (d), 71.6 (d), 71.0 (d), 70.3 (d), 68.7 (t), 62.7 (t), 51.5 (d), 36.8 (t), 34.4 (t), 32.1 (t), 30.4 (t), 30.1 (t), 30.03 (t), 29.99 (t), 29.93 (t), 29.87 (t), 29.81 (t), 29.76 (t), 29.6 (t), 26.5 (t), 26.4 (t), 22.9 (t), 14.3 (q).

Compound 21

The aldehyde D1 was reacted with decanetriphenylphosphonium bromide in place of the Wittig's salt D1 in the synthesis of the compound 22. The subsequent synthetic process was followed by applying the route D to obtain the compound 21.

[Data]

MS: FDMS 847.

IR: (cm$^{-1}$, KBr)

3400, 2950, 2870, 1645, 1535, 1475, 1080.

NMR: $^1$H (500 MHz, C$_5$D$_5$N; 27° C.)

δ (ppm)

8.50 (1H, d, J=9.2 Hz), 5.59 (1H, d, J=3.7 Hz), 5.27 (1H, m), 4.64 (2H, m), 4.58 (1H, m), 4.53 (1H, m), 4.48 (2H, m), 4.30–4.42 (4H, m), 4.27 (1H, m), 2.29 (1H, m), 2.18 (1H, m), 1.98 (1H, m), 1.87 (2H, m), 1.74 (1H, m), 1.67 (2H, m), 1.15–1.46 (60H, m), 0.84 (6H, t, J=6.7 Hz).

$^{13}$C (125 MHz, C$_5$D$_5$N; 27° C.)

δ (ppm)

174.9 (s), 101.2 (d), 76.5 (d), 73.0 (d), 72.4 (d), 72.3 (d), 71.6 (d), 70.9 (d), 70.1 (d), 68.1 (t), 62.6 (t), 50.4 (d), 35.5 (t), 34.4 (t), 32.1 (t), 30.3 (t), 30.1 (t), 30.0 (t), 29.9 (t), 29.5 (t), 26.4 (t), 25.8 (t), 22.9 (t), 14.2 (q).

Compound 23

The aldehyde D1 was reacted with decanetriphenylphosphonium bromide in place of the Wittig's salt D2 in the synthesis of the compound 22. The subsequent synthetic process was followed by applying the route D to obtain the compound 23.

[Data]

$[\alpha]^{24}_D$=+59.2° (pyridine, c=0.1)

MS: FDMS 805.

IR: (cm$^{-1}$, KBr)

3400, 2950, 2870, 1645, 1535, 1475, 1080.

mp: 193–194° C.

NMR: $^1$H (500 MHz, C$_5$D$_5$N; 27° C.)

δ (ppm)

8.50 (1H, d, J=9.2 Hz), 5.59 (1H, d, J=3.7 Hz), 5.28 (1H, m), 4.64 (2H, m), 4.58 (1H, m), 4.53 (1H, m), 4.48 (2H, m), 4.30 –4.42 (4H, m), 4.27 (1H, m), 2.29 (1H, m), 2.18 (1H, m), 1.98 (1H, m), 1.87 (2H, m), 1.74 (1H, m), 1.66 (2H, m), 1.15–1.46 (54H, m), 0.84 (6H, t, J=6.7 Hz).

$^{13}$C (125 MHz, C$_5$D$_5$N; 27° C.)

δ (ppm)

174.9 (s), 101.2 (d), 76.5 (d), 73.0 (d), 72.4 (d), 72.3 (d), 71.6 (d), 70.9 (d), 70.1 (d), 68.1 (t), 62.6 (t), 50.4 (d), 35.5 (t), 34.4 (t), 32.1 (t), 30.3 (t), 30.1 (t), 30.0 (t), 29.9 (t), 29.5 (t), 26.4 (t), 25.8 (t), 22.9 (t), 14.2 (q).

Compound 24

The aldehyde D1was reacted with hexanetriphenylphosphonium bromide in place of the Wittig's salt D2 in the synthesis of the compound 22. The subsequent synthetic process was followed by applying the route D to obtain the compound 24.

[Data]
[α]²³_D=+67.1° (pyridine, c=1.32)
MS: FDMS 749.
IR: (cm⁻¹, KBr)
3300, 2870, 2800, 1630, 1605, 1515, 1455, 1060.
mp: 145–147° C.
NMR: ¹H (500 MHz, C₅D₅N; 27° C.)
δ (ppm)
8.50 (1H, d, J=9.2 Hz), 6.70 (2H, bd, J=6.1 Hz), 6.53 (1H, bs), 6.31 (1H, bs), 6.08 (1H, bs), 5.61 (1H, d, J=3.7 Hz), 5.29 (1H, m), 4.64–4.67 (2H, m), 4.59 (1H, m), 4.54 (1H, m), 4.47–4.51 (2H, m), 4.32–4.43 (4H, m), 4.26 (1H, m), 1.64–2.27 (4H, m), 1.20–1.40 (50H, m), 0.87 & 0.82 (each 3H, t, J=6.7 Hz).
¹³C (125 MHz, C₅D₅N; 27° C.)
δ (ppm)
175.0 (s), 101.2 (d), 76.5 (d), 73.0 (d), 72.4 (d), 72.3 (d), 71.6 (d), 70.9 (d), 70.1 (d), 68.1 (t), 62.6 (t), 50.4 (d), 35.5 (t), 34.4 (t), 32.0 (t), 30.2 (t), 29.9 (t), 29.8 (t), 29.7 (t), 29.5 (t), 26.3 (t), 25.8 (t), 22.9 (t), 22.8 (t), 14.21 (q). 14.18 (q).

Compound 25

The aldehyde D1 was reacted with tridecanetriphenylphosphonium bromide in place of the Wittig's salt D2 in the synthesis of the compound 22. The subsequent synthetic process was followed by applying the route D, and the amine obtained by reducing the azide group was reacted with (R)-2-acetoxyhexacosanoic acid in place of (R)-2-acetoxytetracosanoic acid D8 with the subsequent synthetic process by applying the route D to give the compound 25.
[Data]
[α]²³_D=+45.2° (pyridine, c=1.0)
MS: FDMS 875.
IR: (cm⁻¹, KBr)
3400, 2950, 2870, 1645, 1535, 1475, 1080.
mp: 198–199° C.
NMR: ¹H (500 MHz, C₅D₅N; 27° C.)
δ (ppm)
8.49 (1H, d, J=9.2 Hz), 7.53 (1H, bs), 7.02 (1H, bs), 6.70 (1H, d, J=6.1 Hz), 6.65 (1H, bs), 6.53 (1H, bs), 6.30 (1H, bs), 6.08 (1H, d, J=5.5 Hz), 5.57 (1H, d, J=3.7 Hz), 5.26 (1H, m), 4.62 (2H, dd, J=4.9, 10.4 Hz), 4.58 (1H, m), 4.51 (1H, bs), 4.46 (2H, m), 4.28–4.41 (4H, m), 4.26 (1H, m), 2.27 (1H, m), 2.17 (1H, m), 1.98 (1H, m), 1.87 (2H, m), 1.74 (1H, m), 1.66 (2H, m), 1.16–1.46 (64H, m), 0.85 (6H, t, J=6.1 Hz).
¹³C (125 MHz, C₅D₅N; 27° C.)
δ (ppm)
175.0 (s), 101.2 (d), 76.5 (d), 73.0 (d), 72.4 (d), 72.3 (d), 71.6 (d), 70.9 (d), 70.1 (d), 68.2 (t), 62.6 (t), 50.5 (d), 35.5 (t), 34.4 (t), 32.1 (t), 30.3 (t), 30.1 (t), 29.9 (t), 29.9 (t), 29.6 (t), 26.4 (t), 25.8 (t), 22.9 (t), 14.2 (q).

Compound 26

The aldehyde D1 was reacted with tetradecanetriphenylphosphonium bromide in place of the Wittig's salt D2 in the synthesis of the compound 22. The subsequent synthetic process was followed by applying the route D, and the amine obtained by reducing the azide group was reacted with (R)-2-acetoxyhexacosanoic acid in place of (R)-2-acetoxytetracosanoic acid D8 with the subsequent synthetic process by applying the route D to give the compound 26.
[Data]
[α]²³_D=+46.5° (pyridine, c=0.7)
MS: FDMS 889.
IR: (cm⁻¹, KBr)
3400, 2950, 2870, 1645, 1535, 1475, 1080.
mp: 205–206° C.
NMR: ¹H (500 MHz, C₅D₅N; 27° C.)
δ (ppm)
8.50 (1H, d, J=9.2 Hz), 7.56 (1H, bs), 7.04 (1H, bs), 6.71 (1H, d, J=6.7 Hz), 6.66 (1H, bs), 6.54 (1H, bs), 6.32 (1H, bs), 6.10 (1H, d, J=5.5 Hz), 5.58 (1H, d, J=3.7 Hz), 5.27 (1H, m), 4.63 (2H, m), 4.58 (1H, m), 4.52 (1H, bs), 4.47 (2H, m), 4.28–4.41 (4H, m), 4.27 (1H, m), 2.27 (1H, m), 2.18 (1H, m), 1.99 (1H, m), 1.88 (2H, m), 1.74 (1H, m), 1.66 (2H, m), 1.16–1.46 (66H, m), 0.85 (6H, t, J=6.7 Hz).
¹³C (125 MHz, c₅D₅N; 27° C.)
δ (ppm)
175.0 (s), 101.2 (d), 76.5 (d), 73.0 (d), 72.4 (d), 72.3 (d), 71.6 (d), 70.9 (d), 70.1 (d), 68.1 (t), 62.6 (t), 50.4 (d), 35.5 (t), 34.4 (t), 32.1 (t), 30.3 (t), 30.1 (t), 29.9 (t), 29.9 (t), 29.5 (t), 26.4 (t), 25.8 (t), 22.9 (t), 14.2 (q).

Compound 27

The aldehyde D1 was reacted with heptadecanetriphenylphosphonium bromide in place of the Wittig's salt D2 in the synthesis of the compound 22. the subsequent synthetic process was followed by applying the route D, and the amine obtained by reducing the azide group was reacted with (R)-2-acetoxyhexacosanoic acid in place of (R)-2-acetoxytetracosanoic acid D8 with the subsequent synthetic process by applying the route D to give the compound 27.
[Data]
[α]²³_D=+46.0° (pyridine, c=0.8)
MS: FDMS 903.
IR: (cm⁻¹, KBr)
3400, 2950, 2870, 1645, 1535, 1475, 1080.
mp: 200–201° C.
NMR: ¹H (500 MHz, C₅D₅N; 27° C.)
δ (ppm)
8.49 (1H, d, J=9.2 Hz), 7.54 (1H, bs), 7.02 (1H, bs), 6.69 (1H, d, J=6.7 Hz), 6.66 (1H, bs), 6.53 (1H, bs), 6.30 (1H, bs), 6.08 (1H, d, J=4.9 Hz), 5.57 (1H, d, J=3.7 Hz), 5.25 (1H, m), 4.62 (2H, dd, J=4.9, 10.4 Hz), 4.57 (1H, m), 4.51 (1H, bs), 4.46 (2H, m), 4.28–4.40 (4H, m), 4.26 (1H, m), 2.26 (1H, m), 2.17 (1H, m), 1.98 (1H, m), 1.87 (2H, m), 1.73 (1H, m), 1.65 (2H, m), 1.16–1.46 (68H, m), 0.86 (6H, t, J=6.7 Hz).
¹³C (125 MHz, C₅D₅N; 27° C.)
δ (ppm)
175.0 (s), 101.2 (d), 76.4 (d), 73.0 (d), 72.4 (d), 72.3 (d), 71.5 (d), 70.9 (d), 70.1 (d), 68.1 (t), 62.6 (t), 50.5 (d), 35.5 (t), 34.3 (t), 32.1 (t), 30.3 (t), 30.1 (t), 29.9 (t), 29.6 (t), 26.4 (t), 25.8 (t), 22.9 (t), 14.2 (q).

As the alternative methods for synthesizing the compounds 25, 26 and 27, Cerebrin E was employed. Cerebrin E which is a tetraol and commercially available from Alfred Baker Chemicals or K&K Laboratories, Inc. was used in place of the triol D10 in the synthesis of the compound 22. Synthesis was further conducted by applying the route D to obtain the compounds 25, 26 and 27. These compounds were separated by high performance liquid chromatography (D-ODS-5, manufactured by K. K. YMC, eluent: 100% methanol, 45° C.).

Compound 28

In the synthesis of the compound 22, the route D was followed. The amine obtained by reducing the azide group was reacted with (S)-2-acetoxytetracosanoic acid in place of (R)-2-acetoxytetracosanoic acid D8 with the subsequent synthetic process by applying the route D to give the compound 28.
[Data]

[α]$^{23}_D$=+36.8° (pyridine, c=2.0)
MS: FDMS 833.
IR: (cm$^{-1}$, KBr)
3400, 2950, 2870, 1645, 1535, 1475, 1080.
mp: 174–176° C.
NMR: $^1$H (500 MHz, C$_5$D$_5$N; 27° C.)
δ (ppm)
8.55 (1H, d, J=8.5 Hz), 5.61 (1H, d, J=4.3 Hz), 5.26 (1H, m), 4.68 (1H, dd, J=5.5, 10.4 Hz), 4.63 (1H, dd, J=3.7, 9.8 Hz), 4.56 (2H, bs), 4.49 (1H, t, J=5.5 Hz), 4.46 (1H, dd, J=3.7, 9.8 Hz), 4.38 (2H, m), 4.34 (1H, dd, J=4.3, 11.0 Hz), 4.31 (1H, bd, J=8.6 Hz), 4.20 (1H, dd, J=3.7, 7.9 Hz), 2.26 (1H, m), 2.19 (1H, m), 1.99 (1H, m), 1.84 (2H, m), 1.74 (1H, m), 1.58–1.70 (1H, m), 1.16–1.46 (58H, m), 0.85 (6H, t, J=6.7 Hz).
$^{13}$C (125 MHz, C$_5$D$_5$N; 27° C.)
δ (ppm)
175.0 (s), 101.2 (d), 76.7 (d), 73.0 (d), 72.5 (d), 72.4 (d), 71.6 (d), 70.9 (d), 70.1 (d), 68.0 (t), 62.6 (t), 50.5 (d), 35.6 (t), 34.6 (t), 32.1 (t), 30.3 (t), 30.1 (t), 29.9 (t), 29.9 (t), 29.6 (t), 26.3 (t), 25.8 (t), 22.9 (t), 14.2 (q).

Compound 30

The aldehyde D1 was reacted with 11-methyl-9-dodecenetriphenylphosphonium bromide in place of the Wittig's salt D2 in the synthesis of the compound 22. The subsequent synthetic process was followed by applying the route D, and the amine obtained by reducing the azide group was reacted with (S)-2-acetoxyhexacosanoic acid in place of (R)-2-acetoxytetracosanoic acid D8 with the subsequent synthetic process by applying the route D to give the compound 30.

[Data]
[α]$^{25}_D$=+46.2° (pyridine, c=1.0)
MS: FDMS 847.
IR: (cm$^{-1}$, KBr)
3400, 3250, 2870, 2810, 1640, 1525, 1455, 1355, 1320, 1275, 1145, 1060.
mp: 169.0–171.0° C.
NMR: $^1$H (500 MHz, C$_5$D$_5$N; 27° C.)
δ (ppm)
8.57 (1H, d, J=9.2 Hz), 6.64 (2H, m), 6.45 (1H, m), 6.30 (1H, m), 6.11 (2H, m), 5.65 (1H, d, J=3.7 Hz), 5.29 (2H, m), 4.65–4.75 (2H, m), 4.59 (2H, m), 4.51 (2H, m), 4.30–4.45 (4H, m), 4.22 (1H, m), 2.30 (1H, m), 2.21 (1H, m), 2.02 (1H, m), 1.6–2.0 (5H, m), 1.49 (1H, m) 1.15–1.35 (56H, m), 0.89 (3H, t, J=6.1 Hz), 0.87 (6H, d, J=6.1 Hz).
$^{13}$C (125 MHz, C$_5$D$_5$N; 27° C.)
δ (ppm)
175.0 (s), 101.3 (d), 76.7 (d), 73.0 (d), 72.4 (d), 72.3 (d), 71.6 (d), 70.9 (d), 70.1 (d), 68.0 (t), 62.6 (t), 50.6 (d), 39.2 (t), 35.6 (t), 34.6 (t), 32.1 (t), 30.3 (t), 30.2 (t), 30.1 (t), 30.0 (t), 29.9 (t), 29.6 (t), 28.1 (d), 27.7 (t), 26.3 (t), 25.8 (t), 22.9 (t), 22.7 (q), 14.2 (q).

Compound 31

The aldehyde D1 was reacted with 11-methyl-9-dodecenetriphenylphosphonium bromide in place of the Wittig's salt D2 in the synthesis of the compound 22. The subsequent synthetic process was followed by applying the route D, and the amine obtained by reducing the azide group was reacted with tetracosanoic acid in place of (R)-2-acetoxytetracosanoic acid D8 with the subsequent synthetic process by applying the route D to give the compound 31.

[Data]
[α]$^{25}_D$=+43.6° (pyridine, c=0.44)
MS: FDMS 831.
IR: (cm$^{-1}$, KBr)
3300, 2880, 2810, 1630, 1535, 1455, 1055.
mp: 197.0–198.5° C.
NMR: $^1$H (500 MHz, C$_5$D$_5$N; 27° C.)
δ (ppm)
8.44 (1H, d, J=8.6 Hz), 5.57 (1H, d, J=3.7 Hz), 5.25 (1H, m), 4.63–4.70 (2H, m), 4.54 (1H, d, J=3.1 Hz), 4.50 (1H, t, J=6.1 Hz), 4.35–4.45 (4H, m), 4.31 (2H, m), 2.44 (2H, t, J=7.3 Hz), 2.28 (1H, m), 1.90 (2H, m), 1.81 (2H, m), 1.68 (1H, m), 1.49 (1H, m), 1.2–1.45 (56H, m), 1.15 (2H, m), 0.88 (3H, t, J=6.7 Hz), 0.87 (6H, d, J=6.7 Hz).
$^{13}$C (125 MHz, C$_5$D$_5$N; 27° C.)
δ (ppm)
173.2 (s), 101.5 (d), 76.7 (d), 73.0 (d), 72.5 (d), 71.6 (d), 71.0 (d), 70.3 (d), 68.7 (t), 62.7 (t), 51.4 (d), 39.3 (t), 36.8 (t), 34.4 (t), 32.1 (t), 30.4 (t), 30.23 (t), 30.15 (t), 30.03 (t), 30.00 (t), 29.91 (t), 29.87 (t), 29.81 (t), 29.75 (t), 29.6 (d), 28.2 (d), 27.7 (t), 26.5 (t), 26.4 (t), 22.9 (t), 22.8 (q), 14.3 (q).

Compound 36

In the synthesis of Compound 22, the aldehyde D1 was treated with, instead of the Wittig salt D2, tridecanetriphenylphosphonium bromide, and the amine synthesized in accordance with the route D, with an azide group reduced was treated with, instead of the (R)-2-acetoxytetracosanic acid D8, hexacosanic acid. After this, the synthesis was continued in accordance with the route D to give Compound 36.

[Data]
[α]$^{23}_D$=+43.9° (pyridine, c=0.81)
MS: negative FAB-MS 857 [(M-H)$^-$]
IR: (cm$^{-1}$, KBr)
3300, 2930, 2850, 1640, 1540, 1470, 1070.
mp: 130–135° C.
NMR: $^1$H (500 MHz, C$_5$D$_5$N; 27° C.)
δ (ppm)
8.47 (1H, d, J=8.5 Hz), 6.97 (1H, d, J=1.8 Hz), 6.63 (1H, bs), 6.54 (1H, m), 6.44 (1H, d, J=5.5 Hz), 6.32 (1H, bs), 6.09 (1H, d, J=5.0 Hz), 5.58 (1H, d, J=3.7 Hz), 5.27 (1H, m), 4.65–4.70 (2H, m), 4.56 (1H, bs), 4.52 (1H, t, J=5.5 Hz), 4.37–4.47 (4H, m), 4.31–4.35 (2H, m), 2.45 (2H, t, J=7.3 Hz), 1.78–1.97 (4H, m), 1.26–1.69 (68H, m), 0.88 (6H, t, J=6.7 Hz).
$^{13}$C (125 MHz, C$_5$D$_5$N; 27° C.)
δ (ppm)
173.2 (s), 101.5 (d), 76.7 (d), 73.0 (d), 72.5 (d), 71.6 (d), 71.0 (d), 70.3 (d), 68.7 (t), 62.7 (t), 51.4 (d), 36.8 (t), 34.4 (t), 32.1 (t), 30.4 (t), 30.2 (t), 30.0 (t), 30.0 (t), 29.9 (t), 29.9 (t), 29.8 (t), 29.6 (t), 26.5 (t), 26.4 (t), 22.9 (t), 14.3 (q).

Compound 37

In the synthesis of Compound 22, the amine synthesized in accordance with the route D, with an azide group remained was treated with, instead of the (R)-2-acetoxytetracosanic acid D8, octacosanic acid. After this, the synthesis was continued in accordance with the route D to give Compound 37.

[Data]
[α]$^{24}_D$=+46.8° (pyridine, c=0.47)
MS: negative FAB-MS 871 [(M-H)$^-$]
IR: (cm$^{-1}$, KBr)
3350, 2930, 2850, 1640, 1540, 1470, 1080.
mp: 142–145° C.
NMR: $^1$H (500 MHz, C$_5$D$_5$N; 27° C.)
δ (ppm)

8.46 (1H, d, J=7.9 Hz), 6.92–6.98 (1H, m), 6.59–6.63 (1H, m), 6.53 (1H, bs), 6.44 (1H, d, J=5.5 Hz), 6.33 (1H, bs), 6.07 (1H, d, J=5.5 Hz), 5.58 (1H, d, J=3.7 Hz), 5.25–5.30 (1H, m), 4.62–4.70 (2H, m), 4.56 (1H, bs), 4.52 (1H, t, J=6.1 Hz), 4.36–4.47 (3H, m), 4.29–4.35 (2H, m), 2.44 (2H, t, J=6.7 Hz), 1.78–1.97 (4H, m), 1.25–1.72 (70H, m), 0.88 (6H, t, J=6.7 Hz).

$^{13}$C (125 MHz, C$_5$D$_5$N; 27° C.)

δ (ppm)

173.2 (s), 101.5 (d), 76.7 (d), 73.0 (d), 72.5 (d), 71.6 (d), 71.0 (d), 70.3 (d), 68.6 (t), 62.6 (t), 51.4 (d), 36.8 (t), 34.3 (t), 32.1 (t), 30.3 (t), 30.1 (t), 30.0 (t), 30.0 (t), 29.9 (t), 29.9 (t), 29.8 (t), 29.7 (t), 26.6 (t), 26.5 (t), 26.4 (t), 22.9 (t), 14.3 (q).

(5) Synthetic Route E

Those compounds which are represented by the formulae (VIII), (X), (X'), (XII), (XIV), (XIV') or (XVIII) can also be synthesized in accordance with the following reaction route. Although this reaction route is specifically described in reference to Compound 36, the compounds according to the present invention (Compound 16 or 37 except Compound 29 and 36) can also be synthesized in accordance with this route.

(Synthesis of Compound 36 (FIGS. 11-*a* to 11-*c*))

(i) Synthesis of the Compound E2

300 ml of acetone dehydrated by calcium chloride was added to 20 g (0.133 mol) of D-lyxose (Compound E1) to obtain a suspension, and 0.05 ml of concentrated sulfuric acid was added to the suspension. The mixture was stirred at room temperature for 18 hours, and neutralized by the addition of 10.0 g of molecular sieves 4A. The resulting mixture was filtered, and the residue was thoroughly washed with acetone. The was liquids were combined, and concentrated under reduced pressure. The compound thus obtained was used in the subsequent reaction without subjecting it to purification.

(ii) Synthesis of the Compound E3

The whole quantity of Compound E2 obtained by the above reaction was dissolved in 168 ml of methylene chloride. To this solution were added 10.0 ml of pyridine and 39.0 of trityl chloride, and the mixture was stirred at 32° C. for 4 hours. 7.8 ml of ethanol was then added to the mixture. The resulting mixture was stirred, washed with, in the order named, a saturated aqueous solution of ammonium chloride, a saturated aqueous solution of sodium hydrogencarbonate and a saturated saline solution, and then concentrated under reduced pressure. 20 ml of ethyl acetate was added to the syrup thus obtained to obtain a solution to which was slowly added 40 ml of hexane. When the mixture became slightly cloudy, crystal nuclei were added, and the mixture was allowed to stand at 0° C. The crystals obtained were collected by filtration, and washed with an 8:1 mixture of hexane and ethyl acetate, thereby obtaining 44.4 g of primary crystals, and, from the mother liquor, 5.6 g of seconcary crystals. The yield was 86.8%.

[Data]

mp: 174–176° C.

FD-MS: 432 (C$_{27}$H$_{28}$O$_5$: Mw=432.19)

IR: (cm$^{-1}$, KBr)

3530, 3400, 3050, 2950, 2880, 1600, 1490, 1450, 1375, 1215, 1070.

NMR: $^1$(500 MHz, CDCl$_3$)

δ (ppm)

7.48 (6H, d, J=7.3 Hz), 7.29 (6H, t, J=7.3 Hz), 7.22 (3H, t, J=7.3 Hz), 5.38 (1H, d, J=2.4 Hz), 4.75 (1H, dd, J=5.5 Hz, 3.7 Hz), 4.59 (1H, d, J=6.1 Hz), 4.32–4.34 (1H, m), 3.43 (1H, dd, J=4.9 Hz, 9.8 Hz), 3.39 (1H, dd, 6.7 Hz, 9.8 Hz), 2.33 (1H, d, J=2.4 Hz), 1.29 (3H, s), 1.28 (3H, s).

(III) Synthesis of the Compound E4

96.0 g of triphenylphosphine was added to 96.4 g of 1-bromotridecane. The mixture was stirred at 140° C. for 4.5 hours, and then allowed to slowly dissipate heat. 500 ml of tetrahydrofuran was added to this mixture to obtain a solution which was then cooled to 0° C. 146.4 ml of a 2.5 N solution of n-butyllithium was added dropwise to the solution, and the mixture was stirred for 15 minutes. To this mixture was added 79 g/150 ml of a tetrahydrofuran solution of Compound E3, and the resulting mixture was stirred for 18 hours while it was gradually cooled to room temperature. After the mixture was concentrated under reduced pressure, 1000 ml of a 10/7/3 mixture of hexane/methanol/water was added to it, and 40 ml of a saturated aqueous solution of ammonium chloride was then added to the mixture. The resulting mixture was separated into layers, and the methanol/water layer was subjected to re-extraction with 500 ml of hexane. All of the hexane layers obtained were dried over anhydrous magnesium sulfate, concentrated under reduced pressure, and then thoroughly dried under reduced pressure by using a vacuum pump to give a crude syrup of Compound E4. This compound was used in the subsequent reaction without subjecting it to purification any more.

(iv) Synthesis of the Compound E5

To the whole quantity of Compound E4 obtained by the above reaction were added 600 ml of methylene chloride and 200 ml of pyridine. To this mixture was then added 16.95 ml of methanesulfonyl chloride, and the mixture was stirred at 31° C. for 24 hours. 13 ml of ethanol was added to the mixture. The resulting mixture was stirred at room temperature for one hour, and then concentrated under reduced pressure. To this was added 1000 ml of a 10/7/3 mixture of hexane/methanol/water, and this mixture was separated into layers. The methanol/water layer was subjected to re-extraction three times with 200 ml of hexane. All of the hexane layers obtained were dried over anhydrous magnesium sulfate, concentrated under reduced pressure, and then thoroughly dried under reduced pressure by using a vacuum pump to give a crude syrup of Compound E5. This compound was used in the subsequent reaction without subjecting it to purification any more.

(v) Synthesis of the Compound E6

To the whole quantity of Compound E5 obtained by the above process were added 900 ml of methylene chloride and 600 ml of methanol to obtain a solution. 124 ml of concentrated hydrochloric acid was then added to the solution. The mixture was stirred at room temperature for 5 hours, neutralized by the addition of sodium hydrogencarbonate, and then filtered. The residue was washed with ethyl acetate. The wash liquid and the filtrate were combined, and concentrated under reduced pressure. Ethyl acetate was added to the residue, and the resulting mixture was washed with a saturated saline solution. The aqueous layer was subjected to re-extraction three times with ethyl acetate. All of the ethyl acetate layers obtained were dried over anhydrous magnesium sulfate, and then concentrated under reduced pressure. Crystallization was conducted from hexane, thereby obtaining 41.0 g of primary crystals and 9.40 g of secondary crystals. The total yield in the three stages was 70.0%.

[Data]

mp: 66–67° C.

FD-MS: 377 (M-H$_2$O)$^+$, (C$_{19}$H$_{38}$O$_6$S; Mw=394.57)

IR: (cm$^{-1}$, KBr)

3500, 3350, 2920, 2850, 1465, 1440, 1355, 1330, 1160, 1030, 930.

NMR: $^1$H (500 MHz, CDCl$_3$+D$_2$O–1 drop); E/Z mixture (3:7)

δ (ppm)

5.86 (0.3H, dt, J=7.3 Hz, 14.7 Hz), 5.77 (0.7H, dt, J=7.3 Hz, 10.4 Hz), 5.55 (0.3H, br. dd, J=7.3 Hz, 14.7 Hz), 5.49 (0.7H, br. t, J=9.8 Hz), 4.91–4.97 (1H, m), 4.51 (0.7H, br. t, J=9.8 Hz), 4.11 (0.3H, br. t, J=7.3 Hz), 3.94–4.03 (2H, m), 3.67–3.73 [1H(3.70 , dd, J=3.1 Hz, 6.7 Hz), (3.69, dd, J=3.1 Hz, 7.3 Hz)], 3.20 (2.1H, s), 3.19 (0.9H, s), 2.05–2.22 (2H, m), 1.22–1.43 (20H, m), 0.88 (3H, t. J=6.7 Hz).

(vi) Synthesis of the Compound E7

24.4 g of Compound E6 was dissolved in 244 ml of tetrahydrofuran. To this solution was added 2.44 g of 5% palladium-barium sulfate. The inside of a reactor was replaced by hydrogen gas, and the mixture was stirred at room temperature for 20 hours under hydrogen atmosphere. The mixture was diluted with 200 ml of a 1:1 mixture of chloroform and methanol which was kept at 60° C., and the diluted solution was filtered through Celite. The residue was washed with a 1:1 mixture of chloroform and methanol. The filtrate and the wash liquid were combined, and concentrated under reduced pressure. Crystallization was then conducted from ethyl acetate, and the crystals obtained were thoroughly washed with hexane. Thus, 21.5 g of primary crystals, and 0.64 g of secondary crystals were obtained. The yield was 91.3%.

[Data]

mp: 124–126° C.

FD-MS: 397 ($C_{19}H_{40}O_6S$; Mw=396.59)

$[\alpha]^{23}_D$=+7.52° (c=1.50, $C_5H_5N$)

IR: ($cm^{-1}$, KBr)

3500, 3380, 3220, 2920, 2850, 1470, 1430, 1360, 1330, 1165, 1095, 930.

NMR: $^1H$ (500 MHz, $CDCl_3$–$CD_3OD$=1:1)

δ (ppm)

4.93–4.96 (1H, m), 3.91 (1H, dd, J=6.7 Hz, 12.2 Hz), 3.85 (1H, dd, J=4.9 Hz, 12.2 Hz), 3.54–3.60 (1H, m), 3.50 (1H, dd, J=1.8 Hz, 8.5 Hz), 3.19 (3H, s), 1.75–1.83 (1H, m) 1.53–1.62 (1H, m), 1.21–1.45 (24H, m), 0.89 (3H, t, J=6.7 Hz).

(vii) Synthesis of the Compound E8

8.94 g (22.5 mmol) of Compound E7 was dissolved in 72 ml of dried DMF, and 2.93 g of $NaN_3$ was added to this solution. The mixture was heated to 95° C. in an oil bath, and stirred for 4 hours while heating. After the consumption of the starting compound was confirmed by TLC (hexane:acetone=3:2), the reaction mixture was concentrated under reduced pressure. Ethyl acetate was added to the residue, and the resulting mixture was washed with water. The aqueous phase was subjected to re-extraction with an equal amount of ethyl acetate. The ethyl acetate layers were combined, washed with a saturated saline solution, dried over anhydrous magnesium sulfate, concentrated under reduced pressure, and then thoroughly dried by using a vacuum pump. The compound thus obtained was used in the subsequent reaction without subjecting it to purification.

(viii) Synthesis of the Compound E9

45 ml of dichloromethane was added to the whole quantity of the powder obtained by the above reaction, and 7.53 g of TrCl was further added to this mixture. Subsequently, 14 ml of pyridine was added, and the mixture was stirred at room temperature for 16 hours. After the consumption of the starting compound was confirmed by TLC (hexane:ethyl acetate=2:1), 1.8 ml of ethanol was added to the mixture to terminate the reaction, and the resulting mixture was stirred for 30 minutes as it was. The reaction mixture was washed with, in the order named, a saturated aqueous solution of sodium hydrogencarbonate, a saturated aqueous solution of ammonium chloride and a saturated saline solution, dried over anhydrous magnesium sulfate, and concentrated under reduced pressure. The syrup thus obtained was purified by using a silica gel column (hexane:ethyl acetate=10:1). The amount of Compound E9 obtained was 6.93 g (yield 52%).

[Data]

FD-MS: 585 ($C_{37}H_{51}N_3O_3$; Mw=585.82)

$[\alpha]^{23}_D$=+11.86° (c=0.86, $CHCl_3$)

IR: ($cm^{-1}$, film)

3425, 2924, 2854, 2098, 1491, 1466, 1448, 1267, 1223, 1074, 1034.

NMR: $^1H$ (500 MHz, $CDCl_3$+$D_2O$–1 drop)

δ (ppm)

7.24–7.61 (15H, m), 3.62–3.66 (2H, m), 3.51–3.57 (2H, m), 3.42 (1H, dd, J=6.0 Hz, 10.4 Hz), 1.23–1.56 (26H, m), 0.88 (3H, t, J=6.7 Hz).

(ix) Synthesis of the Compound E10

21.73 g of syrup Compound E9 was dissolved in 200 ml of dimethylformamide, and 3.57 g of 60% sodium hydride was added to this solution little by little. The mixture was stirred at room temperature for 40 minutes, and then cooled with ice. 9.71 ml (1.05 equivalent) of benzyl bromide was added dropwise, and the mixture was stirred for 2.5 hours while it was gradually warmed to room temperature. After the consumption of the starting compound was confirmed by TLC (hexane:ethyl acetate=10:1), the reaction was terminated by adding chunks of ice to the reaction mixture. 50 ml of water was added to the reaction mixture, and the resulting mixture was subjected to extraction three times with ethyl acetate. The ethyl acetate layers were washed three times with a saturated saline solution, dried over anhydrous magnesium sulfate, and then concentrated under reduced pressure. The syrup thus obtained was purified by a silica gel column (hexane:ethyl acetate=100:1). The amount of Compound E10 obtained was 23.97 g (yield 84.4%).

[Data]

FD-MS: 738 $(M-N_2)^{30}$ , ($C_{51}H_{63}N_3O_3$; Mw=766.07)

$[\alpha]^{23}_D$=+9.75° (c=0.97 $CHCl_3$)

IR: ($cm^{31\ 1}$, film)

3062, 3031, 2925, 2854, 2096, 1492, 1465, 1450.

NMR: $^1H$ (500 MHz, $CDCl_3$)

δ (ppm)

7.07–7.48 (25H, m), 4.57 (1H, d, J=11.0 Hz), 4.44 (1H, d, J=11.0 Hz), 4.41 (2H, s), 3.37–3.79 (1H, m), 3.46–3.56 (2H, m), 3.37 (1H, dd, J=8.6 Hz, 10.4 Hz), 1.20–1.64 (26H, m), 0.88 (3H, t, J=6.7 Hz).

(x) Synthesis of the Compound E11

200 ml of 1-propanol and 25 ml of methanol were added to 25.35 g (33.14 mmol) of Compound E10, a starting compound, to obtain a solution, and 16.72 g of ammonium formate and 1.0 g of 10% palladium-carbon were added to this solution. The mixture was stirred at room temperature for 16 hours. After the consumption of the starting compound and the formation of the desired compound were confirmed by TLC (hexane:acetone=3:1), 50 ml of ethyl acetate was added to the reaction mixture, and the resulting mixture was filtered through Celite. The residue was washed with ethyl acetate with the wash liquid dropped in the filtrate. The wash liquid and the filtrate were concentrated under reduced pressure. Ethyl acetate was added to the residue, and the resulting mixture was washed twice with a saturated aqueous solution of $NaHCO_3$. The aqueous layer was subjected to re-extraction with ethyl acetate. The ethyl acetate layers were combined, washed with a saturated saline solution, dried over anhydrous magnesium sulfate, concentrated under reduced pressure, subjected to azeotropic distillation with toluene, and then thoroughly dried by using a vacuum pump. The compound thus obtained was used in the subsequent reaction without subjecting it to purification.

(xi) Synthesis of the Compound E12

To the whole quantity of syrup Compound E11 obtained by the above reaction was added 250 ml of methylene chloride to obtain a solution, and 12.49 g of cerotic acid and 7.13 g of WSC hydrochloride were added to this solution. The mixture was warmed in an oil bath, and refluxed at approximately 50° C. for 2 hours. Since the presence of the starting compound was confirmed by TLC (hexane:acetone= 3:1), 620 mg of cerotic acid and 360 mg of WSC hydrochloride were further added, and the mixture was refluxed by heating for a further one hour. The reaction mixture was then cooled to room temperature, washed with, in the order named, a 0.5 N aqueous solution of hydrochloric acid, a saturated saline solution, a saturated aqueous solution of sodium hydrogencarbonate and a saturated saline solution, dried over anhydrous magnesium sulfate, concentrated under the reduced pressure, and then thoroughly dried by using a vacuum pump. The compound thus obtained was used in the subsequent reaction without subjecting it to purification.

(xii) Synthesis of the Compound E13

To the whole quantity of syrup Compound E12 obtained by the above reaction were added 120 ml of methylene chloride and 30 ml of methanol to obtain a solution, and 3.0 ml of a 10% hydrochloric acid-methanol solution was then added dropwise to this solution. The mixture was stirred at room temperature for approximately 2 hours. After the completion of the reaction was confirmed by TLC (hexane:acetone=3:1), the reaction mixture was neutralized by the addition of sodium hydrogencarbonate, filtered through Celite, washed twice with a saturated saline solution, dried over anhydrous magnesium sulfate, and then concentrated under reduced pressure. The resultant was subjected to azeotropic distillation with toluene. Acetone was added to this, and the mixture was heated to obtain a solution. The solution was preserved at 0° C. to give white precipitates. The amount of the precipitates was 22.2 g. The total yield in the three stages was 76.6%.

[Data]
mp: 75–76.5° C.
FD-MS: 876 ($C_{58}H_{101}NO_4$; Mw=876.43)
$[\alpha]^{23}_D$=–29.7° (c=0.675, $CHCl_3$)
IR: ($cm^{-1}$, KBr)
3334, 2918, 2850, 1637, 1618, 1548, 1469, 1103, 1052.
NMR: $^1H$ (500 MHz, $CDCl_3$)
δ (ppm)
7.30–7.47 (10H, m, Ph), 6.07 (1H, d, J=7.9 Hz), 4.72 (1H, d, J=11.6 Hz), 4.66 (1H, d, J=11.6 Hz), 4.61 (2H, d, J=11.6 Hz), 4.24–4.32 (1H, m), 4.45 (1H, d, J=11.6 Hz), 4.00 (1H, dt, $J_t$=7.3 Hz, $J_d$=4.3 Hz), 3.67–3.72 (2H, m), 3.61 (1H, ddd, J=4.3 Hz, 11.6 Hz, 8.6 Hz), 3.05 (1H, dd, J=4.3 Hz, 8.5 Hz), 1.94–2.05 (2H, m), 1.15–1.69 (72H, m), 0.88 (6H, t, J=6.1 Hz).

(xiii) Synthesis of the Compound E14

1) 1.33 g of a galactose derivative (F1) was dissolved in 5.0 ml of methylene chloride. 1.6 ml of bromotrimethylsilane was added to this solution, and the mixture was stirred at room temperature for 4 hours. The reaction mixture was concentrated as it was under reduced pressure, and then thoroughly dried in vacuum. The compound thus obtained was used in the following reaction.

2) 1.0 g of Compound E13 was dissolved in a mixture of 5.0 ml of methylene chloride and 5 ml of dimethylformamide. 1.5 g of activated molecular sieves 4A was added to the solution, and 480 mg of tetraethylammonium bromide was then added to the mixture. The resulting mixture was stirred. To this was added a methylene chloride solution (5.0 ml) of the galactose derivative (F2) prepared in the above process (1), and the mixture was stirred at room temperature for 16 hours. 10 ml of methylene chloride was added to the reaction mixture, and the resulting mixture was filtered through Celite. The residue was thoroughly washed with methylene chloride. The filtrate and the wash liquid were combined, washed with a saturated aqueous solution of sodium hydrogencarbonate and then with a saturated saline solution, dried over anhydrous magnesium sulfate, concentrated under reduced pressure, and purified by using a silica gel column (hexane:ethyl acetate=10:1 to 8:1). The amount of the compound obtained was 1.15 g, and the yield was 72.1%.

[Data]
FD-MS: 1399 ($C_{92}H_{135}NO_9$; Mw=1399.07)
$[\alpha]^{23}_D$=+18.8° (c=0.865, $CHCl_3$)
IR ($cm^{-1}$, KBr)
3320, 2919, 2850, 1647, 1533, 1470, 1454, 1348, 1144, 1028.
NMR: $^1H$ (500 MHz, $CDCl_3$)
δ (ppm)
7.21–7.37 (30H, m), 6.12 (1H, d, J=9.0 Hz), 4.91 (1H, d, J=11.6 Hz), 4.84 (1H, d, J=3.7 Hz), 4.72–4.80 (4H, m), 4.34–4.65 (7H, m), 4.12–4.18 (1H, m), 3.99–4.05 (2H, m), 4.12–4.18 (1H, m), 3.99–4.05 (2H, m), 3.84–3.93 (4H, m), 3.73 (1H, dd, J=3.7 Hz, 11.0 Hz), 3.47–3.51 (2H, m), 3.42 (1H, dd, J=6.1 Hz, 9.1 Hz), 1.87–1.99 (2H, m), 1.18–1.70 (72H, m), 0.88 (6H, t, J=7.4 Hz).

(xiv) Synthesis of the Compound 36

2.64 g of Compound E14 was dissolved in 30 ml of tetrahydrofuran, and 5% palladium-barium sulfate was added to this solution. The inside of a reactor was replaced by hydrogen gas. The mixture was stirred at room temperature for 16 hours under hydrogen atmosphere, and then filtered through Celite. The residue was washed with a 2:1 mixture of chloroform and methanol. The filtrate and the was liquid were combined, and concentrated under reduced pressure. The white powder thus obtained was dissolved in ethanol containing 8% of water while heating, and the solution was allowed to stand for cooling to precipitate Compound 36. The amount of the compound obtained was 1.48 g, and the yield was 91.4%. The data with respect to Compound 36 are the same as the above.

EXPERIMENTAL EXAMPLE 2

Anti-tumor activity of the compounds of the present invention

Anti-tumor activity against B16 mouse melanoma inoculated subcutaneously.

Experiment was carried out with the groups of 6 female $BDF_1$ mice (6 weeks old) purchased from Japan SLC Inc., B16 mouse melanoma cells ($1 \times 10^6$ cells/mouse) were inoculated subcutaneously in the rear region of mice, and the sample was administered intravenously at a dose of 0.1 mg/kg after 1, 5 and 9 days from inoculation (the day of inoculation being set as 0 day). The volume of the tumor at the hypodermis of the rear region [longer diameter×shorter diameter×height)/2] was measured on 8, 12, 16 and 20 days after inoculation, and the tumor growth inhibition rate (TGIR) of each sample was determined. TGIR was calculated from the following equation:

$$TGIR\ (\%) = (1 - T/C) \times 100$$

wherein C represents a tumor volume of the control group and T represents a tumor volume of the group to which the sample was administered.

Table 1 shows the maximum values of TGIR during the test period of 20 days. In this connection, respective test runs were divided by broken lines.

TABLE 1

Tumor growth inhibiting effects against B16 mouse melanoma cells

| Compound No. | TGIR (%) |
|---|---|
| 31 | 83.4 |
| 14 | 84.0 |
| 23 | 94.1 |
| 24 | 52.5 |
| 30 | 57.7 |
| 21 | 57.9 |
| 17 | 58.0 |
| 22 | 82.4 |
| 28 | 76.2 |
| 16 | 65.0 |
| 19 | 80.2 |
| 1 | 91.4 |
| 9 | 71.5 |
| 4 | 78.1 |
| 6 | 73.7 |
| 15 | 61.9 |
| 20 | 73.7 |
| 2 | 53.1 |
| 3 | 56.9 |
| 7 | 18.5 |
| 8 | 22.1 |
| 18 | 66.3 |
| 35 | 63.0 |
| 29 | 79.7 |
| 25 | 92.8 |
| 26 | 72.3 |
| 27 | 92.8 |
| 5 | 92.1 |
| 12 | 41.8 |
| 13 | 28.2 |
| 10 | 76.5 |
| 11 | 55.9 |
| 32 | 73.2 |
| 33 | 76.5 |
| 34 | 88.9 |
| 36 | 69.8 |
| 37 | 65.0 |

As shown in Table 1, all of the compounds inhibited the growth of tumor.

EXPERIMENTAL EXAMPLE 3

Immuno-stimulating activity of the compounds of the present invention

Lymphocyte mixed culture reaction

Experiment was carried out with the spleen cells of C57BL/6 mouse which had been treated with mitomycin C(50 μg/ml, 30 min) as the stimulator and with the pancreatic cells of BALB/c mouse as the responder. These pancreatic cells were suspended to a concentration of $2\times10^6$ cells/ml with a culture medium of 10% FCS RPMI 1640, respectively. These cells (50 μl/well) and a sample (10 μl/well) were plated in a 96 well round-bottomed plate and cultured for 42 hours* under the condition of 37° C. and 5% $CO_2$. $^3$H-thymidine ($^3$H-TdR) was added in a dose of 0.5 μCi/well. After 8 hours, the cells were harvested and subjected to the measurement of the uptake of $^3$H-TdR by a liquid scintillation counter.

*The samples of the compounds 32, 33 and 34 were cultured for 4 days.

TABLE 2

Uptake rate of $^3$H-TdR in respective sample concentrations

| Sample/Concentration (μg/ml) | Uptake of $^3$H-TdR (% of control) | | |
|---|---|---|---|
| (Compound) | $10^0$ | $10^{-1}$ | $10^{-2}$ |
| 1 | 359 | 151 | 136 |
| 2 | 329 | 115 | 103 |
| 3 | 254 | 117 | 110 |
| 4 | 269 | 158 | 134 |
| 5 | 473 | 170 | 153 |
| 6 | 498 | 190 | 187 |
| 7 | 853 | 576 | 207 |
| 8 | 297 | 189 | 96 |
| 9 | 460 | 193 | 176 |
| 10 | 610 | 381 | 157 |
| 11 | 128 | 105 | 95 |
| 12 | 123 | 99 | 104 |
| 13 | 139 | 106 | 107 |
| 14 | 289 | 197 | 139 |
| 15 | 360 | 165 | 144 |
| 16 | 321 | 176 | 160 |
| 17 | 410 | 190 | 143 |
| 18 | 482 | 176 | 138 |
| 19 | 345 | 188 | 144 |
| 20 | 443 | 188 | 192 |
| 21 | 304 | 149 | 142 |
| 22 | 414 | 166 | 149 |
| 23 | 423 | 167 | 143 |
| 24 | 416 | 167 | 144 |
| 25 | 230 | 179 | 161 |
| 26 | 253 | 199 | 193 |
| 27 | 257 | 181 | 162 |
| 28 | 357 | 172 | 141 |
| 29 | 319 | 382 | 215 |
| 30 | 385 | 156 | 134 |
| 31 | 398 | 235 | 163 |
| 32* | — | 406 | 426 |
| 33* | — | 365 | 422 |
| 34* | — | 360 | 406 |
| 35 | 562 | 261 | 247 |
| 36 | 562 | 283 | 251 |
| 37 | 495 | 261 | 267 |

As shown in Table 2, all of these samples exhibited lymphocyte mixed culture reaction stimulating activities.

EXPERIMENTAL EXAMPLE 4

Cytotoxicity

B16 melanoma cells which had been prepared in a concentration of $1\times10^5$ cells/ml and the compounds 1–37 which had been prepared in various concentrations were added to a 96 well flat-bottomed microplate in an amount of 100 μl/well and 10 μl/well, respectively. After culturing under the condition of 37° C. and 5% $CO_2$ for 42 hours, $^3$H-TdR was added in a dose of 0.5 μCi/well. After further 8 hours, the cells were harvested, and the uptake of $^3$H-TdR was measured by a liquid scintillation counter. None of the compounds even in the final concentration of 10 μg/ml influenced the proliferation of the cells.

EXPERIMENTAL EXAMPLE 5

Acute toxicity

The compounds 5 and 36 were once administered intravenously in doses of 0.1, 1.0 and 10 mg/kg to the groups of 6 male Crj:CD rats (5 weeks old), and the toxicity tests on compounds 5 and 36 were conducted for 7 days after the administration of these compounds.

As a result, even the dose of 10 mg/kg was not lethal to the animals, and no abnormality was observed at the autopsy, so that the $LD_{50}$ value of the compound is believed to be at least 10 mg/kg.

What is claimed is:

1. An α-galactosylceramide represented by the formula

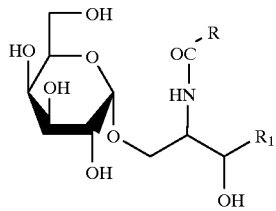 (A)

wherein

R represents

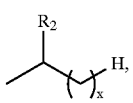

where $R_2$ represents H or OH and X denotes an integer of 0–26 or R represents $(CH_2)_7CH=CH(CH_2)_7CH_3$ and $R_1$ represents any one of the substituents defined by the following (a)–(e):

(a) —$CH_2(CH_2)_yCH_3$,
(b) —$CH(OH)(CH_2)_yCH_3$,
(c) —$CH(OH)(CH_2)_yCH(CH_3)_2$,
(d) —$CH=CH(CH_2)_yCH_3$, and
(e) —$CH(OH)(CH_2)_yCH(CH_3)CH_2CH_3$, wherein Y denotes an integer of 5–17.

2. An α-galactosylceramide according to claim 1, which is represented by the formula (I):

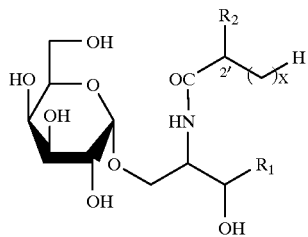 (I)

wherein $R_1$ represents any one of the substituents defined by (a)–(e) below and $R_2$ represents H or OH (X is defined in the following (a)–(e)):

—$CH_2(CH_2)_yCH_3$, (a)

wherein when $R_2$ represents H, X denotes an integer of 0–24 and Y denotes an integer of 7–15; when $R_2$ represents OH, X denotes an integer of 20–24 and Y denotes an integer of 11–15;

—$CH(OH)(CH_2)_yCH_3$, (b)

wherein when $R_2$ represents H, X denotes an integer of 18–26 and Y denotes an integer of 5–15; when $R_2$ represents OH, X denotes an integer of 18–26 and Y denotes an integer of 5–17;

—$CH(OH)(CH_2)_yCH(CH_3)_2$, (c)

wherein when $R_2$ represents H, X denotes an integer of 20–24 and Y denotes an integer of 9–13; when $R_2$ represents OH, X denotes an integer of 18–24 and Y denotes an integer of 9–13;

—$CH=CH(CH_2)_yCH_3$, (d)

wherein $R_2$ represents H, X denotes an integer of 10–18 and Y denotes an integer of 10–14; and —$CH(OH)(CH_2)_yCH(CH_3)CH_2CH_3$, (e)

wherein $R_2$ represents OH, X denotes an integer of 21–25 and Y denotes an integer of 9–13.

3. An α-galactosylceramide according to claim 2, which is represented by the formula (II):

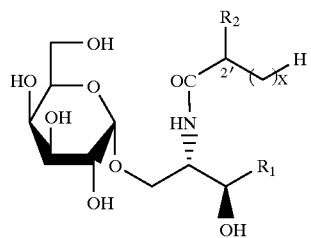 (II)

wherein $R_1$ represents any one of the substituents defined by (a)–(e) below and $R_2$ represents H or OH (X is defined in the following (a)–(e)):

—$CH_2(CH_2)_yCH_3$, (a)

wherein when $R_2$ represents H, X denotes an integer of 0–24 and Y denotes an integer of 7–15; when $R_2$ represents OH, X denotes an integer of 20–24 and Y denotes an integer of 11–15;

—$CH(OH)(CH_2)_yCH_3$, (b)

wherein when $R_2$ represents H, X denotes an integer of 18–26 and Y denotes an integer of 5–15; when $R_2$ represents OH, X denotes an integer of 18–26 and Y denotes an integer of 5–17;

—$CH(OH)(CH_2)_yCH(CH_3)_2$, (c)

wherein when $R_2$ represents H, X denotes an integer of 20–24 and Y denotes an integer of 9–13; when $R_2$ represents OH, X denotes an integer of 18–24 and Y denotes an integer of 9–13;

—$CH=CH(CH_2)_yCH_3$, (d)

wherein $R_2$ represents H, X denotes an integer of 10–18 and Y denotes an integer of 10–14; and —$CH(OH)(CH_2)_yCH(CH_3)CH_2CH_3$, (e)

wherein $R_2$ represents OH, X denotes an integer of 21–25 and Y denotes an integer of 9–13.

4. An α-galactosylceramide according to claim 2, which is represented by the formula (III):

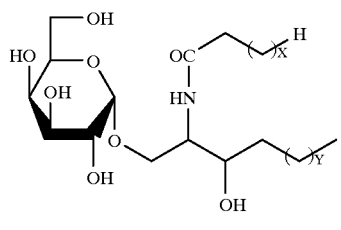
(III)

wherein X denotes an integer of 0–24 and Y denotes an integer of 7–15.

5. An α-galactosylceramide according to claim 4, wherein X denotes an integer of 8–22 and Y denotes an integer of 9–13.

6. An α-galactosylceramide according to claim 4, which is represented by the formula (IV):

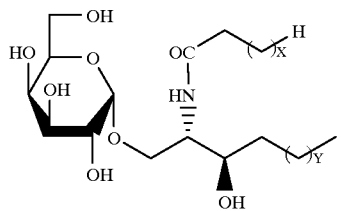
(IV)

wherein X denotes an integer of 0–24 and Y denotes an integer of 7–15.

7. An α-galactosylceramide according to claim 6, wherein X denotes an integer of 8–22 and Y denotes an integer of 9–13.

8. An α-galactosylceramide according to claim 2, which is represented by the formula (V):

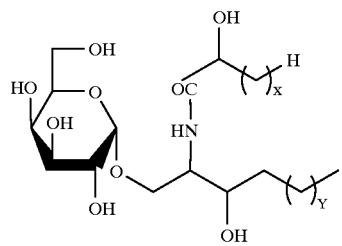
(V)

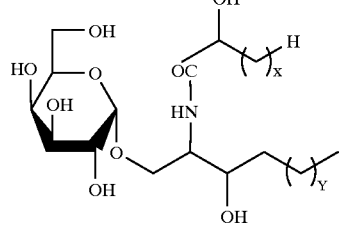
(V)

wherein X denotes an integer of 20–24 and Y denotes an integer of 11–15.

9. An α-galactosylceramide according to claim 8, wherein X denotes an integer of 21–23 and Y denotes an integer of 12–14.

10. An α-galactosylceramide according to claim 8, is represented by the formula (VI):

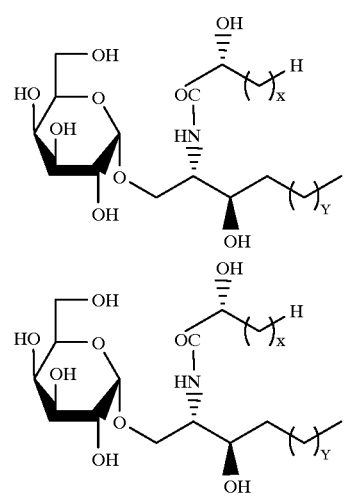
(VI)

(VI)

wherein X denotes an integer of 20–24 and Y denotes an integer of 11–15.

11. An α-galactosylceramide according to claim 10, wherein X denotes an integer of 21–23 and Y denotes an integer of 12–14.

12. An α-galactosylceramide according to claim 2, which is represented by the formula (VII):

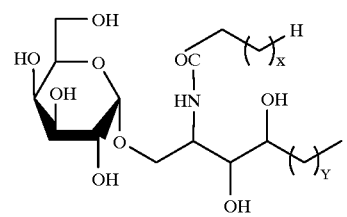
(VII)

wherein X denotes an integer of 18–26 and Y denotes an integer of 5–15.

13. An α-galactosylceramide according to claim 12, wherein X denotes an integer of 21–25 and Y denotes an integer of 6–14.

14. An α-galactosylceramide according to claim 12, which is represented by the formula (VIII):

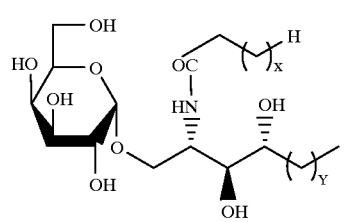
(VIII)

wherein X denotes an integer of 18–26 and Y denotes an integer of 5–15.

15. An α-galactosylceramide according to claim 14, wherein X denotes an integer of 21–25 and Y denotes an integer of 6–14.

16. An α-galactosylceramide according to claim 2, which is represented by the formula (IX):

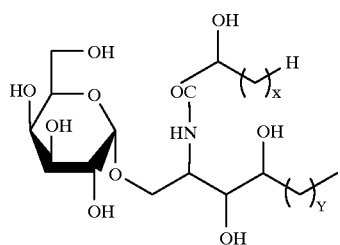

(IX)

wherein X denotes an integer of 18–26 and Y denotes an integer of 5–17.

17. An α-galactosylceramide according to claim 16, wherein X denotes an integer of 21–25 and Y denotes an integer of 6–16.

18. An α-galactosylceramide according to claim 16, which is represented by the formula (X):

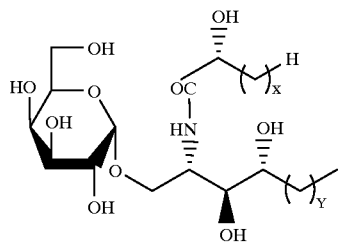

(X)

wherein X denotes an integer of 18–26 and Y denotes an integer of 5–17.

19. An α-galactosylceramide according to claim 16, which is represented by the formula (X'):

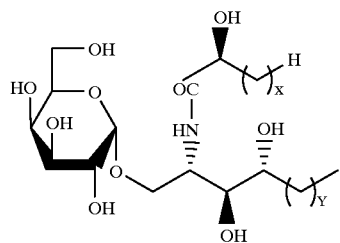

(X')

wherein X denotes an integer of 20–24 and Y denotes an integer of 10–14.

20. An α-galactosylceramide according to claim 18, wherein X denotes an integer of 21–25 and Y denotes an integer of 6–16.

21. An α-galactosylceramide according to claim 19, wherein X denotes an integer of 21–23 and Y denotes an integer of 11–13.

22. An α-galactosylceramide according to claim 2, which is represented by the formula (XI):

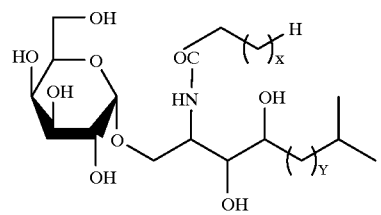

(XI)

wherein X denotes an integer of 20–24 and Y denotes an integer of 9–13.

23. An α-galactosylceramide according to claim 22, wherein X denotes an integer of 21–23 and Y denotes an integer of 10–12.

24. An α-galactosylceramide according to claim 22, which is represented by the formula (XII):

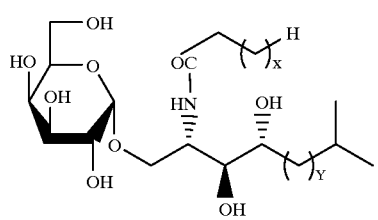

(XII)

wherein X denotes an integer of 20–24 and Y denotes an integer of 9–13.

25. An α-galactosylceramide according to claim 24, wherein X denotes an integer of 21–23 and Y denotes an integer of 10–12.

26. An α-galactosylceramide according to claim 2, which is represented by the formula (XIII):

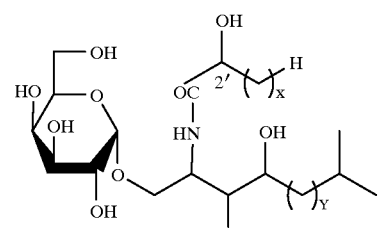

(XIII)

wherein X denotes an integer of 18–24 and Y denotes an integer of 9–13.

27. An α-galactosylceramide according to claim 26, wherein X denotes an integer of 20–23 and Y denotes an integer of 10–12.

28. An α-galactosylceramide according to claim 26, which is represented by the formula (XIV):

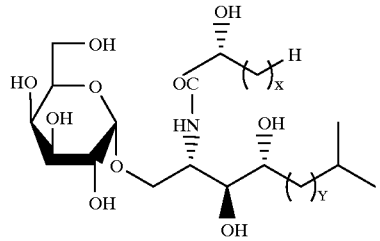

(XIV)

wherein X denotes an integer of 19–23 and Y denotes an integer of 9–13.

29. An α-galactosylceramide according to claim 26, which is represented by the formula (XIV'):

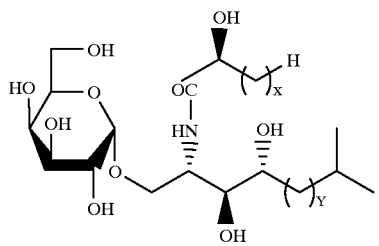

wherein X denotes an integer of 20–24 and Y denotes an integer of 9–13.

30. An α-galactosylceramide according to claim 28, wherein X denotes an integer of 20–22 and Y denotes an integer of 10–12.

31. An α-galactosylceramide according to claim 29, wherein X denotes an integer of 21–23 and Y denotes an integer of 10–12.

32. An α-galactosylceramide according to claim 2, which is represented by the formula (XV):

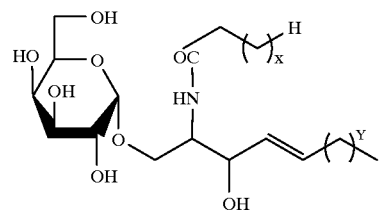

wherein X denotes an integer of 10–18 and Y denotes an integer of 10–14.

33. An α-galactosylceramide according to claim 32, wherein X denotes an integer of 11–17 and Y denotes an integer of 11–13.

34. An α-galactosylceramide according to claim 32, which is represented by the formula (XVI):

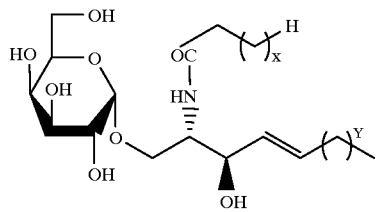

wherein X denotes an integer of 10–18 and Y denotes an integer of 10–14.

35. An α-galactosylceramide according to claim 34, wherein X denotes an integer of 11–17 and Y denotes an integer of 11–13.

36. An α-galactosylceramide according to claim 2, which is represented by the formula (XVII):

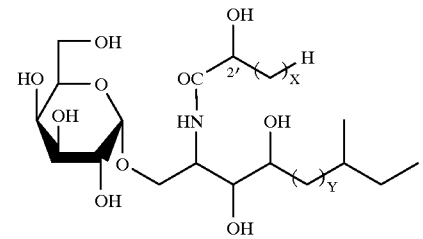

wherein X denotes an integer of 21–25 and Y denotes an integer of 9–13.

37. An α-galactosylceramide according to claim 36, wherein X denotes an integer of 22–24 and Y denotes an integer of 10–12.

38. An α-galactosylceramide according to claim 36, which is represented by the formula (XVIII):

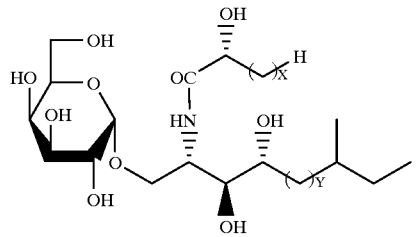

wherein X denotes an integer of 21–25 and Y denotes an integer of 9–13.

39. An α-galactosylceramide according to claim 38, wherein X denotes an integer of 22–24 and Y denotes an integer of 10–12.

40. An α-galactosylceramide according to claim 1, which is represented by the formula (XIX):

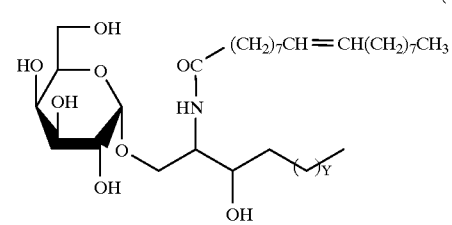

wherein Y denotes an integer of 11–15.

41. An α-galactosylceramide according to claim 40, wherein Y denotes an integer of 12–14.

42. An α-galactosylceramide according to claim 40, which is represented by the formula (XX):

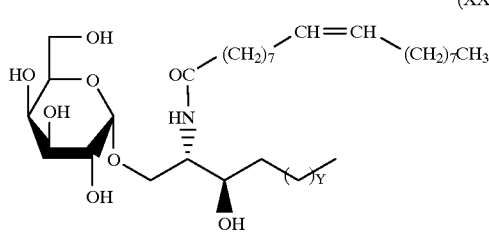

wherein Y denotes an integer of 11–15.

43. An α-galactosylceramide according to claim 42, wherein Y denotes an integer of 12–14.

44. A process for inhibiting a tumor comprising administering an effective amount of one or more of the compounds according to claim 1 to a patient who needs inhibition of a tumor.

45. A process for stimulating the immune system comprising administering an effective amount of one or more of the compounds according to claim 1 to a patient who needs stimulation of the immune system.

46. A pharmaceutical composition comprising one or more of the compounds according to claim 1 as an effective ingredient and a pharmaceutically acceptable carrier or diluent.

47. An α-galactosylceramide according to claim 1 wherein R represents

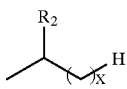

$R_2$ represents OH and $R_1$ represents —CH(OH) $(CH_2)_y CH_3$; —CH(OH) $(CH_2)_y CH(CH_3)_2$; or —CH(OH)(CH$_2$)$_y$CH (CH$_3$)CH$_2$CH$_3$ and Y is an integer of 5–17.

48. An α-galactosylceramide according to claim 1, which is selected from the group consisting of the following compounds:

(1) (2S,3R)-1-(α-D-galactopyranosyloxy)-2-tetracosanoylamino-3-octadecanol,
(2) (2S,3R)-2-docosanoylamino-1-(α-D-galactopyranosyloxy)-3-octadecanol,
(3) (2S,3R)-1-(α-D-galactopyranosyloxy)-2-icosanoylamino-3-octadecanol,
(4) (2S,3R)-1-(α-D-galactopyranosyloxy)-2-octadecanoylamino-3-octadecanol,
(5) (2S,3R)-1-(α-D-galactopyranosyloxy)-2-tetradecanoylamino-3-octadecanol,
(6) (2S,3R)-2-decanoylamino-1-(α-D-galactopyranosyloxy)-3-octadecanol,
(7) (2S,3R)-1-(α-D-galactopyranosyloxy)-2-tetracosanoylamino-3-tetradecanol,
(8) (2S,3R)-1-(α-D-galactopyranosyloxy)-2-tetradecanoylamino-3-hexadecanol,
(9) (2R,3S)-1-(α-D-galactopyranosyloxy)-2-tetradecanoylamino-3-hexadecanol,
(10) (2S,3S)-1-(α-D-galactopyranosyloxy)-2-tetradecanoylamino-3-hexadecanol,
(11) (2S,3R)-1-(α-D-galactopyranosyloxy)-2[(R)-2-hydroxytetracosanoylamino]-3-octadecanol,
(12) (2S,3R,4E)-1-(α-D-galactopyranosyloxy)-2-octadecanoylamino-4-octadecen-3-ol,
(13) (2S,3R,4E)-1-(α-D-galactopyranosyloxy)-2-tetradecanoylamino-4-octadecen-3-ol,
(14) (2S,3S,4R)-1-(α-D-galactopyranosyloxy)-2-tetracosanoylamino-3,4-octadecanediol,
(15) (2S,3S,4R)-1-(α-D-galactopyranosyloxy)-2-tetracosanoylamino-3,4-heptadecanediol,
(16) (2S,3S,4R)-1-(α-D-galactopyranosyloxy)-2-tetracosanoylamino-3,4-pentadecanediol,
(17) (2S,3S,4R)-1-(α-D-galactopyranosyloxy)-2-tetracosanoylamino-3,4-undecanediol,
(18) (2S,3S,4R)-1-(α-D-galactopyranosyloxy)-2-hexacosanoylamino-3,4-heptadecanediol,
(19) (2S,3S,4R)-1-(α-D-galactopyranosyloxy)-2-[(R)-2-hydroxytetracosanoylamino]-3,4-octadecanediol,
(20) (2S,3S,4R)-1-(α-D-galactopyranosyloxy)-2-[(R)-2-hydroxytetracosanoylamino]-3,4-heptadecanediol,
(21) (2S,3S,4R)-1-(α-D-galactopyranosyloxy)-2-[(R)-2-hydroxytetracosanoylamino]-3,4-pentadecanediol,
(22) (2S,3S,4R)-1-(α-D-galactopyranosyloxy)-2-[(R)-2-hydroxytetracosanoylamino]-3,4-undecanediol,
(23) (2S,3S,4R)-1-(α-D-galactopyranosyloxy)-2-[(R)-2-hydroxyhexacosanoylamino]-3,4-octadecanediol,
(24) (2S,3S,4R)-1-(α-D-galactopyranosyloxy)-2-[(R)-2-hydroxyhexacosanoylamino]-3,4-nonadecanediol,
(25) (2S,3S,4R)-1-(α-D-galactopyranosyloxy)-2-[(R)-2-hydroxyhexacosanoylamino]-3,4-icosanediol,
(26) (2S,3S,4R)-1-(α-D-galactopyranosyloxy)-2-[(S)-2-hydroxytetracosanoylamino]-3,4-heptadecanediol,
(27) (2S,3S,4R)-1-(α-D-galactopyranosyloxy)-2-[(R)-2-hydroxytetracosanoylamino]-3,4-hexadecanediol,
(28) (2S,3S,4R)-1-(α-D-galactopyranosyloxy)-2-[(S)-2-hydroxytetracosanoylamino]-16-methyl-3,4-heptadecanediol,
(29) (2S,3S,4R)-1-(α-D-galactopyranosyloxy)-16-methyl-2-tetracosanoylamino-3,4-heptadecanediol,
(30) (2S,3S,4R)-1-(α-D-galactopyranosyloxy)-2-[(R)-2-hydroxytricosanoylamino]-16-methyl-3,4-heptadecanediol,
(31) (2S,3S,4R)-1-(α-D-galactopyranosyloxy)-2-[(R)-2-hydroxypentacosanoylamino]-16-methyl-3,4-octadecanediol,
(32) (2S,3R)-1-(α-D-galactopyranosyloxy)-2-oleoylamino-3-octadecanol,
(33) (2S,3S,4R)-1-(α-D-galactopyranosyloxy)-2-hexacosanoylamino-3,4-octadecanediol;
(34) (2S,3S,4R)-1-(α-D-galactopyranosyloxy)-2-octacosanoylamino-3,4-heptadecanediol and
(35) (2R,3R)-1-(α-D-galactopyranosyloxy)-2-tetradecanoylamino-3-hexadecanol.

49. An α-galactosylceramide according to claim 48, which is selected from the group consisting of the following compounds:

(1) (2S,3R)-1-(α-D-galactopyranosyloxy)-2-tetracosanoylamino-3-octadecanol,
(2) (2S,3R)-2-docosanoylamino-1-(α-D-galactopyranosyloxy)-3-octadecanol,
(3) (2S,3R)-1-(α-D-galactopyranosyloxy)-2-icosanoylamino-3-octadecanol,
(4) (2S,3R)-1-(α-D-galactopyranosyloxy)-2-octadecanoylamino-3-octadecanol,
(5) (2S,3R)-1-(α-D-galactopyranosyloxy)-2-tetradecanoylamino-3-octadecanol,
(6) (2S,3R)-2-decanoylamino-1-(α-D-galactopyranosyloxy)-3-octadecanol,
(7) (2S,3R)-1-(α-D-galactopyranosyloxy)-2-tetracosanoylamino-3-tetradecanol, and
(8) (2S,3R)-1-(α-D-galactopyranosyloxy)-2-tetradecanoylamino-3-hexadecanol.

50. An α-galactosylceramide according to claim 49 which is selected from the group consisting of the following compounds:

(1) (2S,3R)-1-(α-D-galactopyranosyloxy)-2-tetracosanoylamino-3-octadecanol,
(2) (2S,3R)-2-docosanoylamino-1-(α-D-galactopyranosyloxy)-3-octadecanol, (3) (2S,3R)-1-(α-D-galactopyranosyloxy)-2-icosanoylamino-3-octadecanol, (4) (2S,3R)-1-(α-D-galactopyranosyloxy)-2-octadecanoylamino-3-octadecanol, (5) (2S,3R)-1-(α-D-galactopyranosyloxy)-2-tetradecanoylamino-3-octadecanol, (6) (2S,3R)-2-decanoylamino-1-(α-D-galactopyranosyloxy)-3-octadecanol, (7) (2S,3R)-1-(α-D-galactopyranosyloxy)-2-tetracosanoylamino-3-tetradecanol, and (8) (2S,3R)-1-(α-D-galactopyranosyloxy)-2-tetradecanoylamino-3-hexadecanol.

51. An α-galactosylceramide according to claim 50 which is selected from the group consisting of the following compounds:

(1) (2S,3R)-1-(α-D-galactopyranosyloxy)-2-octadecanoylamino-3-octadecanol, (2) (2S,3R)-1-(α-D-galactopyranosyloxy)-2-tetradecanoylamino-3-octadecanol, and (3) (2S,3R)-1-(α-D-galactopyranosyloxy)-2-tetradecanoylamino-3-hexadecanol.

52. An α-galactosylceramide according to claim 48, which is (2S,3R)-1-(α-D-galactopyranosyloxy)-2-[(R)-2-hydroxytetracosanoylamino]-3-octadecanol.

53. An α-galactosylceramide according to claim 48, which is selected from the group consisting of the following (1) (2S,3R,4E)-1-(α-D-galactopyranosyloxy)-2-octadecanoylamino-4-octadecen-3-ol, and (2) (2S,3R,4E)-1-(α-D-galactopyranosyloxy)-2-tetradecanoylamino-4-octadecen-3-ol.

54. An α-galactosylceramide according to claim 48 which is selected from the group consisting of the following compounds:

(1) (2S,3S,4R)-1-(α-D-galactopyranosyloxy)-2-tetracosanoylamino-3,4-octadecanediol, (2) (2S,3S,4R)-1-(α-D-galactopyranosyloxy)-2-tetracosanoylamino-3,4-heptadecanediol, (3) (2S,3S,4R)-1-(α-D-galactopyranosyloxy)-2-tetracosanoylamino-3,4-pentadecanediol, (4) (2S,3S,4R)-1-(α-D-galactopyranosyloxy)-2-tetracosanoylamino-3,4-undecanediol, (5) (2S,3S,4R)-1-(α-D-galactopyranosyloxy)-2-hexacosanoylamino-3,4-heptadecanediol, (6) (2S,3S,4R)-1-(α-D-galactopyranosyloxy)-2-hexacosanoylamino-3,4-octadecanediol; and (7) (2S,3S,4R)-1-(α-D-galactopyranosyloxy)-2-octacosanoylamino-3,4-heptadecanediol.

55. An α-galactosylceramide according to claim 54, which is (2S,3S,4R)-1-(α-D-galactopyranosyloxy)-2-hexacosanoylamino-3,4-octadecanediol.

56. An α-galactosylceramide according to claim 48, which is selected from the group consisting of the following compounds:

(1) (2S,3S,4R)-1-(α-D-galactopyranosyloxy)-2-[(R)-2-hydroxytetracosanoylamino]-3,4-octadecanediol, (2) (2S,3S,4R)-1-(α-D-galactopyranosyloxy)-2-[(R)-2-hydroxytetracosanoylamino]-3,4-heptadecanediol, (3) (2S,3S,4R)-1-(α-D-galactopyranosyloxy)-2-[(R)-2-hydroxytetracosanoylamino]-3,4-pentadecanediol, (4) (2S,3S,4R)-1-(α-D-galactopyranosyloxy)-2-[(R)-2-hydroxytetracosanoylamino]-3,4-undecanediol, (5) (2S,3S,4R)-1-(α-D-galactopyranosyloxy)-2-[(R)-2-hydroxyhexacosanoylamino]-3,4-octadecanediol, (6) (2S,3S,4R)-1-(α-D-galactopyranosyloxy)-2-[(R)-2-hydroxyhexacosanoylamino]-3,4-nonadecanediol, (7) (2S,3S,4R)-1-(α-D-galactopyranosyloxy)-2-[(R)-2-hydroxyhexacosanoylamino]-3,4-icosanediol, (8) (2S,3S,4R)-1-(α-D-galactopyranosyloxy)-2-[(S)-2-hydroxytetracosanoylamino]-3,4-heptadecanediol, and (9) (2S,3S,4R)-1-(α-D-galactopyranosyloxy)-2-[(R)-2-hydroxytetracosanoylamino]-3,4-hexadecanediol.

57. An α-galactosylceramide according to claim 56, which is (2S,3S,4R)-1-(α-D-galactopyranosyloxy)-2-[(R)-2-hydroxyhexacosanoylamino]-3,4-octadecanediol.

58. An α-galactosylceramide according to claim 48, which is selected from the group consisting of the following compounds:

(1) (2S,3S,4R)-1-(α-D-galactopyranosyloxy)-2-[(S)-2-hydroxytetracosanoylamino]-16-methyl-3,4-heptadecanediol, (2) (2S,3S,4R)-1-(α-D-galactopyranosyloxy)-16-methyl-2-tetracosanoylamino-3,4-heptadecanediol, and (3) (2S,3S,4R)-1-(α-D-galactopyranosyloxy)-2-[(R)-2-hydroxytricosanoylamino]-16-methyl-3,4-heptadecanediol.

59. An α-galactosylceramide according to claim 48, which is (2S,3S,4R)-1-(α-D-galactopyranosyloxy)-2-[(R)-2-hydroxypentacosanoylamino]-16-methyl-3,4-octadecanediol.

60. An α-galactosylceramide according to claim 48, which is (2S,3R)-1-(α-D-galactopyranosyloxy)-2-oleoylamino-3-octadecanediol.

* * * * *